US008590381B2

(12) United States Patent
Murai et al.

(10) Patent No.: US 8,590,381 B2
(45) Date of Patent: *Nov. 26, 2013

(54) ULTRASONIC FLAW DETECTION METHOD AND ULTRASONIC FLAW DETECTION EQUIPMENT

(75) Inventors: Junichi Murai, Higashiosaka (JP); Dominique Braconnier, Higashiosaka (JP)

(73) Assignee: Krautkramer Japan, Co., Ltd., Tokyo (JP)

(*) Notice: Subject to any disclaimer, the term of this patent is extended or adjusted under 35 U.S.C. 154(b) by 265 days.

This patent is subject to a terminal disclaimer.

(21) Appl. No.: 12/935,418

(22) PCT Filed: Mar. 17, 2009

(86) PCT No.: PCT/JP2009/055209
§ 371 (c)(1),
(2), (4) Date: Sep. 29, 2010

(87) PCT Pub. No.: WO2009/122904
PCT Pub. Date: Oct. 8, 2009

(65) Prior Publication Data
US 2011/0030479 A1  Feb. 10, 2011

(30) Foreign Application Priority Data

Mar. 31, 2008 (JP) ................................. 2008-089594

(51) Int. Cl.
*G01N 29/26* (2006.01)
*G01N 29/38* (2006.01)
*G01N 29/07* (2006.01)

(52) U.S. Cl.
USPC .................. 73/602; 73/622; 73/624; 73/625; 73/626; 73/628

(58) Field of Classification Search
USPC ................... 73/602, 624, 625, 626, 628, 622
See application file for complete search history.

(56) References Cited

U.S. PATENT DOCUMENTS 3,981,184 A * 9/1976 Matay .............................. 73/609
4,320,659 A * 3/1982 Lynnworth et al. ............. 73/589
4,528,854 A * 7/1985 Shimazaki ....................... 73/626
(Continued)

FOREIGN PATENT DOCUMENTS

JP  2003-28846 A  1/2003
JP  2003028846 A * 1/2003
(Continued)

OTHER PUBLICATIONS

Murai et al., "Volume Focusing Phased Array and Applications", Journal of JSNDI, Oct. 1, 2007, vol. 56 No. 10, pp. 525-529, and 554.

*Primary Examiner* — Peter Macchiarolo
*Assistant Examiner* — Rose M Miller
(74) *Attorney, Agent, or Firm* — Birch, Stewart, Kolasch & Birch, LLP

(57) ABSTRACT

Equipment of the invention provides ultrasonic flaw detection equipment using a volume focusing flaw detection method, the ultrasonic flaw detection equipment described below. That is, this equipment performs internal flaw detection of a material being tested, the material having a virtually circular cross-sectional shape, and transducers 1 . . . 1 are arranged in an arc along a circle exhibited by the material being tested. Array probes 10 . . . 10 are disposed so as to surround the material being tested. An exciting unit enables flaw detection of the material being tested to be performed by vertical and oblique flaw detection methods. The exciting unit makes ultrasonic waves enter the material being tested from each position on an incident section as a result of a plurality of transducers being vibrated once and makes the ultrasonic waves reach a counter section facing the incident section on the circumference of the circle exhibited by the material being tested, and the exciting unit makes the ultrasonic waves enter the material being tested as a result of the plurality of transducers being vibrated one more time and makes the ultrasonic waves allowed to enter reach one of adjacent sections adjacent to the counter section.

20 Claims, 21 Drawing Sheets

(56) References Cited

U.S. PATENT DOCUMENTS

| | | | |
|---|---|---|---|
| 4,537,073 A * | 8/1985 | Ooshiro et al. | 73/602 |
| 5,007,291 A * | 4/1991 | Walters et al. | 73/640 |
| 7,779,694 B2 * | 8/2010 | Iizuka | 73/622 |
| 2011/0126626 A1 * | 6/2011 | Koch et al. | 73/632 |

FOREIGN PATENT DOCUMENTS

| | | | |
|---|---|---|---|
| JP | 2003-130859 A | | 5/2003 |
| JP | 3704065 B | * | 10/2005 |
| JP | 3704065 B2 | | 10/2005 |
| JP | 2006-250873 A | | 9/2006 |

* cited by examiner

F I G 15
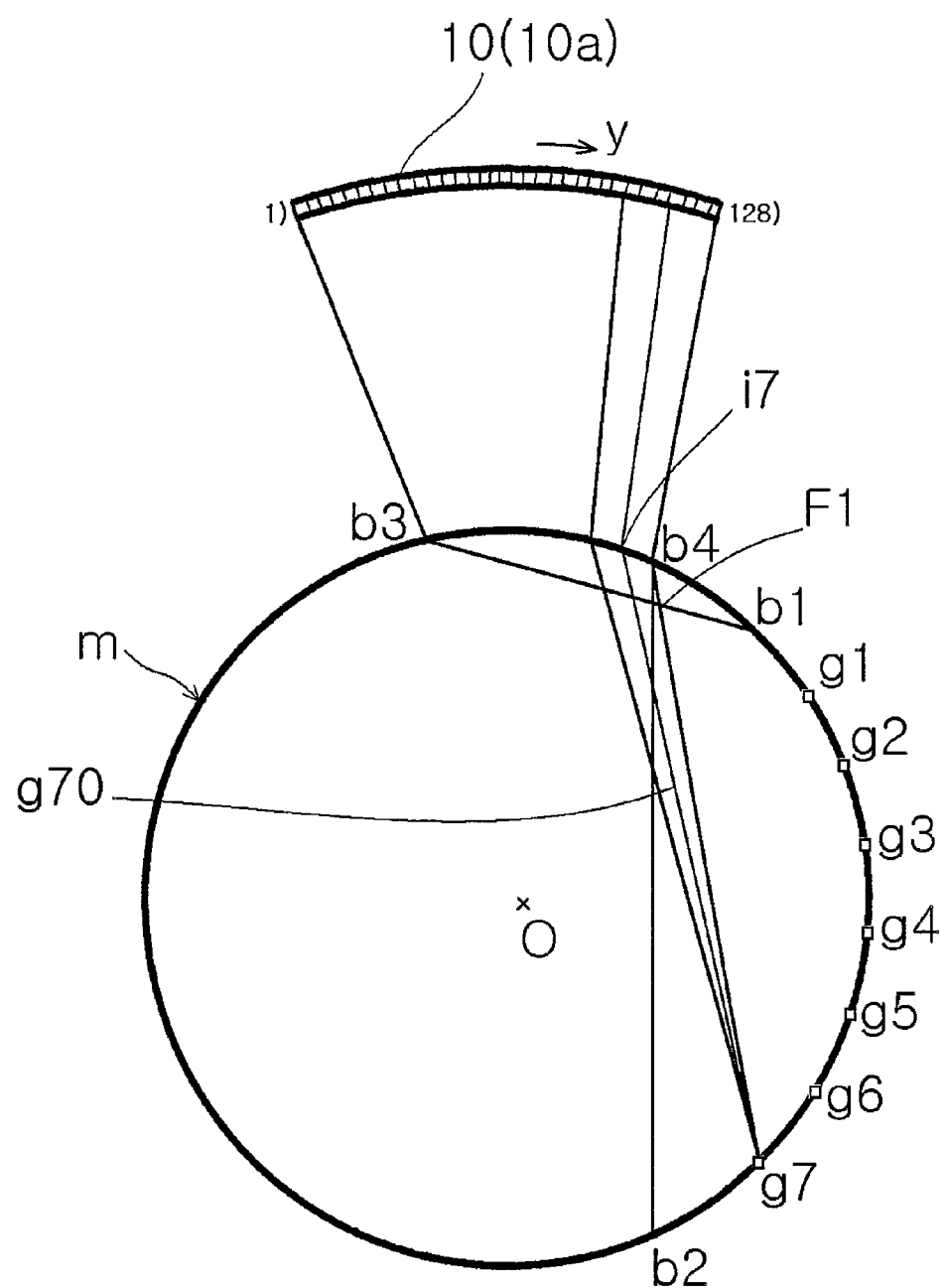

F I G 20
(A)
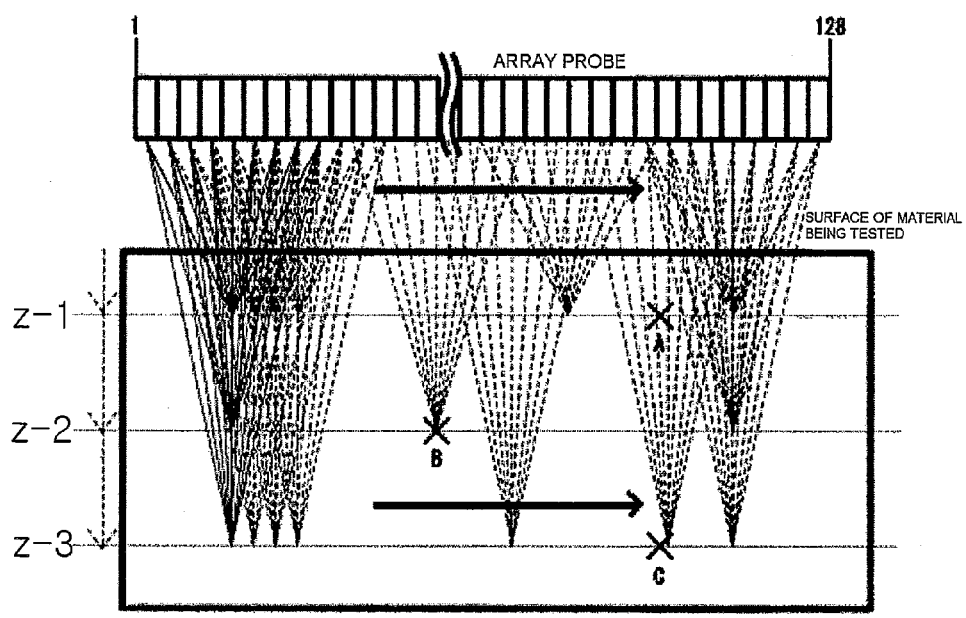
(B)
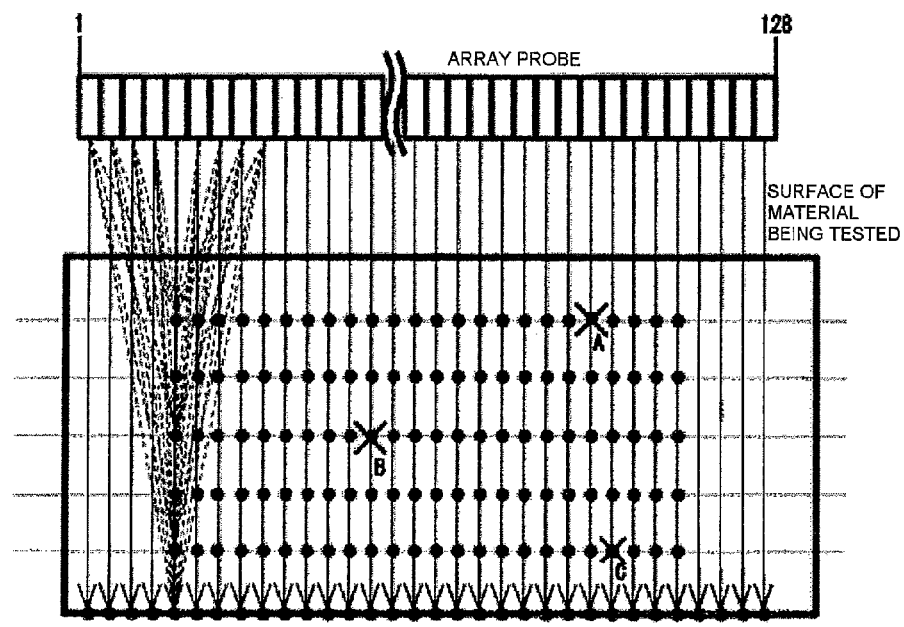

F I G 21
(A) VERTICAL FLAW DETECTION
(CENTRAL DEFECT)
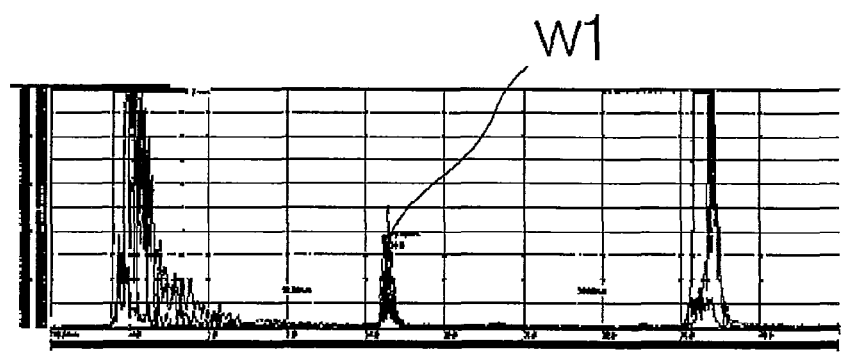
(B) OBLIQUE FLAW DETECTION
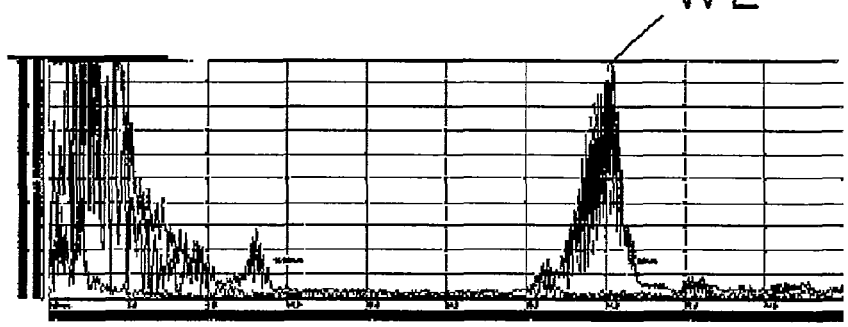

ULTRASONIC FLAW DETECTION METHOD AND ULTRASONIC FLAW DETECTION EQUIPMENT

TECHNICAL FIELD

The present invention relates to an ultrasonic flaw detection method and ultrasonic flaw detection equipment.

BACKGROUND ART

Patent Document 1: JP-A-2003-130859
Patent Document 2: Japanese Patent No. 3704065
Patent Document 3: JP-A-2006-250873
Nonpatent Literature 1: Takeko Murakami, Dominique Braconnier, Shunji Miura, Junichi Murai, Yutaka Nishitani, Proceedings of the 13th Symposium on Ultrasonic Testing, pp. 33-38, (2006)
Nonpatent Literature 2: Yoshikazu Yokono, Present Situation of Standardization of Phased Array UT, NDI Document 21776, pp. 34-38 (2006)

In a conventional flaw detection method using a single transducer, when internal flaw detection of a rod having the shape of a cylindrical column, for example, is performed, it is necessary to make the transducer perform scanning mechanically not only along an axial direction of the rod but also, with respect to a cross section thereof intersecting with the axial direction, along the circumference of a cross section of a material being tested.

In ultrasonic flaw detection of a material being tested, the ultrasonic flaw detection which has recently come into widespread use and is performed by using a phased array probe (hereinafter referred to as an array probe), a direction in which ultrasonic waves propagate and a point (focus) to which the ultrasonic waves converge can be arbitrarily set without a change in the placement of transducers by changing timing with which the individual transducers emit the ultrasonic waves (by performing phase control) (Patent Document 1).

As a result, in the above-described ultrasonic flaw detection using a phased array probe, instead of performing scanning mechanically along the surface of the material being tested, scanning is performed electrically.

This scanning is performed as follows. Instead of moving each transducer itself physically, as shown in FIG. 4 of Patent Document 1, the arranged transducers are sequentially vibrated in a time-shared manner so that a unit of a predetermined number of transducers is vibrated at a time. That is, of the transducers arranged in a scanning direction, a predetermined group of consecutive transducers emits ultrasonic waves, then a shift in the scanning direction is performed, and the next group emits the ultrasonic waves. By performing such a shift, it is possible to obtain the same effects as those obtained when the transducers are made to scan physically.

Patent Document 1 discloses electronic scanning (scanning performed by sequentially exciting a plurality of arranged transducers forming an array probe, instead of physically moving the transducers) using an array probe, the electronic scanning to be performed on a material being tested, the material having a linear surface as seen in a sectional view.

Moreover, Patent Document 3 discloses a method for performing electronic scanning on a cylindrical material being tested, the material having a circular surface, along the circumference thereof in the same manner as described above.

In addition, as a flaw detection technique that enables faster and higher-resolution flaw detection with higher detection capability based on the above-described conventional phased array flaw detection technique, a volume focusing phased array (hereinafter referred to as volume focusing if necessary) has been proposed (Nonpatent Literature 1 and Patent Document 2).

The above-described phased array flaw detection method has made remarkable advance in the past decade or so, and many apparatuses including a portable flaw detector and automatic flaw detection equipment have come to be used. This is attributed to the following reasons: a high-performance and low-cost flaw detector is made possible by the advancement of semiconductor technology and computer technology, and high-performance array search units (array probes) which are uniform in quality can be produced by the advent of a composite transducer.

The phased array flaw detection method finds wide application in ISI (In Service Inspection) of a nuclear power plant, an inspection of the fuselage and wings of an aircraft, online equipment used in the steel industry, and the like. Moreover, the movement toward standardization has also become active (Nonpatent Literature 2). In Japan, a phased array method is used also in an ultrasonic certification system in PD (Performance Demonstration) and achieves satisfactory results.

Volume focusing is a technique that enables faster and higher-resolution flaw detection with higher detection capability in these applications.

Hereinafter, applications of volume focusing will be described based on the principles thereof.

As volume focusing ultrasonic flaw detection equipment, desktop equipment and online-capable equipment have been proposed.

The desktop equipment is suitable for use in a field or for research purposes, has a flaw detection data analysis capability, and is adaptable to a matrix probe, which will be described later.

The online-capable equipment has a capability required for online automatic flaw detection, has a high-speed judgment capability, and can use a plurality of probes by performing parallel running.

Here, prior to an explanation of volume focusing, the above-described phased array flaw detection technique will be explained in more detail.

The basics of a conventional phased array inspection technique is to set a delay pattern to a virtual probe so that a group of transducers (a group of transducers performing transmission and reception concurrently: a virtual probe) obtains the same result as a focusing lens. An electric circuit of an array flaw detector scans each transmitted pulse (called a cycle or a time slot) at high speed at different settings. This operation may be considered as performing flaw detection by making the virtual probes that are set differently scan in sequence. Therefore, such array flaw detection has a great advantage over flaw detection using a single probe.

However, as is the case with multimode flaw detection, a temporal restriction is put on this method because transmission and reception is performed on a cycle-by-cycle basis. When a PRF (pulse repeat frequency) increases, a ghost echo caused by a multiple echo due to the front surface or a multiple echo in the material occurs, affecting a flaw detection speed. This problem is similar to that of a single probe.

That is, since this method repeats the following process: transmit and receive the ultrasonic waves, then perform electronic scanning, and then transmit and receive the ultrasonic waves again, the next transmission and reception of the ultrasonic waves cannot be performed until a ghost echo caused by the former emission of the ultrasonic waves is attenuated and ceases to exert an influence. This makes it necessary to lengthen a cycle of the former transmission and reception of the ultrasonic waves and the next transmission and reception of the ultrasonic waves.

On the other hand, as a method that enables high-sensitive flaw detection with high azimuth resolution, there is a zone focusing technique. The zone focusing technique performs flaw detection by connecting the focuses with respect to a zone set in a depth direction by performing transmission and reception while performing linear scanning. The focus can be set hierarchically, and high-sensitive flaw detection with high azimuth resolution is made possible by matching the focus in transmission and reception. Moreover, dynamic depth focusing (hereinafter referred to as DDF) can obtain a plurality of reception focuses with respect to one transmission, which is similar to having focuses with different depths with respect to one virtual probe, and is therefore effective in achieving a speedup.

However, in either method, there is a limit to a speedup since the method performs (electronic) scanning while making each virtual probe transmit and receive ultrasonic waves. Furthermore, since a large aperture cannot be formed in the current virtual probe having about 16 to 32 channels, making it impossible to lengthen the focal length. Thus, there is a limit to flaw detection of a thick and large material being tested.

Unlike the above-described conventional flaw detection method by which electronic scanning is performed by using a phased array probe, volume focusing performs transmission with all the elements of an array probe at a time, then performs reception with all the elements, combines A scope waveforms of the elements, the A scope waveforms stored in a memory, and performs evaluation.

In the case of a linear probe, a transmitted wave propagates as a plane wave because it is emitted from a probe having a wide aperture. A reflection echo is amplified by an amplifier connected to all the elements and subjected to analog-to-digital conversion, and is then stored in the memory. In other words, the A scope waveforms of all the elements (for example, 128 elements) are stored in the memory in one transmission. This flaw detection waveform data is subjected to reception delay processing such as DDF on a set aperture-by-set aperture basis by signal processing performed by a high-speed DSP (Digital Signal Processor), and is evaluated. The above processing is performed at high speed, and more than one processing operation is performed simultaneously, whereby it is possible to achieve a further increase in the processing speed. When all the processes are finished, it becomes possible to perform the next transmission, and, if a ghost echo disappears during this time, the transmission can be performed. That is, it is possible to evaluate all the points in one cross section in one transmission without being affected by a ghost.

This is the reason why volume focusing is suitable for high-speed flaw detection.

For example, when internal flaw detection of a cross section of a rod-shaped material being tested is performed by disposing an array probe along the outer perimeter of the material being tested, the probe is made to perform scanning mechanically in an axial direction of the material being tested after the flaw detection of the cross section, whereby flaw detection of a cross section at another position in the axial direction is performed, and volume focusing is used in the above-described flaw detection of each cross section, it is possible to achieve a great reduction in flaw detection time at each position in the axial direction. This makes it possible to achieve a substantial reduction in the whole flaw detection time required for one rod.

In FIG. 19, a time chart of signal processing of volume focusing is shown.

T1 in FIG. 19 represents a transmitted wave of first ultrasonic waves, and T2 in FIG. 19 represents a transmitted wave of second ultrasonic waves. In both the first and second ultrasonic waves, S1 is a reflection echo reflected from the front surface of a material being tested, B1 is a reflection echo reflected from the bottom surface of the material being tested, and S2 is a reflection echo generated as a result of B1 being reflected again from the front surface of the material being tested. S2 to Sn are echoes called the ghost echoes described above.

By using FIGS. 20(A) and 20(B), a difference between zone focusing flaw detection and volume focusing flaw detection will be explained, taking up as an example flaw detection using a linear array probe having 128 elements.

Here, as conventional zone focusing flaw detection, a case where an array probe having 128 transducers is used and three strata are provided in a depth direction by performing simultaneous excitation of 32 elements is considered.

Specifically, each of the grids shown in an upper portion of FIG. 20(A) represents each of the elements of an array probe. An element represented by the grid on the extreme left is referred to as a first element, an element located next to the first element on the right is referred to as a second element, and an element next to the second element on the right is referred to as a third element. In this case, an element on the extreme right is a 128th transducer. Each element performs transmission and reception.

For each stratum to be subjected to flaw detection, first transmission and reception of the ultrasonic waves is performed by vibrating the first to 32nd elements, second transmission and reception of the ultrasonic waves is then performed by vibrating the second to 33rd elements, and third transmission and reception of the ultrasonic waves is then performed by vibrating the third to 34th elements. In this way, a group of 32 elements, which perform emission simultaneously, is shifted to the right, and the 126th to 128th elements are finally vibrated, whereby a total of transmission and reception operations are performed. Such operation is electronic scanning by the array probe.

In the above-described flaw detection, signals for exciting the 32 elements forming one transmission and reception group are delayed differently. Moreover, signals obtained by the vibration due to the reception performed by these 32 elements are also delayed individually. As a result of such delay processing performed on transmission and reception, the ultrasonic waves emitted from the 32 elements at a time are focused on one point.

Then, by setting the focus of the array to a position z-1 serving as a first stratum with respect to a depth direction of a material being tested, the above-described electronic scanning is performed in a direction of arrow in FIG. 20(A) (the depth direction of the material being tested is a vertical direction in FIG. 20(A), and the direction of arrow is a horizontal direction of the drawing as shown in the drawing). When the flaw detection at each position in the direction of arrow is finished in the above-described first stratum, the focus of the array is then set to a position z-2 serving as a second stratum which is deeper than the first stratum, and electronic scanning is performed in the direction of arrow in the same manner as described above. When the flaw detection in the second stratum is finished, the focus of the array is then set to a position z-3 serving as a third stratum which is deeper than the second stratum, and electronic scanning is performed in the direction of arrow in the same manner as described above.

As described above, in this example, in the zone focusing flaw detection, three electronic scanning operations are required.

Therefore, in this example, it is necessary to perform 97 scanning operations in the element direction and three scanning operations in the depth direction, and actual ultrasonic wave transmission and reception is performed 97×3=291 times.

On the other hand, in the volume focusing flaw detection, it is possible to perform flaw detection by performing DDF on the above-described three strata or more than three strata in one transmission and reception. For example, in FIG. 20(B), volume focusing processing by which DDF is performed on five strata is shown, and an increase in the number of strata subjected to DDF does not affect the PRF.

A specific explanation is described below.

In FIG. 20(B), a plurality of parallel vertical lines extending downward from the array probe represent plane waves of simultaneous excitation of all the channels, and dashed lines represent a focus beam at the time of reception. A black circle represents the focus on the receiving side. That is, in the volume focusing flaw detection, the above-described 128 elements emit ultrasonic waves simultaneously, and the focus is not obtained at the time of transmission, and the focus is virtually obtained by delay processing at the time of reception.

As shown by the above-described vertical lines in FIG. 20(B), by making all the elements emit ultrasonic waves simultaneously at a time as described above, an echo received by each element is delayed, whereby the focus is virtually created. As a result, for example, for the ultrasonic waves received by the first to 32nd elements, reception processing by which the six black circles on the extreme left in FIG. 20(B) are each set as the focus can be performed at a time, and, by the next reception processing, reception processing by which the six black circles next to the above six black circles on the right are each set as the focus can be performed at a time. Such reception processing is performed 97 times, whereby processing in each stratum in the depth direction can be finished.

As described above, in the volume focusing flaw detection shown in FIG. 20(B), unlike the zone focusing flaw detection shown in FIG. 20(A), there is no need for electronic scanning, and the result of focusing on each position in the depth direction can be obtained. Thus, by transmitting and receiving ultrasonic waves once, it is possible to perform flaw detection in a range that would require a plurality of electronic scanning operations in the zone focusing flaw detection.

When a rod-shaped material being tested is taken as an example, T2 in FIG. 19 described above represents a transmitted wave for flaw detection of the next cross section, the cross section located in a position different from the cross section subjected to flaw detection by emission of T1 with respect to the axial direction of the material being tested. On the other hand, in the zone focusing flaw detection of FIG. 20(A), T1 is, for example, a transmitted wave emitted for obtaining the first focus in the first strata, and T2 is a transmitted wave emitted for obtaining the next focus located next to the above focus in the first strata with respect to the electronic scanning direction.

In both the zone focusing flaw detection and the dynamic focusing flaw detection, between S1 and B1 (which in actuality is a position located rather on the right side of B1 and near B2) of FIG. 19, the presence or absence of a defective echo is checked. In volume focusing, between S1 and B1, A scope capture processing is performed (a peak waveform such as B2 appearing on the right side of B1 is unnecessary because it is generated by a ghost echo, and therefore is not captured).

However, in zone focusing, since T2 next to T1 is transmitted for the same cross section of the material being tested as the cross section to which T1 is transmitted, transmission of T2 cannot be performed until a ghost echo of T1 disappears.

The inventors tested how fast processing of the volume focusing flaw detection was as compared with zone focusing by using a prismatic aluminum test piece with a square cross-section. An artificial defect provided in this test piece is an SDH (Side Drill Hole) with a diameter of 0.5 mm. In both zone focusing and volume focusing, an array probe with 0.5 mm pitches and operating at 10 MHz was used. In the zone focusing method, scanning is performed in a depth direction in three stages of focal depth at 15-mm intervals and at a pitch of 0.5 mm in a longitudinal direction. To avoid a ghost, a PRF in each cycle was 2 KHz, and, overall, the PRF was 2000÷97÷3=6.8 Hz. On the other hand, in volume focusing, 128 elements were excited simultaneously, reception was performed by a focal row (a group having a specific focus and a specific angle) of 32 elements, 10-mm DDF was performed in a depth direction, and 0.5-mm pitch signal processing was performed. The repetition frequency of transmission at this time, that is, the PRF was 437 Hz, and this is 64-times speedup in flaw detection compared to the above flaw detection.

Moreover, zone focusing was confirmed to have an excellent resolution capability because zone focusing could narrow focus in both transmission and reception. On the other hand, volume focusing was confirmed to have the focus because the beam was not spread in the depth direction due to the effect of the DDF. In volume focusing, B scope of the flaw detection can be obtained by one transmission.

However, at present, there is no method by which flaw detection of an internal defect is performed by using volume focusing on a material being tested, the material, which is circular in cross section.

Through an intensive study in search of the possibility of using volume focusing for a material being tested, the material which is circular in cross section, the inventors have completed the present invention.

During their study, it has been found out that, when internal flaw detection is performed by making ultrasonic waves enter the material being tested by using volume focusing, the presence of a dead zone called a dead band, the dead zone in which flaw detection cannot be performed, becomes a factor that narrows a flaw detection range.

A specific description will be given below. As flaw detection using the above-described volume focusing, by disposing one array probe such that a plurality of transducers are arranged along the outer circumference of a cylindrical material being tested, the material having a circular cross-sectional shape, as seen in a sectional view, and emitting ultrasonic waves simultaneously from the transducers toward positions on an incident section which is a section on which the array probe is disposed with respect to the circumferential direction of the material being tested, the ultrasonic waves emitted from the transducers converge at the center or near the center of a circle exhibited by the material being tested, and the ultrasonic waves which diverged after converging reach a counter section facing the incident section on the outer circumference of the material being tested with the center of the circle placed therebetween. Thus, flaw detection of the entire fan-shaped area from the divergence of the ultrasonic waves to the counter section, as seen in a sectional view of the material being tested, may seem to be performed by one transmission of the ultrasonic waves.

However, in reality, due to a reflection echo (a front surface echo) generated on the above-described incident section, a region near the incident section in the material being tested is a dead zone (a dead band) in which it is difficult to detect a defective echo.

Furthermore, due to a reflection echo (a bottom surface echo) generated on the counter section facing the incident section, although the size is much smaller than that of the dead zone appearing on the incident section, a small dead zone also appears near the counter section in the material being tested. Moreover, even when such a dead band is ignored, an area on which flaw detection can be performed at a time by one array probe in which a plurality of transducers are arranged in an arc as seen in a sectional view as described above is limited to the above-described fan-shaped area from the divergence of the ultrasonic waves to the counter section, and a wide region on which flaw detection has not yet been performed remains in the material being tested. This makes it necessary to make time for performing extra flaw detection on the remaining wide region on which flaw detection has not yet been performed.

DISCLOSURE OF INVENTION

The present invention aims to prevent the occurrence of the above-described dead zone in a cylindrical material being tested, the material having a circular cross-sectional shape, while reducing flaw detection time by using volume focusing flaw detection.

A first aspect in accordance with the present invention provides ultrasonic flaw detection equipment using a volume focusing flaw detection method, the ultrasonic flaw detection equipment including: an array probe having a plurality of transducers which can be arranged along a surface of a material being tested; an exciting unit exciting each transducer of the array probe; a waveform memory storing an ultrasonic wave received echo received by each transducer as waveform data of each transducer; a phase combining unit reading the contents of the waveform memory in which the waveform data of each transducer is stored and performing phase combining; and a focusing unit providing, in reading from the waveform memory, an address of each waveform memory as an address corresponding to a beam path length of dynamic focusing for an arbitrary position in a pseudo electronic scanning range, the ultrasonic flaw detection equipment transmitting ultrasonic waves toward the material being tested from all the transducers of the array probe at a time, receiving reflection echoes thereof by all the transducers, combining A scope waveforms of elements, the A scope waveforms being stored in the waveform memory, by the phase combining unit, and performing evaluation, the ultrasonic flaw detection equipment described below.

That is, this equipment performs internal flaw detection of a material being tested, the material having a virtually circular cross-sectional shape, and includes two or more array probes. In a sectional view of the material being tested, that is, as seen from an axial direction of the material being tested, a plurality of transducers of each array probe are arranged in an arc along a circle exhibited by the material being tested. Array probes are disposed so as to surround the material being tested. The exciting unit enables flaw detection of the material being tested to be performed by a vertical flaw detection method and enables the array probes to perform flaw detection of the material being tested by an oblique flaw detection method by exciting the transducers while gradually shifting timing from one end of an arc exhibited by an array toward the other end of the arc. The exciting unit makes each array probe emit the ultrasonic waves by the vertical flaw detection method in such a way as to allow the ultrasonic waves to enter the material being tested from each position on an incident section which is a section on the circumference of the circle exhibited by the material being tested, the section along which the array is placed, as a result of the plurality of transducers being vibrated once, and makes the ultrasonic waves allowed to enter reach a counter section facing the incident section on the circumference of the circle exhibited by the material being tested, and the exciting unit makes each array probe emit the ultrasonic waves by the oblique flaw detection method in such a way as to allow the ultrasonic waves to enter the material being tested as a result of the plurality of transducers being vibrated once, and makes the ultrasonic waves allowed to enter reach one of adjacent sections adjacent to the counter section.

Incidentally, the adjacent section here is not limited to a section whose one end is in abutting contact or coincides with one end of the counter section, but includes a section whose end is away from the end of the counter section and a section which overlaps with the counter section. That is, the adjacent section here includes any section as long as an arc exhibited by the adjacent section faces in a different direction from an arc exhibited by the counter section on the circumference of the circle exhibited by the material being tested and the section is not completely included in the counter section as part of the counter section.

In a second aspect in accordance with the present invention, in the first aspect in accordance with the present invention, the volume focusing flaw detection method is used at least in the vertical flaw detection method, and the vertical flaw detection method excites the transducers of the array probe simultaneously, the transducers having at least a line-symmetric positional relation with respect to a perpendicular bisector of a line segment connecting the ends of an arc exhibited by the array probe in a cross section orthogonal to the axial direction of the material being tested, that is, as seen from the axial direction of the material being tested.

A third aspect in accordance with the present invention provides, in the first or second aspect in accordance with the present invention, the ultrasonic flaw detection equipment wherein the exciting unit sets an actual focus of the ultrasonic waves allowed to enter by the vertical flaw detection method on the bisector and between the incident section and the center of the circle exhibited by the material being tested in the cross section, and the exciting unit further sets an actual focus of the ultrasonic waves allowed to enter by the oblique flaw detection method inside the material being tested and in a position off the perpendicular bisector, the position closer to the array probe than a line which intersects the perpendicular bisector at a right angle at the center of the circle exhibited by the material being tested, in the cross section.

A fourth aspect in accordance with the present invention provides, in any one of the first to third aspects in accordance with the present invention, the ultrasonic flaw detection equipment having the following configuration.

That is, the pseudo electronic scanning is pseudo scanning performed on the receiving side in place of electronic scanning in which scanning is performed by sequentially exciting the arranged transducers of the array probe along a direction in which the transducers are arranged at the time of transmission of the ultrasonic waves, the pseudo scanning in which the arranged transducers are brought into correspondence with addresses of the waveform memories, data of received waves obtained by exciting all the arranged transducers of the array probe at one time at the time of transmission of ultrasonic waves is recorded on the waveform memories, and, in reading data from the waveform memory, data in the memory is read by sequentially shifting, in a direction corresponding to an electronic scanning direction of the transducer, the address of the memory corresponding to the transducer necessary to form a focus in each position inside the material being tested on the receiving side. In addition, in vertical flaw detection, during pseudo electronic scanning, a direction of an ultrasonic beam of each group of transducers to be shifted is brought into correspondence with each position in the counter section by providing a correction value to the address in reading from the waveform memory. In oblique flaw detection, during pseudo electronic scanning, a direction of an ultrasonic beam of each group of transducers to be shifted is brought into correspondence with each position in the adjacent section by providing another correction value to the address in reading from the waveform memory.

A fifth aspect in accordance with the present invention provides, in any one of the first to fourth aspects in accordance with the present invention, the ultrasonic flaw detection equipment adopting the following configuration.

That is, the correction value in the vertical flaw detection brings a beam of each of the transducers forming the same group into correspondence with one point on the counter section by providing thereto an angle of incidence set with consideration given to a corresponding one of angles of refraction which are different from each other at incident points of the transducers, so that the transducers of the group have the same beam path length, and forms dynamic focusing for the same group. The correction value in the oblique flaw detection brings at least a beam of each of the transducers forming the same group into correspondence with one point on the adjacent section by providing thereto an angle of incidence set with consideration given to a corresponding one of angles of refraction which are different from each other at incident points of the transducers, so that the transducers of the same group have the same beam path length.

A sixth aspect in accordance with the present invention provides, in any one of the first to fifth aspects in accordance with the present invention, the ultrasonic flaw detection equipment including a gate calculating unit, wherein, in oblique flaw detection, the gate calculating unit sets a flaw detection gate for each group of transducers to be shifted during pseudo electronic scanning, the flaw detection gate according to the distance between a transducer and an incident point of the ultrasonic waves from the transducer into the material being tested, with reference to surface waves obtained by transmission in vertical flaw detection.

A seventh aspect in accordance with the present invention provides ultrasonic flaw detection equipment adopting the following configuration.

That is, this equipment performs internal flaw detection of a material being tested, the material having a virtually circular cross-sectional shape, and includes a vertical flaw detection apparatus and an oblique flaw detection apparatus. The flaw detection apparatuses each include: an array probe having a plurality of transducers which can be arranged along a surface of the material being tested; an exciting unit exciting each transducer of the array probe; a waveform memory storing an ultrasonic wave received echo received by each transducer as waveform data of each transducer; a phase combining unit reading the contents of the waveform memory in which the waveform data of each transducer is stored and performing phase combining; and a focusing unit providing, in reading from the waveform memory, an address of each waveform memory as an address corresponding to a beam path length of dynamic focusing for an arbitrary position in a pseudo electronic scanning range, and the flaw detection apparatuses each transmit ultrasonic waves toward the material being tested from all the transducers of the array probe at a time, receive reflection echoes thereof by all the transducers, combine A scope waveforms of elements, the A scope waveforms being stored in the waveform memory, by the phase combining unit, and perform evaluation. The array probes of the flaw detection apparatuses have a plurality of transducers arranged along the circumference of a circle exhibited by the material being tested as seen in a sectional view of the material being tested. The exciting unit of at least the vertical flaw detection apparatus makes each array probe emit the ultrasonic waves in such a way as to allow the ultrasonic waves to enter the material being tested from each position on an incident section which is each arc portion of the circumference of a circle of the material being tested, the arc portion along which the array is placed, as a result of the plurality of transducers being vibrated once, and makes the ultrasonic waves which diverged after converging in the material being tested reach a counter section facing the incident section on the circumference of the circle exhibited by the material being tested. The exciting unit of at least the oblique flaw detection apparatus makes the ultrasonic waves enter the material being tested obliquely as a result of the plurality of transducers being vibrated once by exciting the transducers while gradually shifting timing from one end of an arc exhibited by an array toward the other end of the arc, and makes the ultrasonic waves which diverged after converging in the material being tested reach an adjacent section adjacent to the counter section on the circumference of the circle exhibited by the material being tested. The vertical flaw detection apparatus and the oblique flaw detection apparatus each include a reception angle correcting unit. The reception angle correcting unit of the vertical flaw detection apparatus brings a direction in which each group of transducers to be shifted during pseudo electronic scanning emits ultrasonic waves into correspondence with each position in the counter section by providing a correction value to the address in reading from the waveform memory. The reception angle correcting unit of the oblique flaw detection apparatus brings a direction in which each group of transducers to be shifted during pseudo electronic scanning emits ultrasonic waves into correspondence with each position in the adjacent section by providing another correction value to the address in reading from the waveform memory.

An eighth aspect in accordance with the present invention provides, in the seventh aspect in accordance with the present invention, the ultrasonic flaw detection equipment wherein the oblique flaw detection apparatus doubles as the vertical flaw detection apparatus, and the oblique flaw detection apparatus can perform the vertical flaw detection and the oblique flaw detection by making the exciting unit excite the transducers at least two times.

A ninth aspect in accordance with the present invention provides, in the seventh or eighth aspect in accordance with the present invention, the ultrasonic flaw detection equipment adopting the following configuration.

That is, the correction value provided by the reception angle correcting unit forms a delay pattern bringing a beam of each of the transducers forming the same group into correspondence with one point on the counter section in the vertical flaw detection apparatus and with one point on the adjacent section in the oblique flaw detection apparatus by providing thereto an angle of incidence set with consideration given to a corresponding one of angles of refraction which are different from each other at incident points of the transducers, so that the transducers of the group have the same beam path length.

A tenth aspect in accordance with the present invention provides, in any one of the seventh to ninth aspects in accordance with the present invention, the ultrasonic flaw detection equipment adopting the following configuration.

That is, the focusing unit includes a Y direction counter indicating a pseudo electronic scanning position y, a D depth direction counter indicating a depth position of focus, and a dynamic focusing phase correction memory in which the amount of phase correction at each focus position in a dynamic focusing method is stored, and, by providing data of the Y direction counter and the D depth direction counter to an address of the dynamic focusing phase correction memory, the amount of phase correction at a focus position is obtained. The reception angle correcting unit adds a delay pattern of the amount of correction with respect to the angle of incidence to the data of the counters, the data to be provided to the address of the dynamic focusing phase correction memory.

An eleventh aspect in accordance with the present invention provides, in the tenth aspect in accordance with the present invention, the ultrasonic flaw detection equipment wherein the reception angle correcting unit includes a reception delay pattern holding section and a receiving-side selection holding section, the reception delay pattern holding section holds a delay pattern of the amount of correction according to the angle of incidence, and the receiving-side selection holding section identifies a corresponding delay pattern in the reception delay pattern holding section by the selection of the angle of incidence.

A twelfth aspect in accordance with the present invention provides an ultrasonic flaw detection method based on a volume focusing flaw detection method, the ultrasonic flaw detection method using: an array probe having a plurality of transducers which can be arranged along a surface of a material being tested; an exciting unit exciting each transducer of the array probe; a waveform memory storing an ultrasonic wave received echo received by each transducer as waveform data of each transducer; and a phase combining unit reading the contents of the waveform memory in which the waveform data of each transducer is stored and performing phase combining, the ultrasonic flaw detection method in which ultrasonic waves are transmitted toward the material being tested from all the transducers of the array probe at a time, reflection echoes thereof are received by all the transducers, A scope waveforms of elements, the A scope waveforms being stored in the waveform memory, are combined by the phase combining unit, and evaluation is performed, the ultrasonic flaw detection method adopting the following configuration.

That is, this method performs internal flaw detection of a material being tested, the material having a virtually circular cross-sectional shape, prepares two or more array probes, arranges, in a sectional view of the material being tested, a plurality of transducers of each array probe along the circumference of a circle exhibited by the material being tested, and makes the exciting unit perform flaw detection of the material being tested by a vertical flaw detection method and perform flaw detection of the material being tested by an oblique flaw detection method by exciting the transducers of each array probe while gradually shifting timing from one end of an arc exhibited by an array toward the other end of the arc. This method uses the exciting unit to make each array probe emit the ultrasonic waves by the vertical flaw detection method in such a way as to allow the ultrasonic waves to enter the material being tested from each position on an incident section which is a section on the circumference of the circle exhibited by the material being tested, the section along which the array is placed, as a result of the plurality of transducers being vibrated once, and make the ultrasonic waves allowed to enter reach a counter section facing the incident section on the circumference of the circle exhibited by the material being tested, and this method uses the exciting unit to make each array probe emit the ultrasonic waves by the oblique flaw detection method in such a way as to allow the ultrasonic waves to enter the material being tested as a result of at least a continuous part of the plurality of transducers of the array probe being vibrated once, and make the ultrasonic waves allowed to enter reach one of adjacent sections adjacent to the counter section on the circumference of the circle exhibited by the material being tested.

A thirteenth aspect in accordance with the present invention provides, in the twelfth aspect in accordance with the present invention, the ultrasonic flaw detection method wherein, after the flaw detection, by making the array probe perform scanning physically along an axial direction of the material being tested, the flaw detection is performed in another position in the axial direction.

A fourteenth aspect in accordance with the present invention provides, in the twelfth or thirteenth aspect in accordance with the present invention, the ultrasonic flaw detection method wherein, instead of preparing a test piece for each diameter of the material being tested to be subjected to flaw detection, the test piece being used in performing calibration, part of test pieces is complemented by using data on calibration performed on a test piece having a diameter greater than the diameter of the part of test pieces and data on calibration performed on a test piece having a diameter smaller than the diameter of the part of test pieces.

By the first to fourteenth aspects of the present invention, flaw detection of a cylindrical material being tested, such as a round bar, by the volume focusing method is realized, and it becomes possible to perform flaw detection of such a cylindrical material being tested, the material having a virtually circular cross-sectional shape, at high speed.

In particular, by performing the oblique flaw detection method in conjunction with the vertical flaw detection method based on volume focusing, it becomes possible to perform flaw detection with reliability on a region that cannot be covered only by the conventional vertical flaw detection method based on volume focusing. This helps reduce dead zones in which it is difficult to detect a defect.

In general, vertical flaw detection means making the ultrasonic waves emitted from a single probe enter the material being tested perpendicularly, and oblique flaw detection means making the ultrasonic waves emitted from a single probe enter the material being tested obliquely. However, as for the ultrasonic waves formed by exciting a plurality of arranged transducers of the array probe, hereinafter, flaw detection by the volume focusing method, the flaw detection performed by making the ultrasonic waves reach the counter section from the incident section on the outer circumference of the material being tested by making the transducers emit the ultrasonic waves with the same timing, the transducers disposed at line symmetric positions with respect to a perpendicular bisector of a line connecting the ends of a group of transducers arranged in an arc, is referred to as vertical flaw detection in the volume focusing method, and flaw detection by the volume focusing method, the flaw detection performed by making the ultrasonic waves reach the adjacent section on the outer circumference of the material being tested by gradually shifting ultrasonic wave emission timing of the transducers from one end of a group of transducers arranged in an arc toward the other end thereof, is referred to as oblique flaw detection in the volume focusing method. Hereinafter, unless otherwise noted, what is referred to simply as vertical flaw detection refers to the vertical flaw detection by the volume focusing method, and what is referred to simply as oblique flaw detection refers to the oblique flaw detection by the volume focusing method.

In particular, a dead band in vertical flaw detection performed by one array probe can be covered by vertical and oblique flaw detection performed by other probes.

Specifically, a dead band produced by surface waves generated by reflection which occurs at the surface of the material being tested when the ultrasonic waves enter the material being tested in vertical flaw detection performed by one probe is covered by vertical flaw detection performed by other probes, and a dead band produced by bottom waves generated by reflection which occurs at the counter section after the ultrasonic waves enter the material being tested in vertical flaw detection performed by one probe is covered by oblique flaw detection performed by other probes. At the same time, by making the individual probes perform both the vertical flaw detection and the oblique flaw detection as described above, it is possible to ensure a wide flaw detection range of one probe and reduce the number of probes. This offers cost advantage. Furthermore, one array probe can perform vertical flaw detection and oblique flaw detection (in two directions toward the adjacent sections on both sides of the counter section) by transmission performed three times. In this regard, it is possible to ensure a wider flaw detection range that can be covered by one probe and perform high-accuracy flaw detection.

As described above, in the present invention, flaw detection can be performed at high speed by using a volume focusing technique.

In particular, according to the third aspect of the present invention, by setting the focuses in the vertical flaw detection and the oblique flaw detection in positions closer to the probe than a line which intersects a perpendicular bisector of a line segment connecting the ends of an arc exhibited by an array at a right angle at the core (the center of the circle exhibited by the material being tested as seen in a sectional view) of the material being tested, it is possible to diverge the ultrasonic waves widely toward the counter section and the adjacent section after the ultrasonic waves converge. This make it possible to ensure a wide flaw detection range covered by one array as compared with when the focus is obtained on the core of the material being tested or on the line which intersects the perpendicular bisector at a right angle at the core of the material being tested.

In the fourth aspect of the present invention, unlike electronic scanning performed in transmission and reception by the conventional array probe, ultrasonic waves are transmitted toward a flaw detection range at a time without performing electronic scanning on the transmitting side, and scanning for reading from the memory corresponding to the transducer, the scanning performed in reading a waveform received on the receiving side from the memory, is performed as pseudo electronic scanning. In particular, by using pseudo electronic scanning as scanning on the receiving side for obtaining volume focusing and sequentially shifting the addresses of the memories necessary to obtain individual dynamic focusing in a Y direction corresponding to a direction in which the transducers are arranged, in order to obtain all the dynamic focusing in the positions in a direction (aY direction) in which the addresses of the memories are placed, the direction corresponding to the direction in which the transducers are arranged, it is possible to make use of the effect of reducing the flaw detection time, the effect produced by reception processing by volume focusing.

Moreover, by the fourteenth aspect of the present invention, it is possible to perform calibration with a small number of test pieces by complementing a material being tested, the material having a size for which no test piece is prepared, by using actual data on the existing test pieces. For example, based on the data of calibration actually performed on the existing test pieces having a diameter of 50 mm and a diameter of 60 mm, a material being tested having a diameter of 55 mm is complemented by using the data on the 50-mm and 60-mm test pieces without performing actual calibration on the material being tested having a diameter of 55 mm. In this way, it is possible to dispense with the preparation of 55-mm test piece.

In particular, by using the volume focusing method, the equipment and the method make all the transducers emit the ultrasonic waves at a time at the time of actual transmission of the ultrasonic waves instead of setting a focus in a region on which flaw detection is to be performed (a region to be subjected to flaw detection) and make the ultrasonic waves temporarily converge on this side of the region to be subjected to flaw detection (in a position closer to the array probe), whereby it is possible to diverge the ultrasonic waves widely toward the region to be subjected to flaw detection after the ultrasonic waves converge. Therefore, it is possible to ensure a wide flaw detection region for a material being tested by emitting the ultrasonic waves once.

Specifically, when an inside region of a material being tested located on the side opposite to the probe with respect to the core (the center of a circle exhibited by the material being tested as seen in a sectional view) of the material being tested, the material having a virtually circular cross-sectional shape, is set as a flaw detection region, by making the ultrasonic waves actually focus at the time of transmission in a region closer to the probe than the core of the material being tested, the ultrasonic waves which has passed through the focus diverge as cylindrical waves as seen in a sectional view (hereinafter referred to as cylindrical waves if necessary), making it possible to cover the region to be subjected to flaw detection widely.

In the past, a focus has been placed in a region of a material being tested, the region to be subjected to flaw detection, to ensure the intensity of a defective echo reflected from a defect and obtain an echo with good S/N. In the present invention, as described above, the cylindrical waves generated by the divergence after convergence are made to spread widely in the region to be subjected to flaw detection without setting a focus in the region to be subjected to flaw detection.

In the above description, a reflected echo from a reflection source in the test range is received by each transducer of an ultrasonic transducer array (an array probe), and is stored in each waveform memory as waveform data. In the waveform memory, as the waveform data, information on the position of a defect (an ultrasonic wave reflection source) in the entire test range and the size thereof (the amount of reflection) is stored after being subjected to phase diffusion. That is, as a result of the ultrasonic waves being transmitted once and then being received, the defect distribution status in the entire testing space is subjected to phase diffusion and is then stored in the waveform memory. With a means of performing high-speed inverse operation on the defect distribution status at an arbitrary position in the testing space, it is possible to synthesize the defect distribution status in the entire testing space repeatedly based on the contents of the waveform memory, the contents stored therein after being subjected to phase diffusion. This helps reduce the testing time dramatically and increase the testing speed. This is made possible by the focusing unit providing an address of each waveform memory as an address corresponding to a beam path length of dynamic focusing for an arbitrary position in a pseudo electronic scanning range and the phase combining unit reading the contents of each waveform memory and performing phase combining by an adder.

BRIEF DESCRIPTION OF DRAWINGS

[FIG. 15] It is a schematic longitudinal sectional view showing pseudo electronic scanning in oblique flaw detection of the embodiment of the invention.

[FIG. 20] FIG. 20(A) is an explanatory diagram of zone focusing flaw detection, and FIG. 20(B) is an explanatory diagram of volume focusing flaw detection.

[FIG. 21] FIGS. 21(A) and 21(B) are explanatory diagrams showing the flaw detection results obtained by the equipment of the invention.

BEST MODE FOR CARRYING OUT THE INVENTION

Hereinafter, an embodiment of the invention will be described based on the drawings.

The embodiment of the invention is shown in FIGS. 1 to 18.

Figure 1:
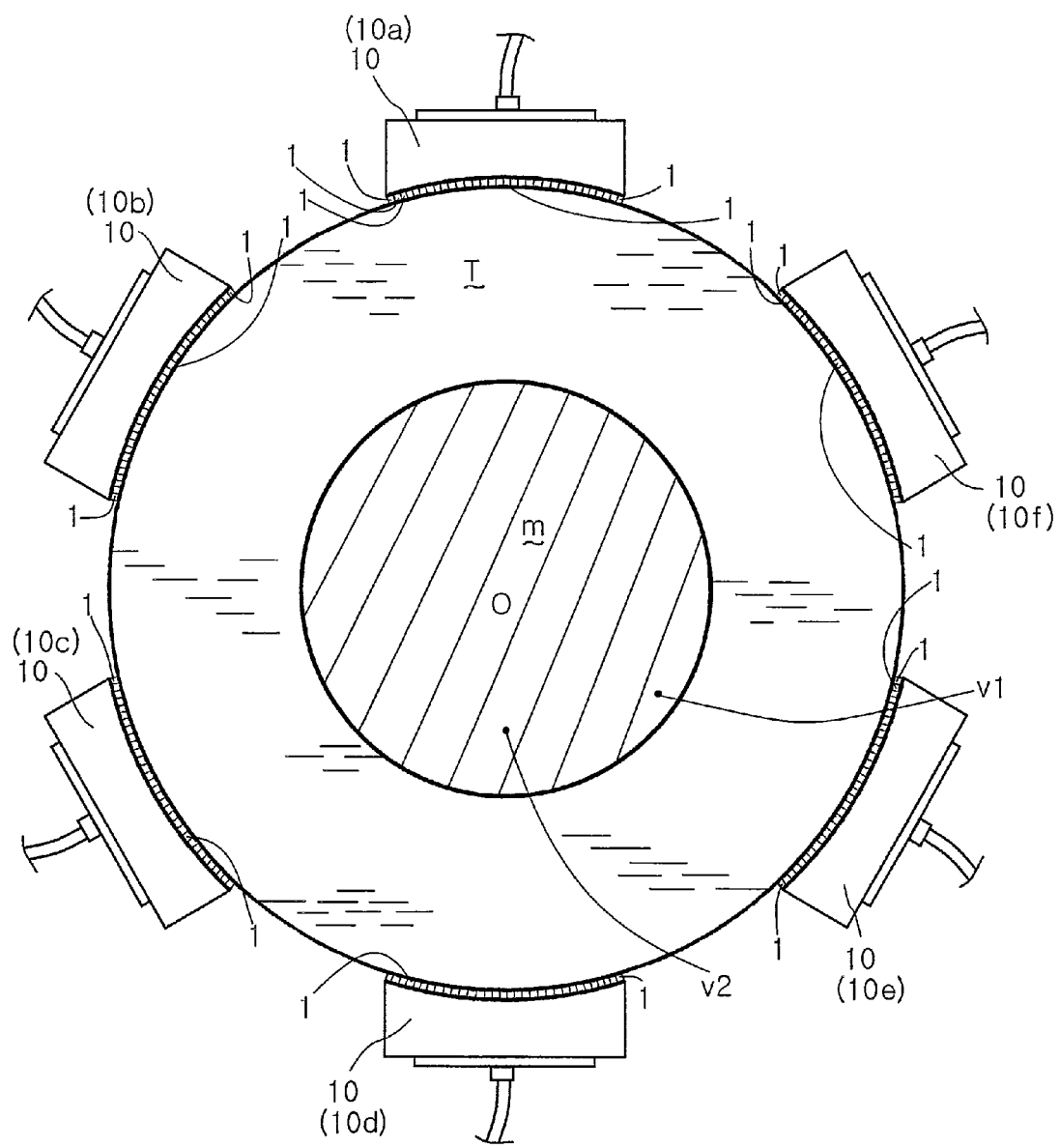
[FIG. 1] It is a schematic sectional view showing the placement of array probes of equipment in accordance with an embodiment of the invention.
Figure 2:
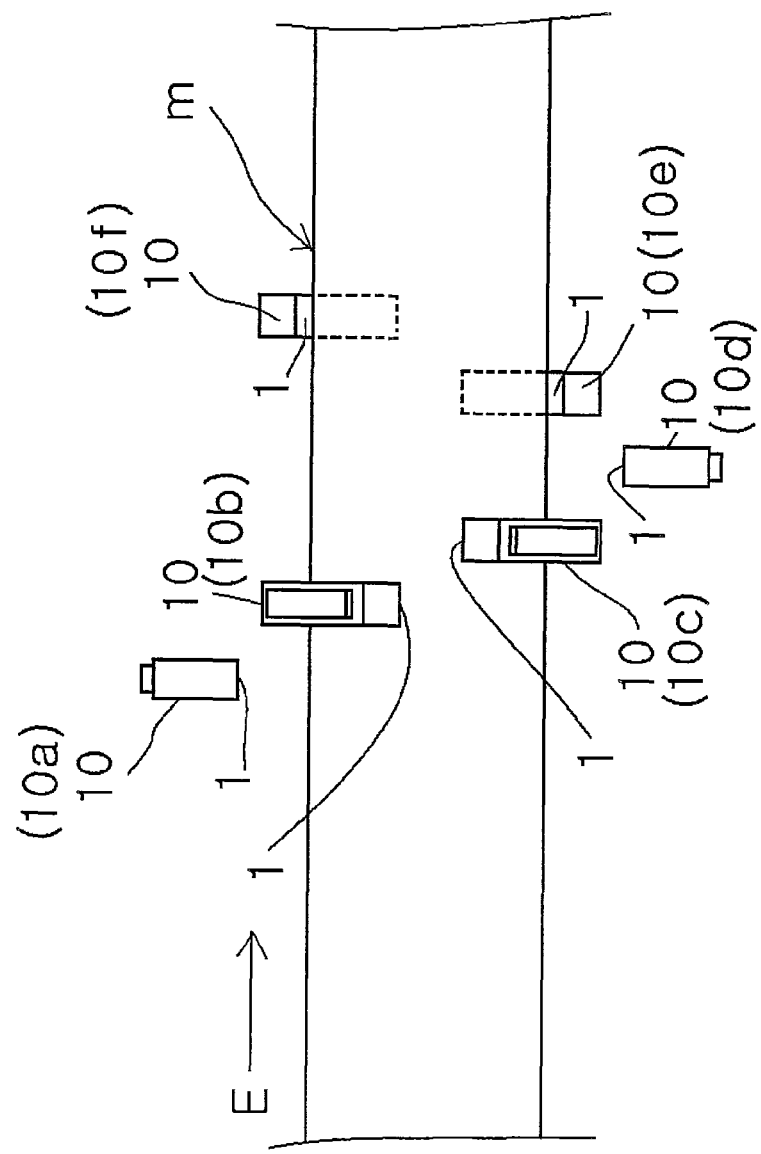
[FIG. 2] It is a schematic side view showing the above placement.
Figure 3:
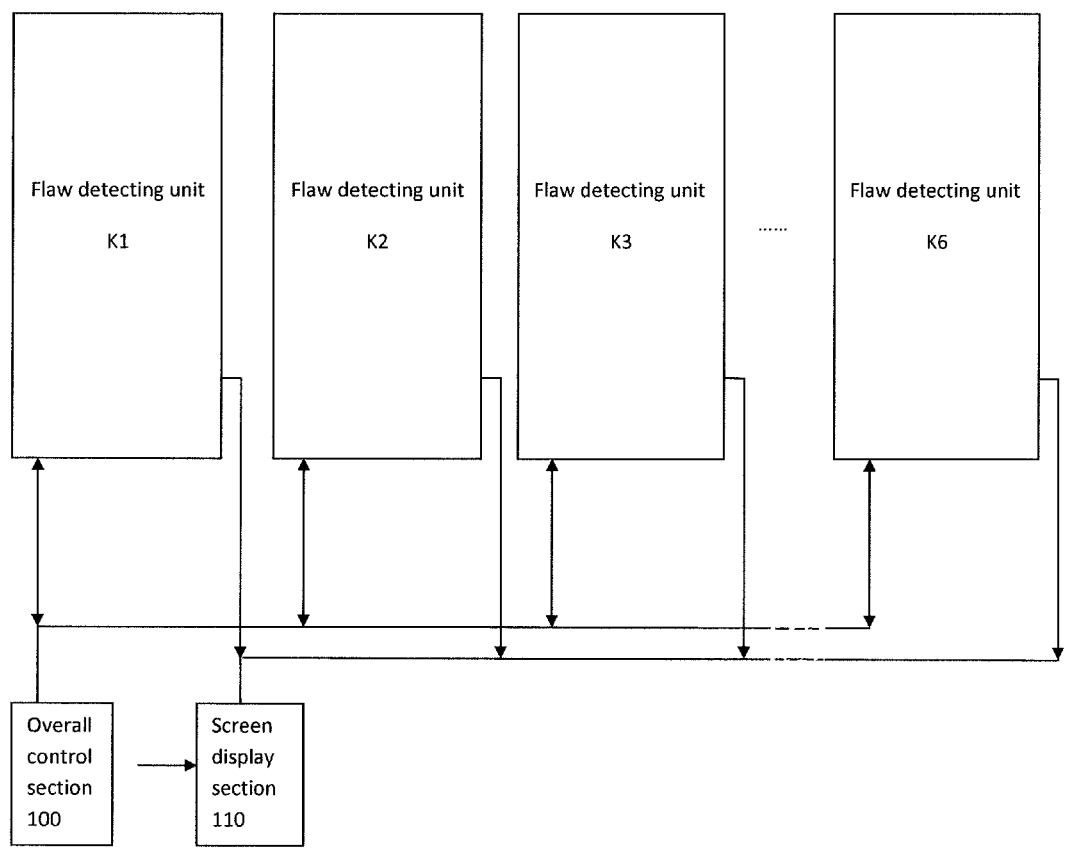
[FIG. 3] It is a block diagram showing an outline of the above equipment.
Figure 4:
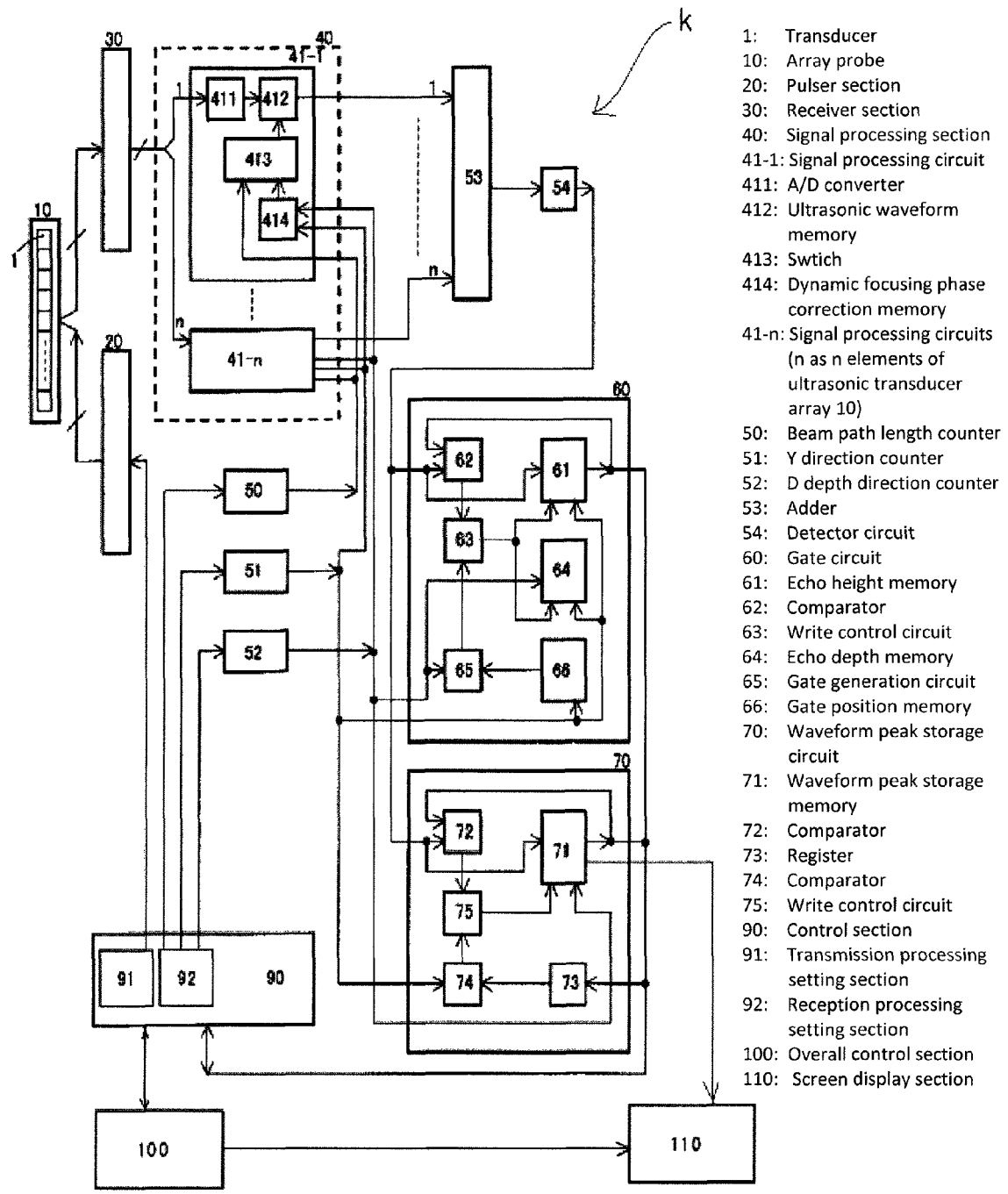
[FIG. 4] It is a block diagram of an enlarged principal portion of the block diagram of FIG. 3.
Figure 5:
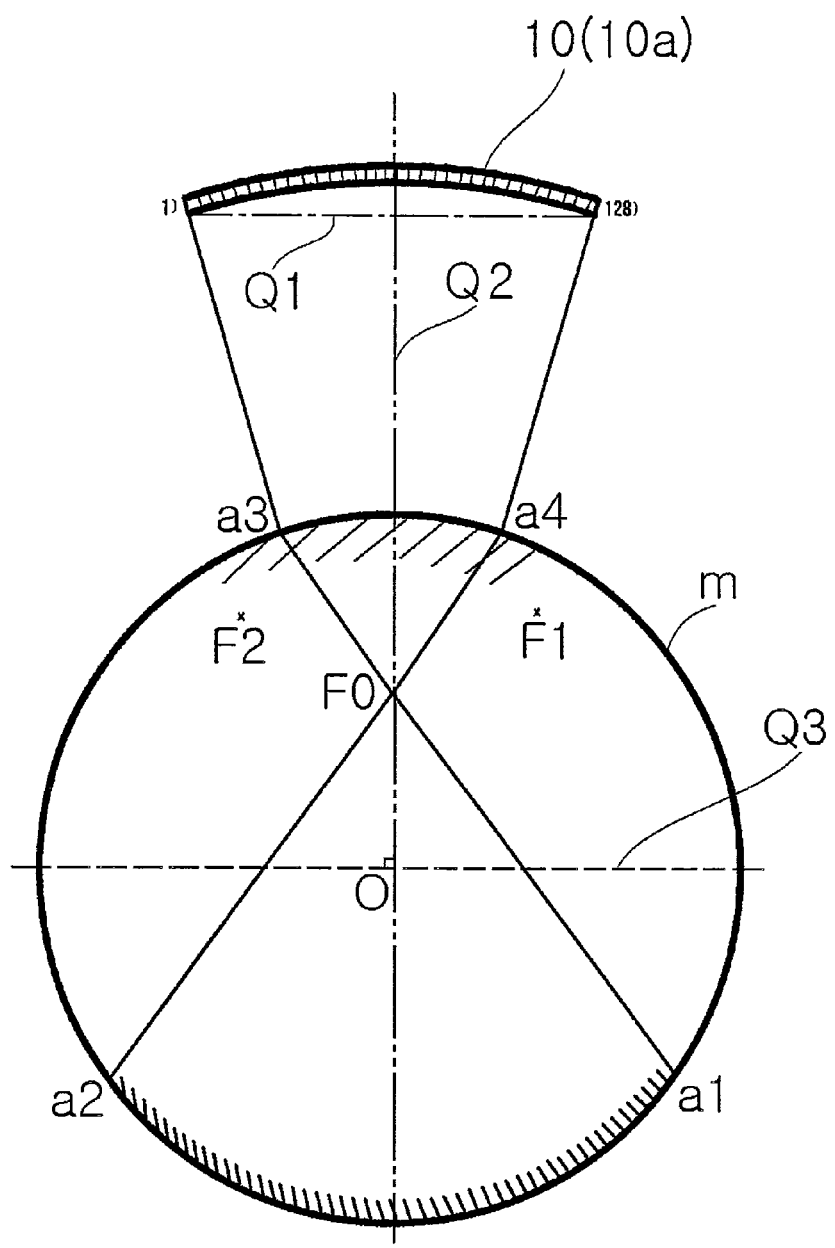
[FIG. 5] It is a schematic sectional view showing a focus position of ultrasonic waves emitted from one array probe of the above equipment toward a material being tested.
Figure 6:
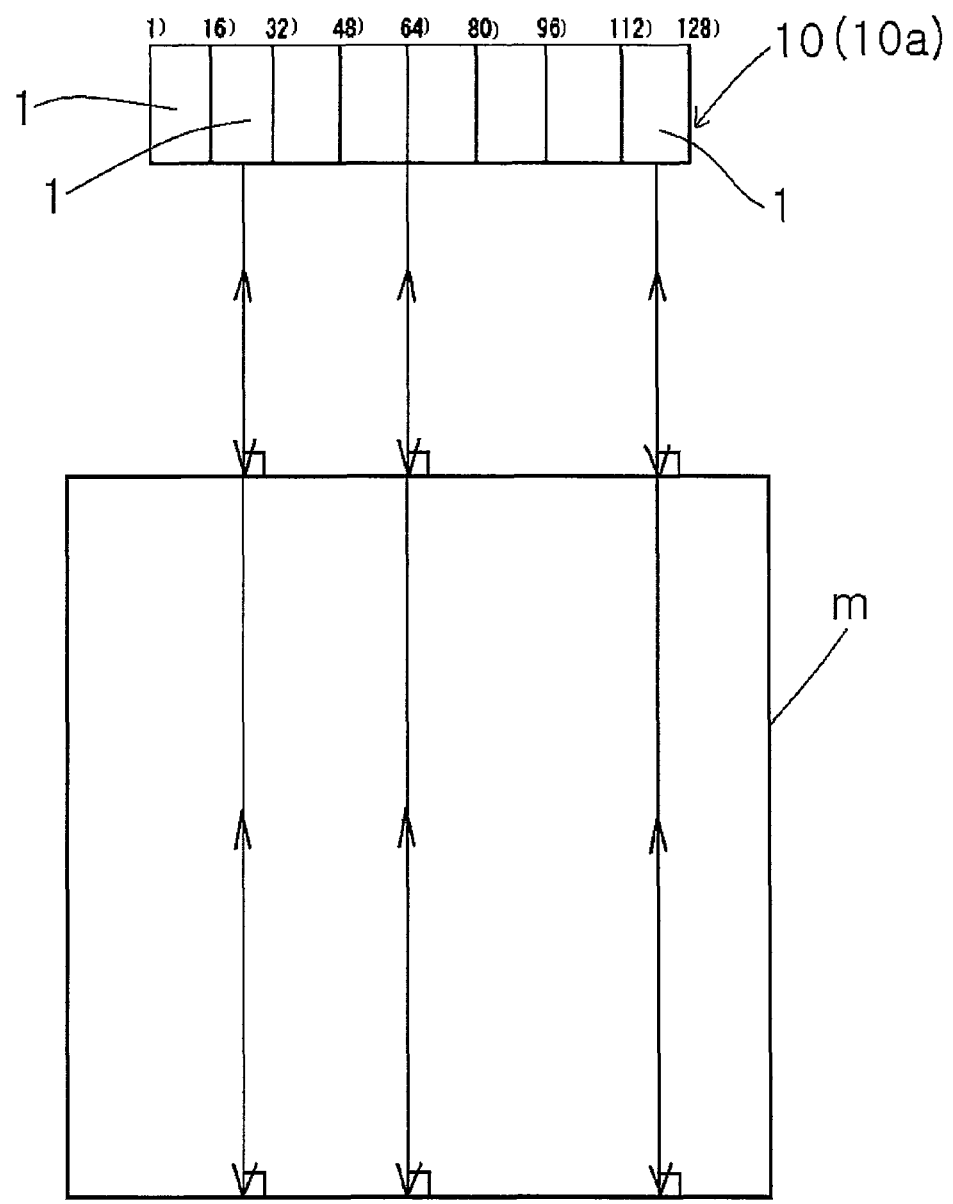
[FIG. 6] It is a schematic longitudinal sectional view explaining a plane wave in volume focusing in which a test object is a square billet.
Figure 7:
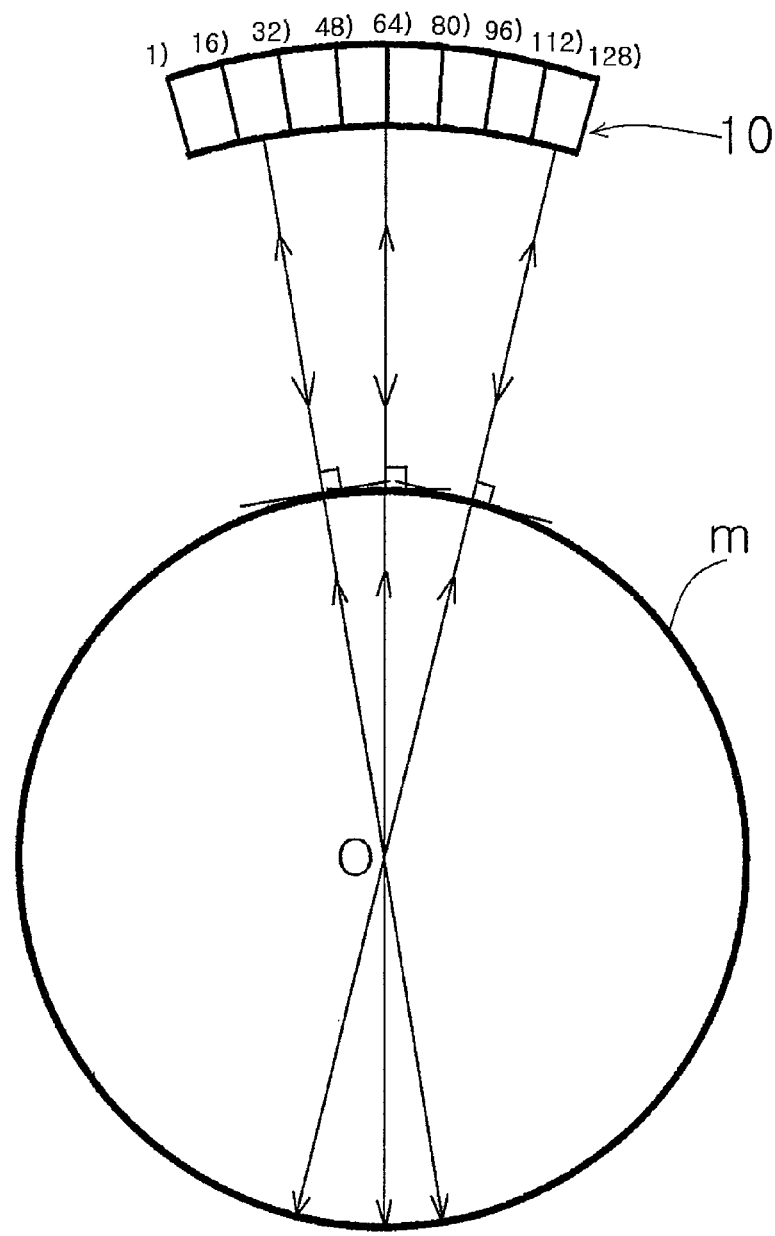
[FIG. 7] It is a schematic longitudinal sectional view explaining volume focusing in the invention in which a test object is a round rod (a cylindrical material).
Figure 8:
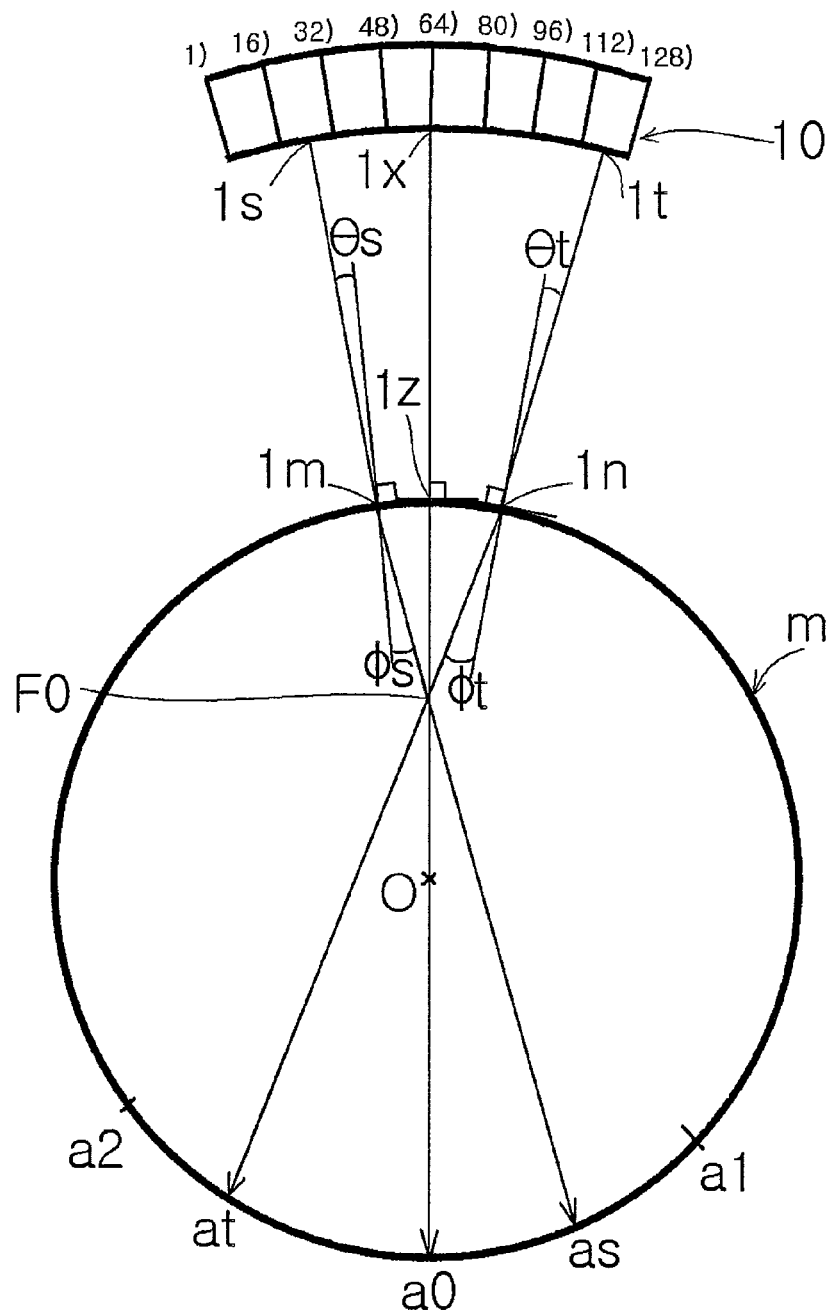
[FIG. 8] It is a schematic longitudinal sectional view showing how to set a correction value in vertical flaw detection of the embodiment of the invention.
Figure 9:
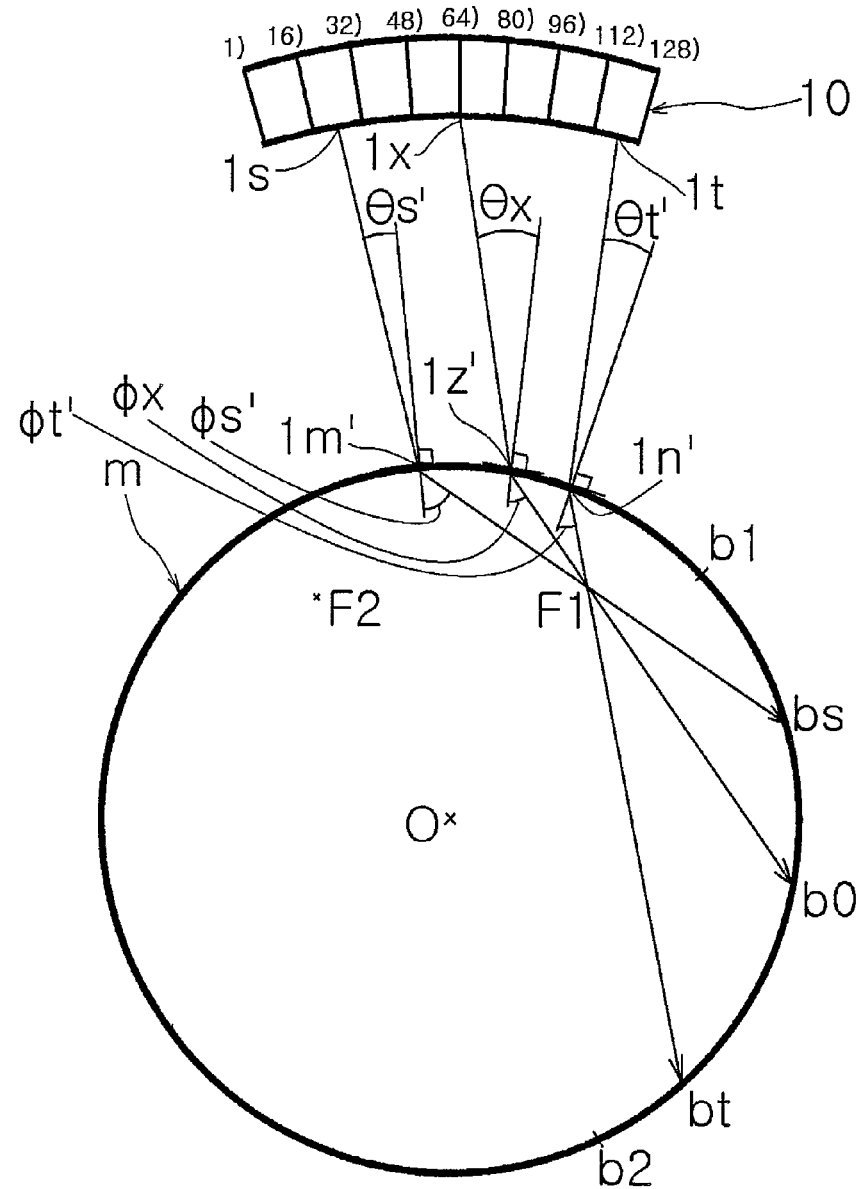
[FIG. 9] It is a schematic longitudinal sectional view showing how to set a correction value in oblique flaw detection of the embodiment of the invention.
Figure 10:
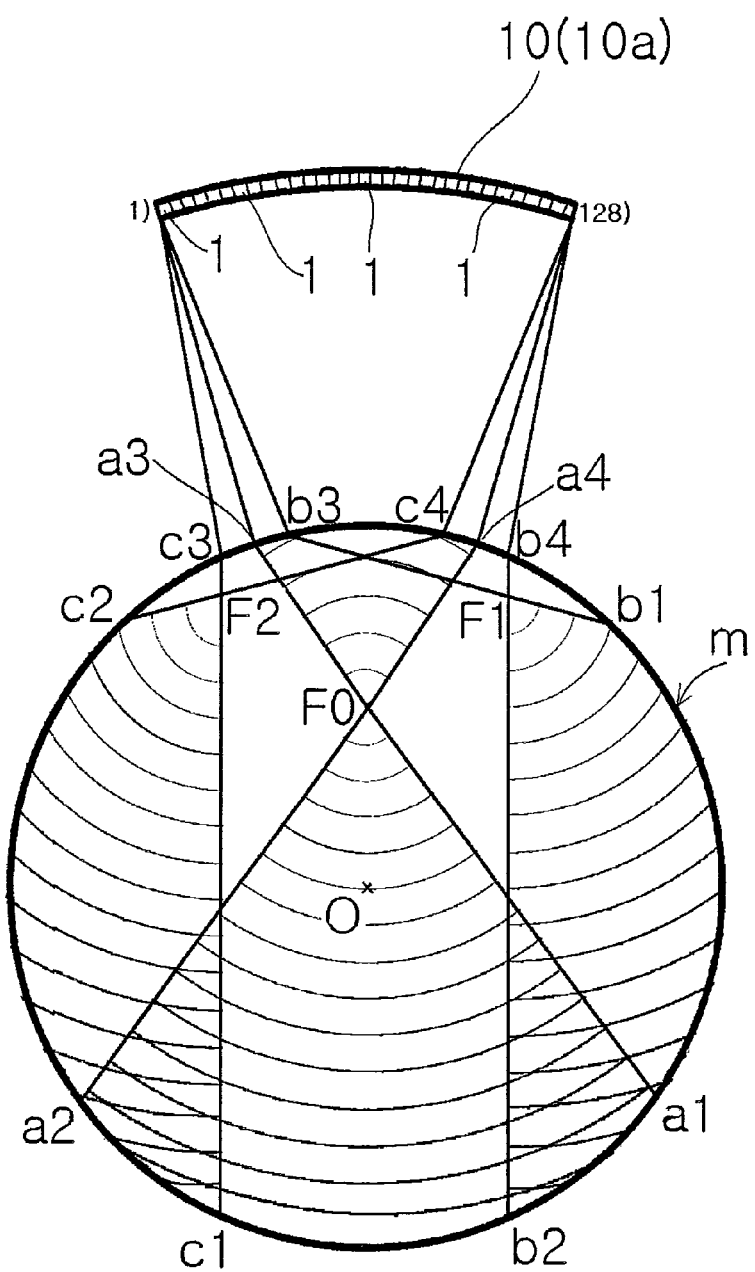
[FIG. 10] It is a schematic longitudinal sectional view showing the range of propagation of ultrasonic waves in vertical and oblique flaw detection of the embodiment of the invention.
Figure 11:
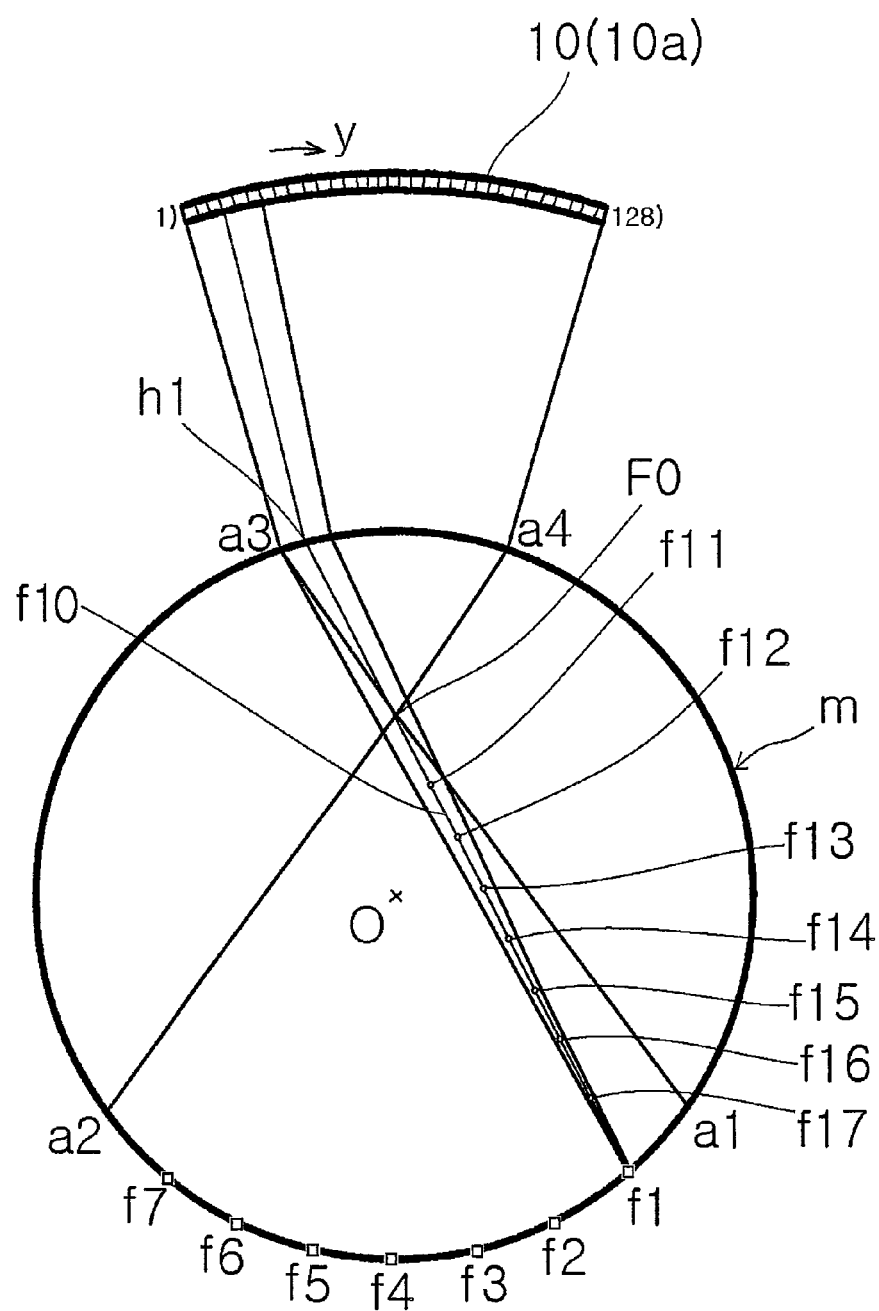
[FIG. 11] It is a schematic longitudinal sectional view showing pseudo electronic scanning in vertical flaw detection of the embodiment of the invention.
Figure 12:
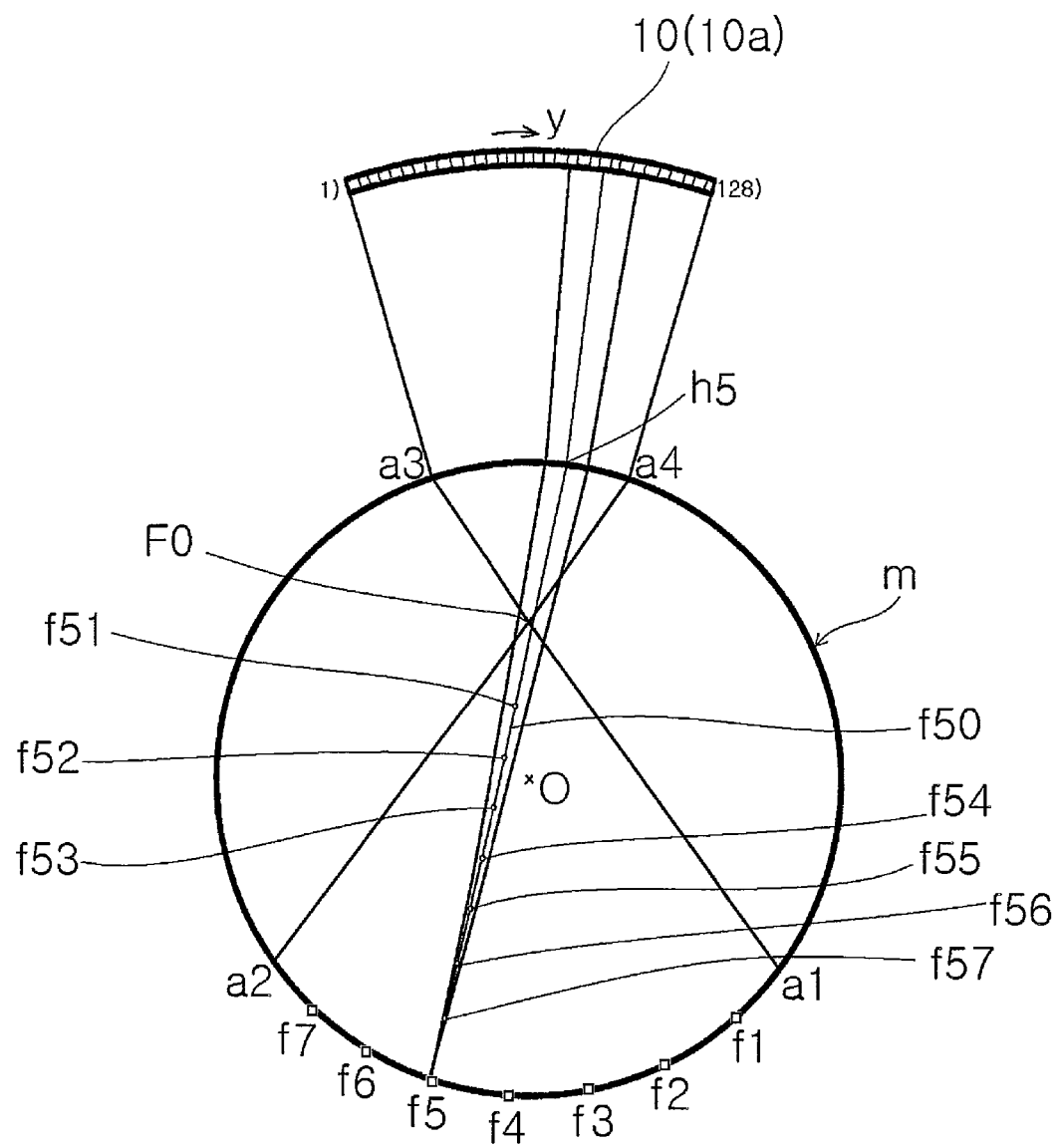
[FIG. 12] It is a schematic longitudinal sectional view showing pseudo electronic scanning in vertical flaw detection of the embodiment of the invention.
Figure 13:
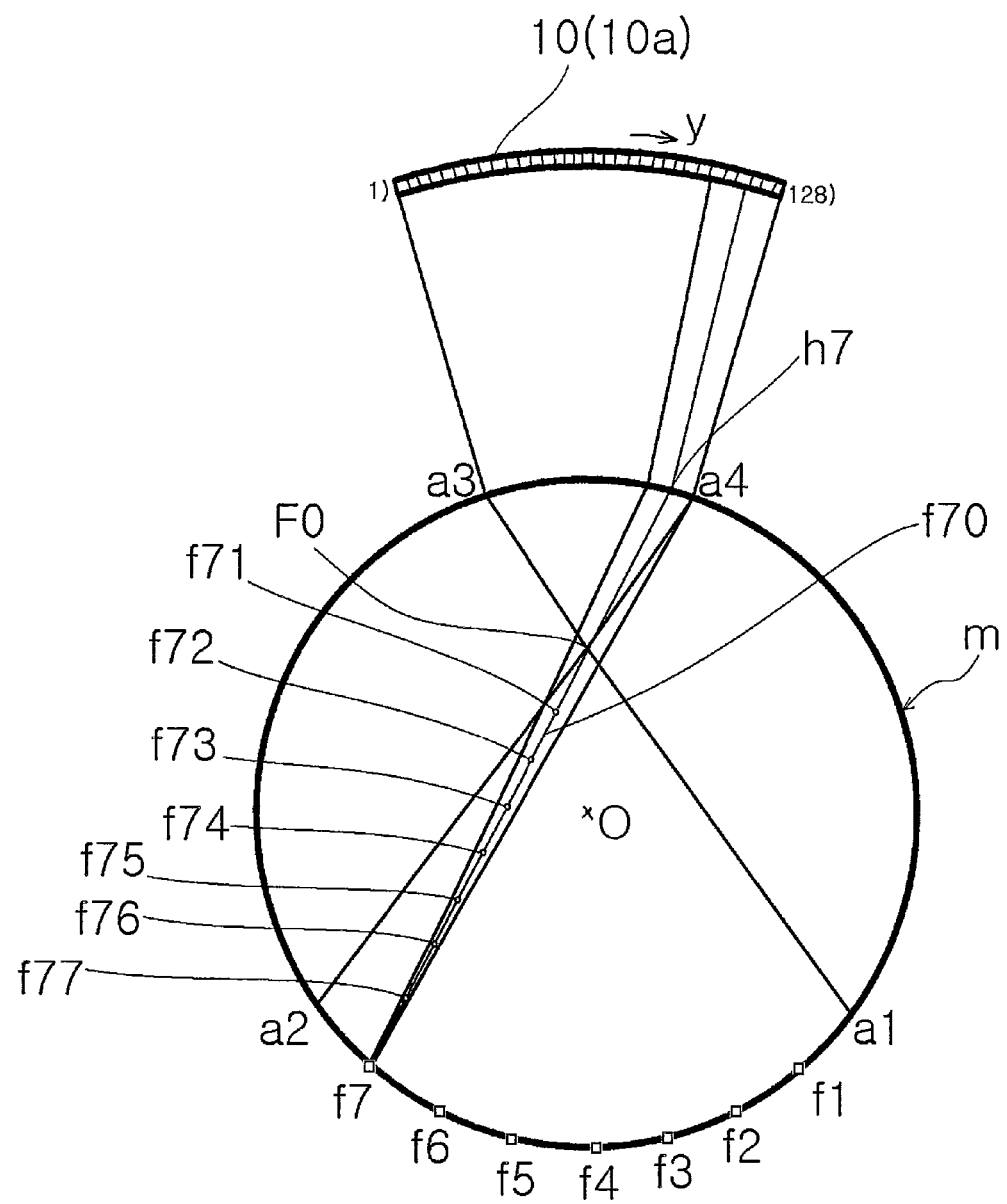
[FIG. 13] It is a schematic longitudinal sectional view showing pseudo electronic scanning in vertical flaw detection of the embodiment of the invention.
Figure 14:
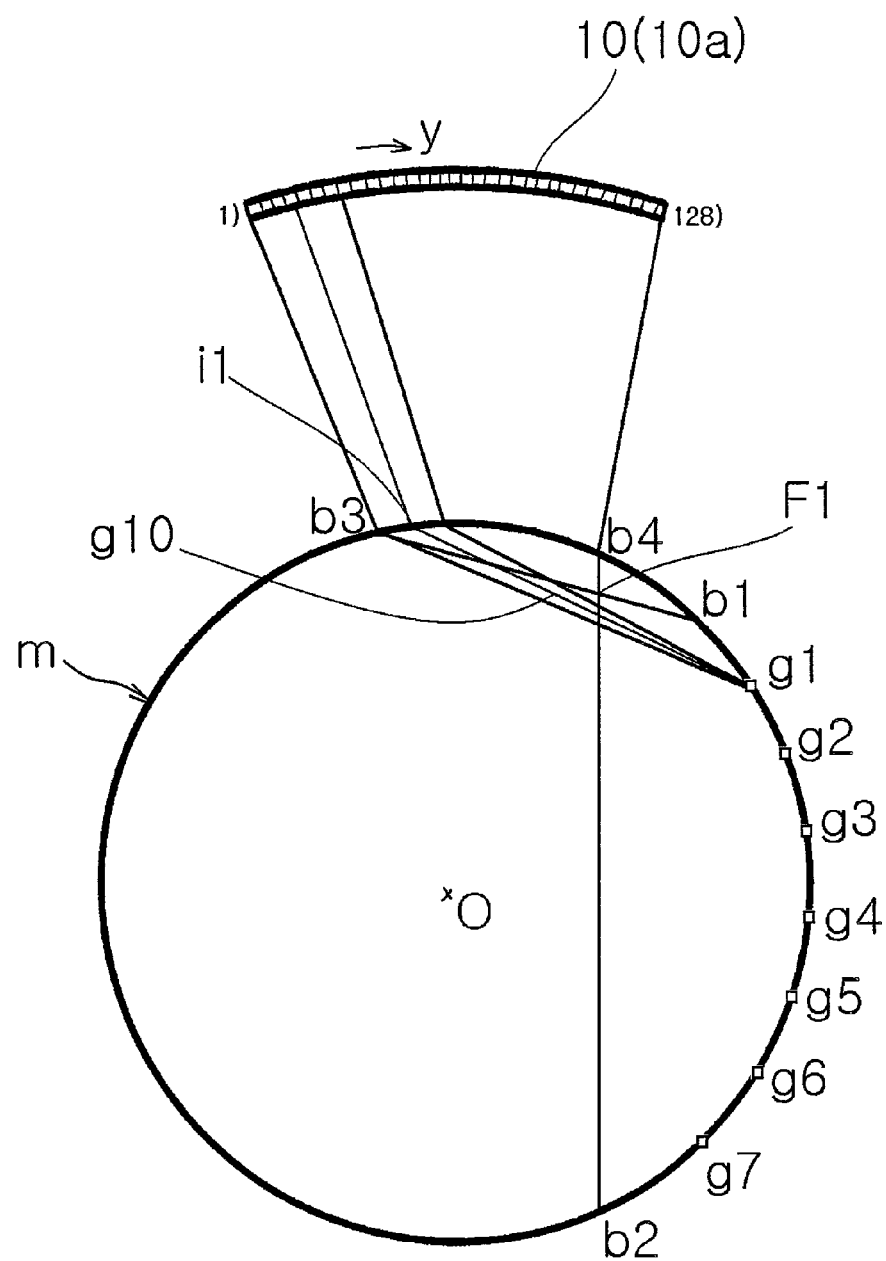
[FIG. 14] It is a schematic longitudinal sectional view showing pseudo electronic scanning in oblique flaw detection of the embodiment of the invention.
Figure 16:
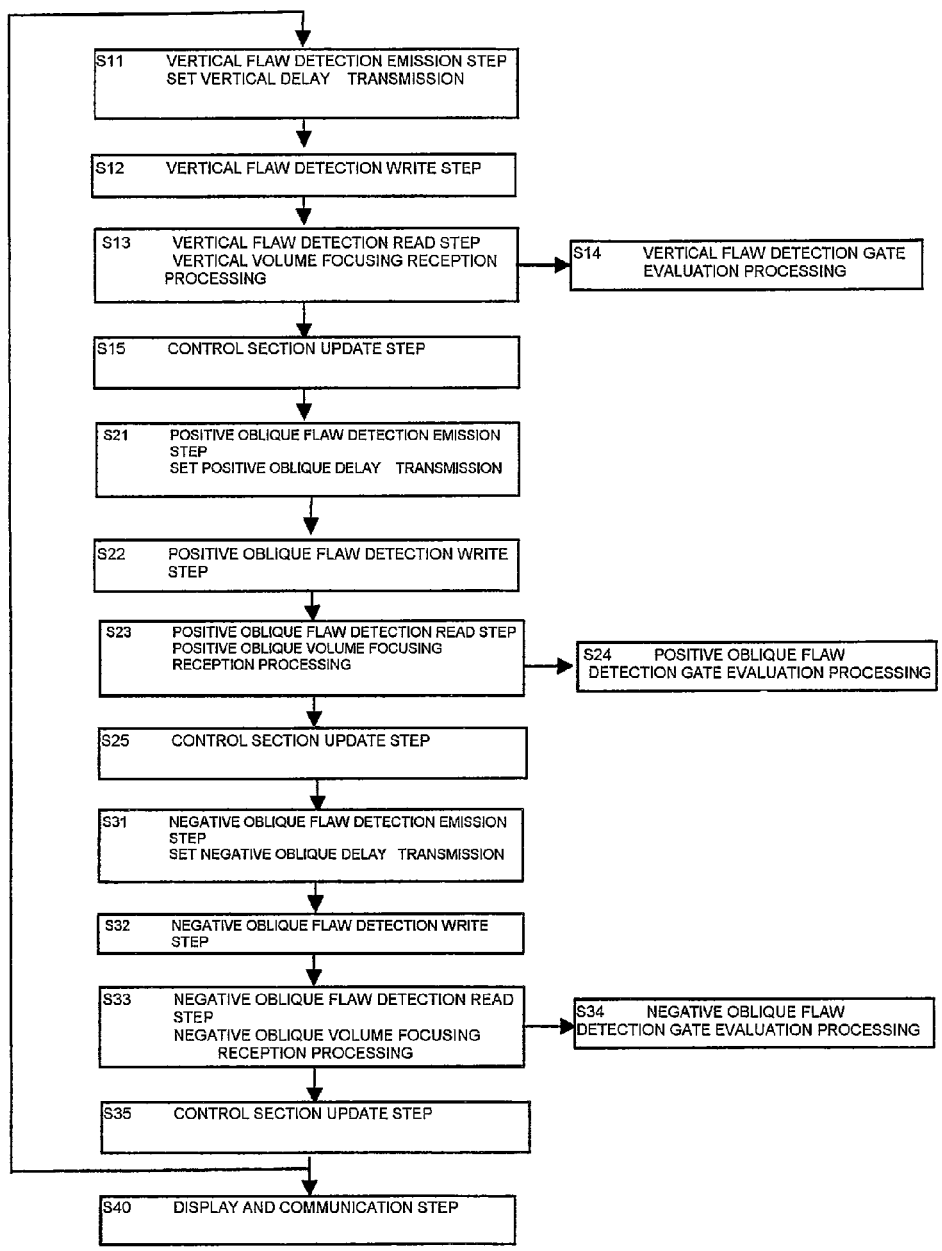
[FIG. 16] It is a flow chart showing a control procedure of the above ultrasonic flaw detection equipment.
Figure 17:
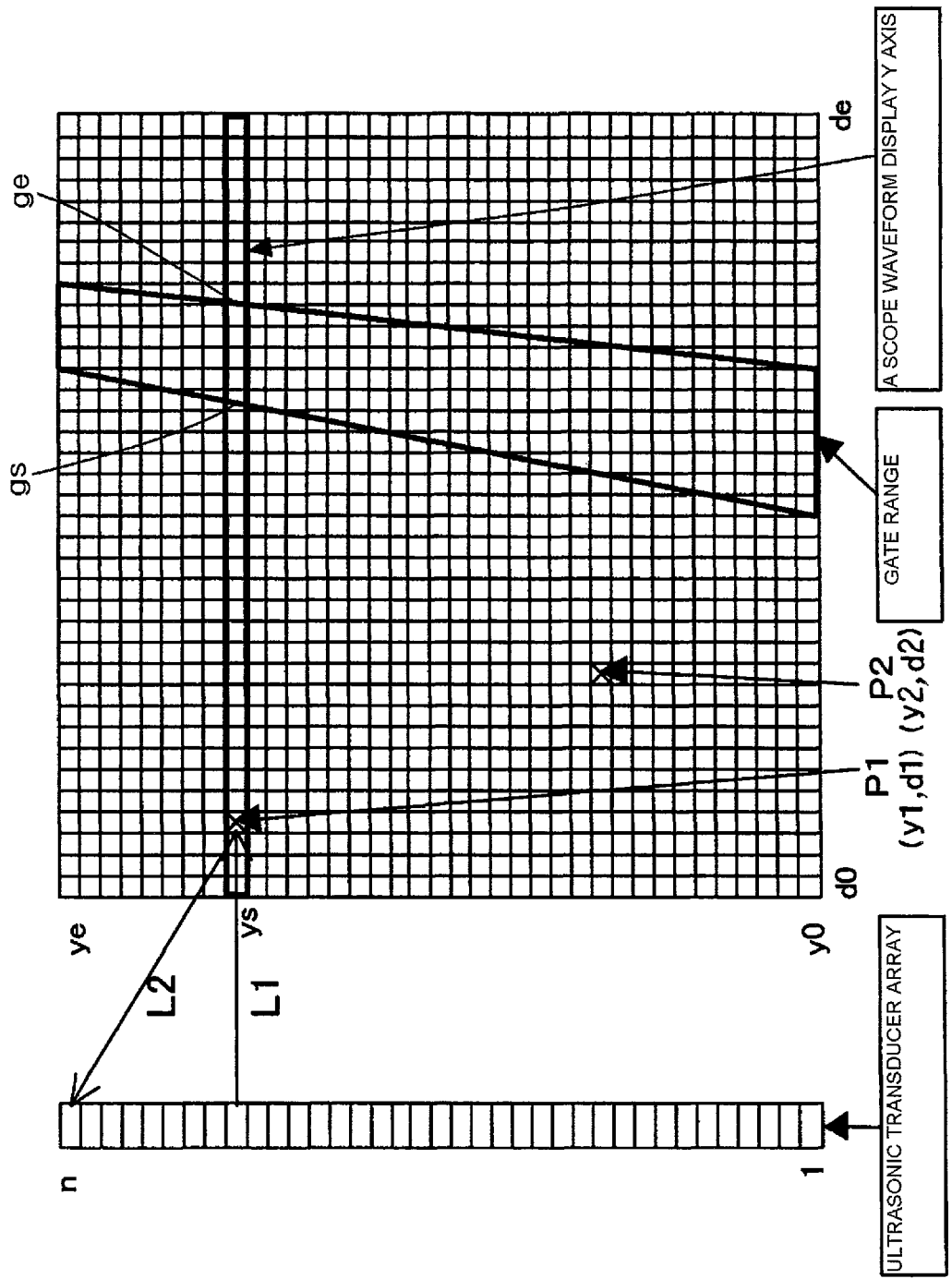
[FIG. 17] It is an explanatory diagram showing an image of electronic operation of the ultrasonic flaw detection equipment.
Figure 18:
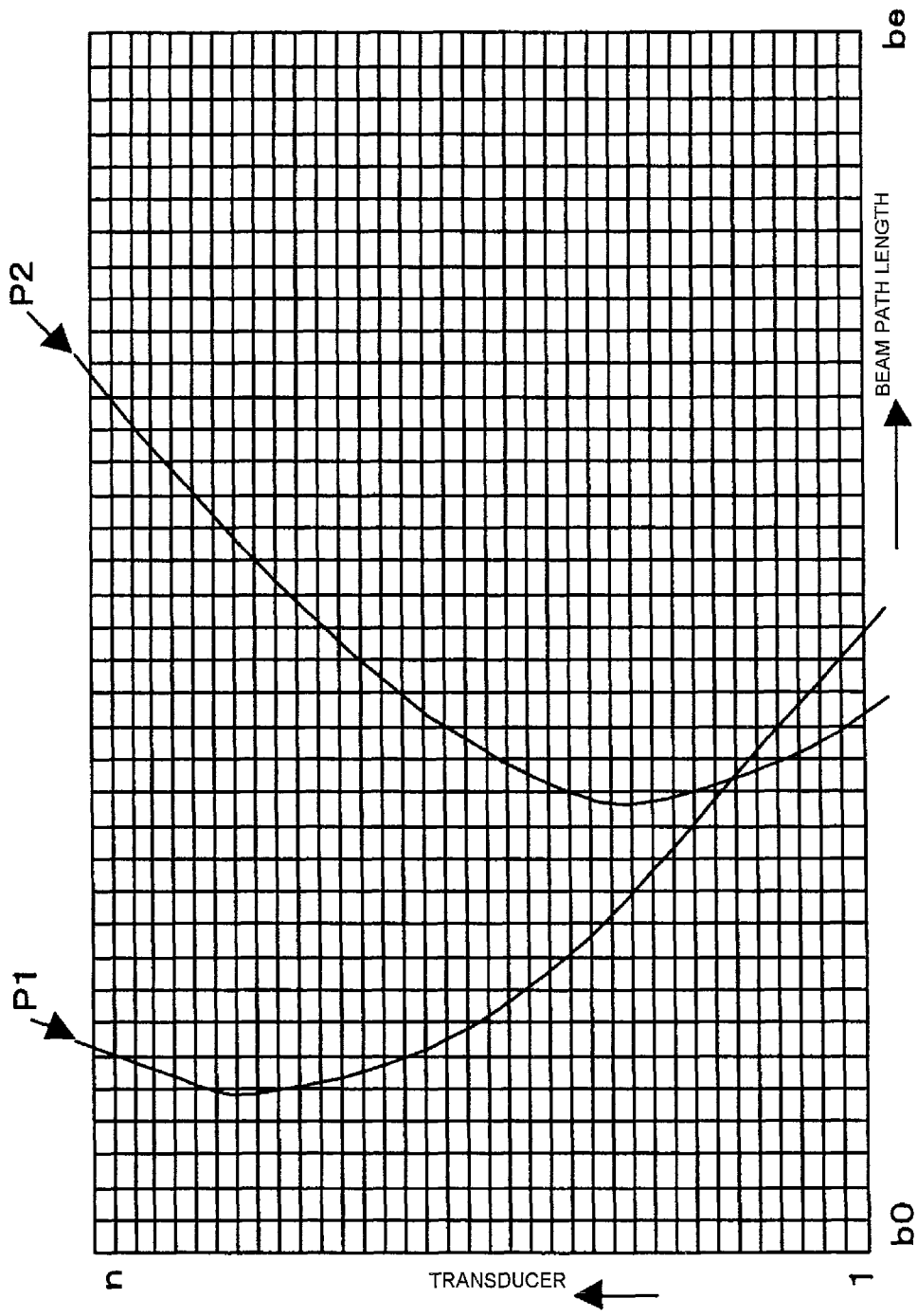
[FIG. 18] It is an explanatory diagram showing an image of a phase synthetic curve in vertical flaw detection, the phase synthetic curve on a waveform memory of the ultrasonic flaw detection equipment.
Figure 19:
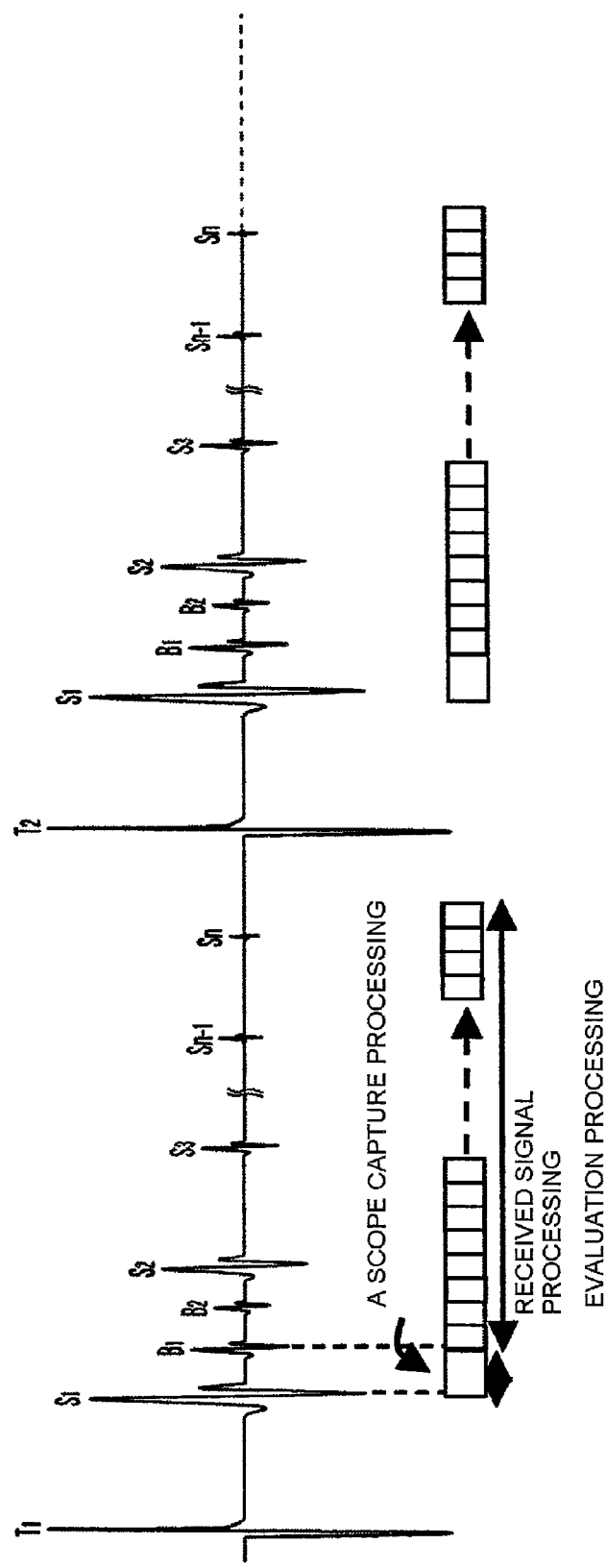
[FIG. 19] It shows a time chart of signal processing of volume focusing.

FIG. 1 is a schematic sectional view showing the placement of array probes of equipment in accordance with the embodiment of the invention. FIG. 2 is a schematic side view showing the above placement. FIG. 3 is a block diagram of the equipment. FIG. 4 is a block diagram of an enlarged principal portion of the block diagram of FIG. 3. FIG. 5 is a schematic sectional view showing a focus position of ultrasonic waves emitted from one array probe of the above equipment toward a material being tested. FIG. 6 is a schematic longitudinal sectional view explaining a plane wave in volume focusing in which a test object is a square billet. FIG. 7 is a schematic longitudinal sectional view explaining volume focusing in the invention in which a test object is a round rod (a cylindrical material). FIG. 8 is a schematic longitudinal sectional view showing how to set a correction value in vertical flaw detection of the embodiment of the invention. FIG. 9 is a schematic longitudinal sectional view showing how to set a correction value in oblique flaw detection of the embodiment of the invention. FIG. 10 is a schematic longitudinal sectional view showing the range of propagation of ultrasonic waves in vertical and oblique flaw detection of the embodiment of the invention. FIGS. 11 to 13 are schematic longitudinal sectional views showing pseudo electronic scanning in vertical flaw detection of the embodiment of the invention. FIGS. 14 and 15 are schematic longitudinal sectional views showing pseudo electronic scanning in oblique flaw detection of the embodiment of the invention. FIG. 16 is a flow chart showing a control procedure of the above ultrasonic flaw detection equipment. FIG. 17 is an explanatory diagram showing an image of pseudo electronic scanning of the ultrasonic flaw detection equipment. FIG. 18 is an explanatory diagram showing an image of a phase synthetic curve in vertical flaw detection, the phase synthetic curve on a waveform memory of the ultrasonic flaw detection equipment.

This equipment performs internal flaw detection of a cylindrical material being tested, that is, the material having a virtually circular cross-sectional shape.

As shown in FIG. 3, this equipment includes first to sixth flaw detecting units k1 to k6, an overall control section 100, and a screen display section 110.

In this embodiment, each of the flaw detecting units k1 to k6 serves as a vertical flaw detection apparatus and an oblique flaw detection apparatus.

In this embodiment, since the flaw detecting units k1 to k6 have the same configuration, they are explained collectively as a flaw detecting unit k.

The flaw detecting unit k includes an array probe 10 (hereinafter referred to as an ultrasonic transducer array 10 if necessary) having a plurality of transducers 1 . . . 1 which can be arranged along the front surface of the material being tested, an exciting unit exciting the transducers 1 . . . 1 of the array probe 10, a waveform memory, a phase combining unit, a focusing unit, an angle correcting unit, a gate processing unit, and an A scope memory unit, and can perform a volume focusing flaw detection method in which, in vertical flaw detection and oblique flaw detection, ultrasonic waves are transmitted toward the material being tested from all the transducers of the array probe at a time, the reflection echoes thereof are received by all the transducers, A scope waveforms of the elements, the A scope waveforms stored in the waveform memory, are combined by the phase combining unit, and evaluation is performed.

As shown in FIG. 1, the array probes 10 . . . 10 (10*a* . . . 10*f*) of the flaw detecting units k1 . . . k6 are disposed so as to surround a material m being tested along the circumference of the material m being tested in a cross section of the material m being tested which is a cylinder, the cross section orthogonal to the axial direction.

A group of transducers of each array probe 10, that is, a plurality of transducers 1 . . . 1 are arranged in an arc along a circle exhibited by the material m being tested in the cross section described above. In this embodiment, one array probe 10 has 128 transducers (segments). However, the number of transducers is not limited to 128; it is also possible to adopt an array probe 10 which does not have 128 transducers, for example, an array probe 10 having fewer than or more than 128 transducers.

It is preferable that the arc exhibited by the transducers 1 . . . 1 be concentric with the circle exhibited by the material being tested in the cross section described above. However, the arrangement is not limited to the arrangement described above in which the group of transducers is disposed so as to be concentric with the material being tested; the center of the group of transducers may be located in a position off the core of the material being tested. Moreover, it is preferable that the radius of the arc exhibited by the group of transducers be twice as large as the radius of the material being tested. For example, when the radius of the circle exhibited by the material being tested is 50 mm, it is preferable to set the radius of the arc exhibited by the group of transducers at 100 mm. However, such dimensional settings can also be changed.

Moreover, it is preferable that the array probes 10 . . . 10 be placed at equal intervals.

For example, in a cross section orthogonal to the axial direction of the material m being tested, as shown in FIG. 1, the array probe 10*a* of the first flaw detecting unit k1 may be placed in a 12 o'clock position of a clock, the array probe 10*b* of the second flaw detecting unit k2 may be placed in a 10 o'clock position of a clock, the array probe 10*c* of the third flaw detecting unit k3 may be placed in an 8 o'clock position of a clock, the array probe 10*d* of the fourth flaw detecting unit k4 may be placed in a 6 o'clock position of a clock, the array probe 10*e* of the fifth flaw detecting unit k5 may be placed in a 4 o'clock position of a clock, and the array probe 10*f* of the sixth flaw detecting unit k6 may be placed in a 2 o'clock position of a clock. However, the placement is not limited to the placement in which all the array probes 10 . . . 10 are placed at equal intervals as long as flaw detection can be thoroughly performed on the inside of the material being tested in the cross section described above.

It is preferable that each array probe 1 be placed in such a way that the arc exhibited by the group of transducers is concentric with the material m being tested. However, the radius of curvature of the group of transducers of the array probe and the placement of the array probes are not limited to the radius of curvature and the placement in which the arc exhibited by the group of transducers is concentric with the material m being tested. The embodiment can be implemented satisfactorily even when the arc exhibited by the group of transducers is not concentric with the material m being tested as long as, for example, the core O of the material m being tested is located on a perpendicular bisector Q2 of a line segment Q1 connecting the ends of the arc exhibited by the group of transducers, that is, the perpendicular bisector Q2 is the normal of the circle exhibited by the material m being tested, in other words, the center of the circle to which the arc exhibited by the group of vibration transducers belongs is located on the normal to the circle exhibited by the material m being tested (FIG. 5).

Since the six array probes 10*a* . . . 10*f* have the same configuration, the array probe 10*a* located in the uppermost part in FIG. 1 with respect to the material m being tested will be explained as the representative of the probes. The array probe 10*a* emits ultrasonic waves once downward by a vertical flaw detection method, and emits ultrasonic waves once rightward by an oblique flaw detection method toward the material m being tested as compared to the ultrasonic waves emitted by the vertical flaw detection method. Furthermore, the array probe 10*a* emits ultrasonic waves once leftward toward the material being tested as compared to the ultrasonic waves emitted by the vertical flaw detection method. Likewise, other probes perform one operation of vertical flaw detection and two operations of oblique flaw detection in different directions by emitting ultrasonic waves three times. The flaw detection ranges by the vertical flaw detection and the oblique flaw detection and how to set the ranges will be described later.

When the six array probes 10*a* . . . 10*f* end the above transmission of ultrasonic waves and reception processing associated therewith, the six array probes 10*a* . . . 10*f* change their positions with respect to the axial direction of the material being tested and repeat the above flaw detection. In this case, since the flaw detection is online flaw detection, scanning performed by the probe in the axial direction is realized by transporting the material being tested on a production line of the material m being tested. In other words, the invention can complete transmission and reception processing smoothly during the transportation of the material being tested on the production line by realizing the shortening of flaw detection time.

Incidentally, in the above description, all the transducers 1 . . . 1 of the array probe 10 are vibrated. When, for example, a line of transducers 1 . . . 1 has a length exceeding a range (coverage range) covered by flaw detection performed by one array probe 10, a chain of transducers 1 . . . 1, which is part of all the transducers 1 . . . 1 of one array probe 10, corresponding to the range covered by the probe 10 can be vibrated at a time as all the transducers mentioned above. A case where, for example, four transducers at each end (eight transducers in total) of 128 transducers of one array probe are simply provided and not used as a transducer and a chain of 120 transducers are used as all the transducers is not excluded.

As shown in FIG. 1, the space (gap) between the array probes 10*a* . . . 10*f* and the surface of the material m being tested is filled with flaw detection water T conveying the ultrasonic waves.

In this flaw detection equipment, well-known immersion testing or local immersion method can be adopted.

As shown in FIG. 2, the array probes 10*a* . . . 10*f* of the first to sixth flaw detecting units k1 to k6 are disposed on different cross sections of the material being tested, that is, in different positions of the cylindrical material being tested with respect to the axial direction, so as not to be affected by ultrasonic waves emitted by the array probes 10*a* . . . 10*f* or reflected waves thereof (including ghost echoes).

The material m being tested, which is a round rod, is transported on the production line described above along a longitudinal direction of the rod, that is, along an axial direction of the rod. As shown in FIG. 2, the array probes 10*a* . . . 10*f* are disposed in different positions in a transportation direction E.

Moreover, as described above, by disposing the array probes 10a . . . 10f at some midpoint of the transportation line, and disposing the lines of the transducers 1 . . . 1 of the array probes 10a . . . 10f so as to intersect with the transportation line, it is possible to make the probe perform mechanical scanning online on the production line of the cylindrical material as described earlier.

In this embodiment, on the production line (not shown) of a material being tested which is a material product such as steel, by disposing the ultrasonic transducer arrays 10 so as to intersect with the flow of the production line of the material being tested, that is, by placing the ultrasonic transducer arrays across the production line so that the transducers 1 . . . 1 are disposed over at least the entire width (the breadth) to be tested, the entire width of the material being tested across which the ultrasonic transducer arrays 10 are placed, flaw detection is sequentially performed on all areas in the material being tested, the all areas to be subjected to flaw detection, in each position in the transportation direction (the length direction) of the line for the material being tested.

However, when no online flaw detection is performed, the embodiment can be so implemented that the flaw detection equipment is provided with an additional physical scanning unit that moves a probe relative to the material being tested in the axial direction of the material being tested as described above.

As shown in FIG. 5, actual focuses at the time of transmission of ultrasonic waves in vertical and oblique flaw detection are set so as to be closer to the array probe 10 than a line Q3 which intersects a perpendicular bisector Q2 of a line segment Q1 connecting the ends of the arc exhibited by the group of transducers 1 . . . 1 of the array probe 10 at a right angle at the core O (the center of the circle exhibited by the cross section of the material m being tested) of the material m being tested.

The perpendicular bisector Q2 passes through the core O, and an actual focus in vertical flaw detection, that is, a focus F0 of ultrasonic waves at the time of transmission in vertical flaw detection is located on the perpendicular bisector Q2 and between an incident section a3-a4 on the circumference of the circle exhibited by the cross section of the material m being tested, the incident section a3-a4 which the ultrasonic waves are made to enter in the vertical flaw detection method, and the core O. When the arc exhibited by the group of transducers 1 . . . 1 is concentric with the material being tested, it is preferable that the actual focus F0 in the vertical flaw detection be set on the perpendicular bisector Q2 and at an intermediate point between the incident section a3-a4 and the core O.

As shown in FIG. 5, focuses F1 and F2 at the time of transmission in two operations of oblique flaw detection are set in positions in the material m being tested, the positions which are closer to the array probe 10 than the line Q3 which intersects the perpendicular bisector Q2 at a right angle at the core O, and, unlike the vertical flaw detection, are set in positions off the perpendicular bisector Q2 to the left or right. The above focus settings will be described in detail later.

After being set as described above, as shown in FIG. 10, the array probe 10 (the first array probe 10a) transmits ultrasonic waves once by the vertical flaw detection method and makes the ultrasonic waves reach a counter section a1-a2 facing the incident section a3-a4 on the circumference of the circle exhibited by the material being tested from the incident section a3-a4 on the circumference of the circle exhibited by the material m being tested. Moreover, the array probe 10 transmits the ultrasonic waves once by the oblique flaw detection method and makes the ultrasonic waves reach an adjacent section b1-b2 adjacent to one end of the counter section a1-a2 on the circumference of the circle exhibited by the material being tested, and transmits the ultrasonic waves once again by the oblique flaw detection method and, makes the ultrasonic waves reach an adjacent section c1-c2 adjacent to the counter section a1-a2 on the side opposite to the above adjacent section b1-b2 with the counter section a1-a2 interposed therebetween on the circumference of the circle exhibited by the material being tested. The ultrasonic waves transmitted three times by one array probe described above may be transmitted in any sequence.

The ultrasonic waves inside the material being tested in the vertical flaw detection and the oblique flaw detection diverge after converging on the focus, and spread to each region shaded in wave patterns in FIG. 10.

As is the case with the volume focusing flaw detection (FIG. 20(B)) performed on a material being tested, the material which is rectangular as seen in a sectional view, the transmitted waves of the ultrasonic waves shown in FIG. 10 are plane waves or pseudo plane waves. However, the pseudo plane waves for a material being tested, the material, which is circular, as seen in a sectional view, differs from those for the material, which is rectangular as seen in a sectional view in that they are apparently arc-shaped, not linear. A description will be given on this point.

The conventional volume focusing method is performed on an object having a linear surface as seen in a sectional view, and, as shown in FIG. 6, concurrently excites all the transducers 1 . . . 1 arranged linearly along the surface of the material m being tested toward positions on the surface of the material m being tested at the time of transmission of ultrasonic waves, and thereby propagates the ultrasonic waves required for reception processing through almost the entire region inside the material being tested as seen in a sectional view by emitting the ultrasonic waves once by exciting all the transducers of the array probe at a time in actuality by plane waves in which beams travel nearly parallel to each other or pseudo plane waves whose focus is set in the distance by setting timing of excitation of the transducers or pseudo plane waves having no focus as a result of the ultrasonic waves being diverged. In addition to that, the method performs pseudo electronic scanning corresponding to electronic scanning in reception processing, thereby realizing the shortening of flaw detection time.

In the equipment of the invention which tests a cylindrical member, the above arc-shaped waves (hereinafter referred to as cylindrical waves) generated by vibrating all the transducers at a time, the transducers arranged in an arc along the circle exhibited by the cross section of the cylindrical material, correspond to the plane waves or pseudo plane waves (hereinafter, including the plane waves, referred to as pseudo plane waves) in the existing volume focusing flaw detection method performed on a member which is rectangular as seen in a sectional view, that is, a member having a linear surface as seen in a sectional view. The equipment according to the invention appears to be different in that the focus is located inside the material m being tested. However, when the plane waves described above are regarded as waves which make the beams enter the surface of the material being tested at the same angle, for example, make the beams enter the surface of the material being tested almost perpendicularly as far as vertical flaw detection goes (make each beam correspond to the normal at an incident point), the cylindrical waves here are the same as the plane waves in that the cylindrical waves also make the beams enter the surface of the material being tested perpendicularly (make the beams correspond to the normal), the material which is circular as seen in a sectional view, as shown in FIG. 7. However, prior to divergence, the cylindrical waves converge on the core O of the material m being tested, that is, are focused on the core O of the material m being tested as described above. The invention does not exclude a case where the focus is set on the core O of the material m being tested as described above; however, from the viewpoint of securing a wide flaw detection range, setting the focus on this side of the core O, that is, in a position closer to the probe than the core O and thereby propagating the cylindrical waves more widely is regarded as a preferred embodiment.

Therefore, here, the volume focusing method makes the ultrasonic waves reach a region to be subjected to flaw detection widely at the time of transmission thereof, irrespective of the shape of a material being tested and irrespective of whether a focus position is inside or outside of a material being tested, by taking advantage of the arrangement width of the transducers of an array probe without allowing the ultrasonic waves to be focused inside the region to be subjected to flaw detection. In particular, the above cylindrical waves are generated in the invention in which a member, which is circular as seen in a sectional view, is used as a material being tested.

As described above, when the focus is placed on the core O, if the arc exhibited by the group of transducers of the probe is concentric with the material m being tested as shown in FIG. 7, all the beams emitted from the transducers and entering the material being tested are the normal to the circle exhibited by the cross section of the material being tested, the angles of incidence of the ultrasonic beams of all the transducers $1 \ldots 1$ are 0 degree, and the angles of refraction after entering the material being tested are also 0 degree. Therefore, the ultrasonic waves may be emitted from all the transducers $1 \ldots 1$ concurrently without introducing delay at the time of excitation of the transducers $1 \ldots 1$.

On the other hand, in order to make the cylindrical waves described above converge on the focus F0 located closer to the probe than the core O of the above-described material m being tested and diverge after passing through the focus F0 in the vertical flaw detection described above as shown in FIG. 8, it is necessary to change the angle of incidence for each of the transducers $1 \ldots 1$.

Moreover, the angles of refraction of the beams after entering the material being tested at their respective incident positions differ from angle of incidence to angle of incidence by Snell's law due to a difference between the velocity of sound propagating through the detection water T and the velocity of sound propagating through the material being tested.

As for Snell's law described above, let the angle of incidence be $\theta$, the angle of refraction be $\phi$, the velocity of sound in the detection water T be vi, and the velocity of sound (of the longitudinal waves) in the material m being tested be vj, then $(\sin \theta/vi)=(\sin \phi/vj)$ holds.

Both the angle of incidence $\theta$ and the angle of refraction $\phi$ are the angles, which the beam before refraction and after refraction forms with the normal at an incident point. The material through which sound propagates and the temperature determines the above velocity of sound.

This equipment utilizes the longitudinal waves generated in the material being tested at the time of transmission, and the above-described angle of refraction is the angle of refraction of the longitudinal wave.

Therefore, as shown in FIG. 8, in one array probe 10, as for the ultrasonic beams of transducers 1s and 1t, the angles of incidence $\theta$s and $\theta$t at different incident points 1m and 1n have to be set at angles with consideration given to the angles of refraction $\phi$s and $\phi$t by Snell's law to obtain the focus F0. It goes without saying that the ultrasonic beams of the transducers 1s and 1t, which are not symmetrical with respect to the perpendicular bisector Q2 mentioned earlier, have different angles of incidence. In addition to that, the transducers located so as to be symmetrical with respect to the perpendicular bisector Q2 also have different angles of incidence because the positive and negative of the angle of incidence of one transducer are opposite to those of the other.

As described above, the transducers are excited by shifting timing by Snell's law so as to obtain the focus F0 at the above-described position, which is different from the core O. In other words, the transducers $1 \ldots 1$ are vibrated by such a delay pattern. For example, the beams which have been emitted from the transducer 1s and the transducer 1t which is different from the transducer 1s and passed through the focus F0 reach positions as and at on the above-described counter section a1-a2.

In the above description, both the angle of incidence and the angle of refraction of only the beam corresponding to the perpendicular bisector Q2, that is, only the ultrasonic beam emitted from a transducer x1 positioned in the middle of the arrangement of the transducers become 0 because this beam perpendicularly enters the material being tested, and there is no need to delay this beam. A position a0, which the above beam reaches, is a bisection point of the counter section a1-a2.

As shown in FIG. 9, also in the transmission of the ultrasonic waves in oblique flaw detection, the ultrasonic waves are made to reach positions on the adjacent section b1-b2 by providing timing of excitation with consideration given to the positions of the above-described focuses F1 and F2, that is, a delay pattern to the transducers $1 \ldots 1$.

Specifically, delay is introduced into timing of excitation so that the beams of the two different transducers 1s and 1t described above obtain angles of incidence $\theta$s' and $\theta$t' with consideration given to angles of refraction $\phi$s' and $\phi$t' by Snell's law in order to obtain the focus F1 at the above-mentioned position which is different from the core O. As a result, the beams which have been emitted from the transducers 1s and 1t, entered the material being tested at different incident points 1m' and 1n', and passed through the focus F1 reach positions bs and bt on the adjacent section b1-b2.

In oblique flaw detection, there is no beam, which perpendicularly enters the material being tested. Thus, for example, the transducer 1x in the middle of the arrangement also has to be excited by introducing delay by Snell's law so as to have an angle of incidence $\theta$x with consideration given to an angle of refraction $\phi$x. In FIG. 9, b0 represents a position on the adjacent section b1-b2, the position which the beam of the transducer x1 reaches.

In FIG. 9, oblique flaw detection in which the ultrasonic waves are made to reach the adjacent section b1-b2 has been explained as an example. However, another oblique flaw detection in which the ultrasonic waves are made to reach the adjacent section c1-c2 is the same as that described above, and therefore explanations will be omitted.

From the viewpoint of detecting a defective echo near the adjacent section, unlike vertical flaw detection, it is appropriate to set the angle of refraction of the beam of each transducer at an angle greater than 20 degrees (absolute value) at the time of transmission in oblique flaw detection in order to detect a defective echo reliably in a dead band, which will be described next. The positive and negative of the angle of refraction in the adjacent section b1-b2 are opposite to those of the adjacent section c1-c2. Moreover, an upper limit is set in a range that allows the beam to enter the material being tested by Snell's law. Here, the absolute values of both the angle of refraction and the angle of incidence are set in the range of 0 to 90 degrees.

Here, the dead band will be explained by using FIG. 5.

As shown in FIG. 5 with oblique lines, in vertical flaw detection, a dead band produced by reflection which occurs at the surface of the material being tested when the ultrasonic waves enter the material being tested is present near the incident section a3-a4, and a dead band produced by reflection which occurs at the counter section a1-a2 is also present near the counter section a1-a2 facing the incident section a3-a4. The dead band near the counter section a1-a2 is a region having a depth of about 3 mm from the counter section a1-a2 side toward the inside of the material m being tested, and is thin and shallow compared to the above dead band produced by reflection which occurs when the ultrasonic waves enter the material being tested.

In vertical flaw detection, flaw detection of the inside of a region surrounded by F0-a1-a2 of FIG. 10 is mainly performed, and, by operations of oblique flaw detection, flaw detection of the adjacent sections b1-b2 and c1-c2 on the circumferential surface of the material being tested is performed. In the invention, the dead band produced by reflection which occurs at the incident section a3-a4 when the ultrasonic waves enter the material being tested is subjected to flaw detection by vertical flaw detection and oblique flaw detection performed by other probes (the probes other than the first array probe 10a in the above description), and the dead band near the counter section a1-a2 is subjected to flaw detection by oblique flaw detection performed by other probes.

As a result, in vertical flaw detection, DDF (dynamic depth focusing) is performed in volume focusing flaw detection of the above region F0-a1-a2 shown in FIG. 10 as processing on the ultrasonic waves receiving side. On the other hand, there is no need to perform DDF in oblique flaw detection, and the focus is set only near the adjacent sections b1-b2 and c1-c2 (almost on the circumference) in pseudo electronic scanning.

That is, in vertical flaw detection, flaw detection of a central part (near the core) inside the material being tested is primarily performed, and, in oblique flaw detection, flaw detection is performed mainly on a thin area near the adjacent section on the surface of the material being tested. In other words, in flaw detection by vertical flaw detection, the focus is obtained for each individual focal row in a plurality of positions in the depth direction by DDF in processing on the receiving side; in flaw detection by oblique flaw detection, the focus is obtained, without performing DDF, for each individual focal row in the deepest part (with respect to the incident position) in the depth direction, that is, only on the adjacent section. This is because a main object is to perform flaw detection on a shallow part inside the material m being tested, the shallow part along the adjacent section b1-b2 shown in FIG. 10, by one operation of oblique flaw detection, and perform flaw detection on a shallow part inside the material m being tested, the shallow part along the adjacent section c1-c2 shown in FIG. 10, by the other operation of oblique flaw detection.

However, the embodiment can also be so implemented that, also in oblique flaw detection, flaw detection is performed on the inside of a region surrounded by F1-b1-b2, the region inside the material m being tested, or the inside of a region surrounded by F2-c1-c2 by using the dynamic focusing method.

Incidentally, the above focal row is a group of beams, which is a unit of scanning in pseudo electronic scanning in processing on the receiving side. That is, the focal row is generated at every shift of the memory corresponding to the transducer in pseudo electronic scanning.

As for processing on the receiving side in vertical flaw detection, the same pseudo electronic scanning as that shown in FIG. 20(B) described earlier is performed.

Specifically, as shown in FIG. 11, indicator points f1 to f7 corresponding to the focal rows are set on the above-described counter section a1-a2 on the circumference of the circle exhibited by the material m being tested as seen in a sectional view. Incidentally, for convenience of explanation, the seven indicator points are set; however, in reality, more indicator points are usually set because it is necessary to set a pitch (a spacing between the indicator points) with which flaw detection is thoroughly performed in a flaw detection range.

The indicator points f2 to f6 are points, which equally divide the space between the points f1 and f7 located at the extremities. Central beams f10, f20, f30, f40, f50, f60, and f70 of groups of memories corresponding to the transducers to be shifted, that is, the focal rows, are set in such a way that the central beams pass through each of the points f1, f2, f3, f4, f5, f6, and f7 from f1, which is one of the indicator points fl and f7 located at the extremities, toward the other indicator point f7 (f50 and f70 are shown in FIGS. 12 and 13, respectively; other central beams are not shown in the drawings). Then, each focus of DDF is set on each central beam. In FIG. 11, f11 to f17 represent the focuses of DDF on the central beam f10 of the focal row corresponding to the indicator point f1. The focus points f11 to f17 correspond to the points indicated by black circles of FIG. 20(B). To prevent the drawing from becoming complicated, a state of convergence of the beams forming DDF, the state shown by dashed lines in FIG. 20(B), is not shown in FIG. 11 and FIGS. 12 and 13, which will be explained next.

As shown in FIG. 11, pseudo electronic scanning is performed in the y direction, and the beams forming the focal row are shifted in the order of the indicator points f1, f2, f3 . . . f7, whereby the focal rows passing through the indicator points are sequentially formed.

FIG. 12 shows a focal row corresponding to the indicator point f5 in the middle of the pseudo electronic scanning described above. In FIGS. 12, f51 to f57 represent the focuses of DDF of the focal row corresponding to the indicator point f5. As described above, pseudo electronic scanning started from the indicator point f1 serving as a starting point eventually ends at the indicator point f7 serving as an end point as shown in FIG. 13. In FIG. 13, f71 to f77 represent the focuses of DDF of the focal row corresponding to the indicator point f7.

In the vertical flaw detection, the positions of the indicator points f1 to f7 are in the dead zone, that is, the dead band described above, and do not become points (flaw detection points) at which flaw detection is performed.

Also in the processing on the receiving side, as shown in FIGS. 11 to 13, the angles of incidence of the central beams f10 to f70 entering the material being tested at incident points h1 to h7 (only h1, h5, and h7 are shown in the drawing) have to be set with consideration given to the angle of refraction by Snell's law described earlier.

That is, at the incident points h1 to h7 with different angles of incidence, the angles of refraction are also different.

Moreover, the beam path lengths of the central beams vary from focal row to focal row (in the flaw detection water T, in the material being tested, the beam path lengths vary).

For each central beam of such a focal row, the angle of incidence of each central beam at each incident point is determined with consideration given to the different angles of refraction and beam path lengths so that the central beam passes through each indicator point.

One focal row is formed of a plurality of beams corresponding to the transducers of a plurality of groups of transducers, and even other beams (beams other than the center) belonging to the same focal row as the central beam have different angles of refraction and different angles of incidence because the incident points of the beams are different from each other. However, the beams belonging to the same focal row, the beams including the central beam, have the same beam path length because they pass through the same indicator point concurrently. For example, in FIG. 11, the beams of the focal row whose indicator point is f1 (in FIG. 11, to prevent the drawing from becoming complicated, only three beams, the central beam and the right and left beams, are shown, and other beams are omitted) pass through the indicator point concurrently.

Different focal rows have different beam path lengths as described above.

Moreover, even when the beams belong to the same focal row, the angle of incidence has to be set for the beams other than the central beam in order to obtain DDF. Also in this case, consideration has to be given to a difference in angle of refraction by Snell's law depending on the incident point. For example, for each of the DDF focuses of f1 to f7 in FIG. 11, the angles of incidence of the beams other than the central beam have to be set with consideration given to the angle of refraction.

Each focal row gradually changes the angle of incidence according to the angle of refraction of each of the beams forming the focal row.

Therefore, in the processing on the receiving side in the vertical flaw detection, a correction is made to the angle of incidence for forming the focal row passing through each indicator point, and a correction to introduce delay is made so as to obtain the angle of incidence for forming DDF in each individual focal row.

For example, in pseudo electronic scanning, with respect to the normal (both the angle of incidence and the angle of refraction are 0 degree) to a material being tested, the material which is circular as seen in a sectional view, the direction is changed so that the focal row passes through each indicator point as follows: the angle of incidence of (the central beam of) the first focal row of scanning is +10 degrees, the angle of incidence of (the central beam of) the second focal row is +9 degrees, the angle of incidence of (the central beam of) the third focal row is +8 degrees . . . , the angle of incidence of (the central beam of) the focal row in the center of the arc, the focal row located equidistant from the ends of the arc exhibited by the array, is ±0 degree, and the angle of incidence of (the central beam of) the focal row next to the central focal row is −1 degree. Then, in addition to the above correction, a correction to obtain DDF is made to the beams belonging to one focal row, the beams other than the central beam.

Incidentally, as a result, in such pseudo electronic scanning, though not apparent from the drawings, each focal row gradually changes the angle of incidence according to the angle of refraction in the manner as described above independently of the position of the actual focus, that is, the focus F0 of the ultrasonic waves at the time of transmission.

Also in the oblique flaw detection, a plurality of indicator points are set on the adjacent section, and focal rows passing through the indicator points are sequentially formed. Here, processing of the array probe 10a on the receiving side performed on the adjacent section b1-b2 located on the right side of the counter section a1-a2 will be explained. However, processing on the receiving side performed on the adjacent section c1-c2 located on the left side of the counter section a1-a2 is the same as the processing performed on the adjacent section b1-b2 located on the right side of the counter section a1-a2, and explanations thereof are omitted.

Indicator points g2 to g6 are points, which equally divide the space between points g1 and g7 located at the extremities (FIG. 14). Central beams g10, g20, g30, g40, g50, g60, and g70 of a group of memories corresponding to the transducers to be shifted, that is, the focal rows, are set in such a way that the central beams pass through each of the points g1, g2, g3, g4, g5, g6, and g7 from g1, which is one of the indicator points g1 and g7 located at the extremities, toward the other indicator point g7 (the central beams other than g10 and g70 are not shown in the drawings).

As shown in FIG. 14, pseudo electronic scanning is performed in the y direction, and shifting is performed in the order of the indicator points g1, g2, g3 . . . g7, whereby the focal rows passing through the indicator points are sequentially formed. FIG. 14 shows a focal row corresponding to the indicator point g1 serving as a starting point in pseudo electronic scanning. Eventually, the indicator point g7 shown in FIG. 15 becomes an end point of the pseudo electronic scanning.

In this embodiment, although DDF is not performed in oblique flaw detection, as for pseudo electronic scanning, by setting the indicator points g1, g2, g3 . . . g7 as described above, pseudo electronic scanning is sequentially performed on each indicator point as in the vertical flaw detection. As described earlier, in the oblique flaw detection, the indicator point is a flaw detection point (to be precise, rather than the indicator point, a position near the indicator point in a region of the dead band inside the material being tested is a flaw detection point).

The angle of incidence of the central beam of each focal row in the oblique flaw detection is also set by Snell's law in such a way that the central beam passes through each indicator point with consideration given to the angle of refraction. In addition, the processing is the same as the processing on the receiving side in the vertical flaw detection in that the angle of incidence is set with consideration given to the angle of refraction so that the beams forming one focal row pass through the same indicator point, that is, have the same beam path length. However, in this embodiment in which DDF is not performed, it is not necessary to make a correction to DDF.

As described above, the counter section a1-a2 is a section which the transmitted waves reach in vertical flaw detection, the adjacent section b1-b2 and the adjacent section c1-c2 described above are sections which the transmitted waves reach in the operations of oblique flaw detection, and the above-described indicator point set section f1 -f7 in vertical flaw detection and the above-described indicator point set section g1-g7 in oblique flaw detection are sections in which pseudo electronic scanning on the receiving side is performed.

Here, a method for actually setting the above-mentioned focus positions at the time of transmission of ultrasonic waves will be described.

First, prior to the setting of the focuses F0, F1, and F2 (FIGS. 5 and 10) at the time of transmission, a range in which the above-described indicator points are set is set on the circumference of the material being tested. Then, the counter section a1-a2 and the adjacent sections b1-b2 and c1-c2 are set on the circumference of the material being tested in such a way as to include the range in which the indicator points have been set. The positions of the focus positions F0, F1, and F2 may be selected so that such a counter section and adjacent sections are obtained.

The setting of the indicator points will be specifically described.

It is necessary to determine the indicator point set range, that is, the positions of the indicator points f1 and f7 located at the extremities, on the circumference of the material being tested (FIGS. 11 to 13) in vertical flaw detection and determine the indicator point set range, that is, in the above example, the indicator points g1 and g7, (FIGS. 14 and 15) in oblique flaw detection.

In determining the indicator point set range, the range is determined by determining a range of the material being tested, the range covered by one probe (a probe 1 Oa). The number of probes provided in the equipment may determine the range covered by each probe.

In this embodiment, since six probes 10a to 10f are used, the whole circumference (360 degrees) of the material being tested is divided by the number of array probes. As a result, the range covered by one probe is a range of the material being tested with a central angle of 60 degrees for each of vertical/oblique flaw detection. However, it is preferable that the above-described covered ranges partially overlap between the array probes 10...10. That is, a range to be subjected to flaw detection by each individual array probe is set to be wider than the angle obtained by dividing the whole circumference of the material being tested by the number of array probes. As for overlapping, when the indicator point set range f1-f7 of vertical flaw detection performed by the array probe 10a shown in FIG. 5 is taken up as an example, it is preferable that, by regarding 60 degrees described above as being made up of right-hand 30 degrees and left-hand 30 degrees with the perpendicular bisector Q2 placed therebetween, the ranges overlap in the range of 5 to 15 degrees in both right and left parts. In particular, it is preferable that the covered range be set at 80 degrees (right-hand 40 ; degrees and left-hand 40 degrees) by making the ranges overlap by 10 degrees in both right and left parts.

Moreover, also in oblique flaw detection, the indicator point set range may be set in the same manner as in the vertical flaw detection described above.

After the indicator point set range is set, a pitch between the indicator points which divide the range into equal parts on the circumference of the circle is set. As described earlier, since the focus set on the circumference in the processing on the receiving side has, in actuality, a beam width, flaw detection is not thoroughly performed if the pitch (the spacing between the indicator points) is greater than the beam width. Therefore, the pitch is set so that flaw detection is performed thoroughly.

When the pitch is set, the number of indicator points is set, making it possible to set focal rows to be formed, as for the central beam of each individual focal row and the beams thereof other than the central beam, the angle of incidence and the transducer are calculated by calculating backwards from each indicator point. By setting the angle of refraction in calculating backwards, the angle of incidence is determined by Snell's law, and the beam path length, that is, the sum total (the round-trip time) of the time the beam takes to reach the indicator point from the transducer and the time the beam takes to return from the indicator point is determined (all the beams passing through one indicator point have the same beam path length).

Based on the focal rows determined as described above and by determining the angle of incidence of each of the beams forming the focal row prior to flaw detection, it is possible to determine a delay pattern used for processing on the receiving side in volume focusing.

When flaw detection is performed, by performing memory read processing in accordance with a delay pattern determined in the manner as described above by taking into account the angle of incidence according to the angle of refraction of each of the beams forming the focal row, the focus position of DDF, the fact that the beams forming the same focal row have the same beam path length, and the fact that the central beams of the focal rows have different beam path lengths, a focal row corresponding to each indicator point can obtain the same effects in processing on the receiving side as in the case where the transducers are excited by such a delay pattern.

As described above, the equipment according to the invention produces delay corresponding to excitation timing which is provided to the actual transducers by using, as the reference, a beam whose angle of refraction is 0 degree (angle of incidence is 0 degree), that is, a beam corresponding to the normal with respect to a circle exhibited by a material being tested as seen in a sectional view, and, as for other beams, providing a correction value with respect to the above reference, the correction value calculated in advance in accordance with the above description, to the address in reading from the memory, and obtains the angle of incidence of each beam.

The above-described flaw detecting units k1 to k6 shown in FIG. 3 each have a configuration shown in FIG. 4.

Hereinafter, the configuration of the flaw detecting unit k will be described specifically by using FIG. 4.

As shown in FIG. 4, one flaw detecting unit k has an ultrasonic transducer array 10 including a plurality of transducers 1 . . . 1, a pulser section 20, a receiver section 30, a plurality of signal processing sections 40 . . . 40 corresponding to the plurality of transducers 1 . . . 1 of the ultrasonic transducer array 10, a path length counter 50, a Y direction counter 51, a D depth direction counter 52, an adder 53, a detector circuit 54, a gate circuit 60, a waveform peak storage circuit 70, and a control section 90.

As shown in FIG. 4, the equipment includes the beam path length counter 50, the Y direction counter 51, the D depth direction counter 52, and the control section 90. Each counter can be cleared or incremented by a signal from the control section 90.

The control section 90 is a device which is made up of at least a CPU, a memory, a program ROM, a screen display section, and a communication section, and can create various kinds of timing and send the timing to different sections and circuits, provide different sections with data, and read data from different sections, display the result thereof, and transmits it to other devices. As the control section 90, a commercially available computer can be used.

In FIG. 4, the ultrasonic transducer array 10 is made up of n ultrasonic transducers 1, is connected to the pulser section 20 and the receiver section 30, and emits ultrasonic waves into testing space and receives reflected ultrasonic wave echoes from the testing space.

The pulser section 20 is made up of as many spike pulser circuits as n elements of the ultrasonic transducer array 10, and the spike pulser circuits operate simultaneously by a pulse emission timing signal from the control section 90, whereby the ultrasonic transducer array 10 is excited.

The control section 90 includes a transmission processing setting section 91, a reception processing setting section 92, a focus setting section (not shown), and a gate position storing section (not shown).

In this embodiment, as described earlier, the number n of elements (the number of segments) is 128.

The transmission processing setting section 91 includes a transmission delay pattern holding section (not shown) holding a pattern of the amount of delay (delay amount) of timing of an excitation signal to be provided to each transducer, in accordance with the angle θ (FIG. 8) with respect to the normal, and a selection holding section (not shown). By inputting the diameter of a material being tested, the velocity of sound, and the angle of refraction φ before flaw detection, an operator can select a pattern of the amount of delay as a correction value according to that angle from the transmission delay pattern holding section in the transmission processing setting section 91, and can make the selection holding section hold the selection result.

As for the pattern of the correction value before flaw detection, the velocity of sound in the detection water and the velocity of sound in the material being tested are determined by the temperature and the material thereof. Therefore, it is also possible to allow the velocity of sound to be calculated or selected by inputting the material and the temperature instead of directly inputting the velocity of sound. When the diameter, the velocity of sound, and the angle of refraction are determined, the angle of incidence is determined.

Moreover, the embodiment can also be so implemented that the operator calculates the amount of correction and inputs the delay pattern directly. However, when materials having various diameters and made of various materials are tested as the material being tested, selecting patterns, various delay patterns corresponding to the materials (velocities of sound) or diameters, from the transmission delay pattern holding section as in the embodiment described above is convenient.

With reference to a case where a normal beam corresponding to the normal, that is, a beam whose angle of incidence θ is 0 degree is emitted, by shifting timing with which the transducers are excited by the exciting unit as delay (delay time) for timing with which the normal beam is emitted, the angle of incidence of other beams set in advance as described above can be realized.

As described above, when input of the angle of refraction φ (FIG. 8) described earlier along with the diameter of the material being tested and the velocities of sound in the flaw detection water and the material being tested is received as a result of the operator operating the overall control section 100, in the control section 90, the transmission processing setting section 91 determines, based on the angle of refraction φ, a corresponding angle of incidence θ, and selects a corresponding transmission delay pattern.

The setting of the covered range on the circumference of the material being tested at the time of transmission of one array probe 10 is performed in the setting described above. The angle of refraction φ described above has to be set for each individual transducer. However, the transmission processing setting section 91 automatically calculates the angle of incidence of each of the beams of the arranged transducers other than that positioned in the middle of the arrangement of the group of transducers only by making the operator set the angle of refraction of the beam of the transducer positioned in the middle of the arrangement of the group of transducers and the covered range at the time of transmission, that is, the actual focus position at the time of transmission. It is preferable that a calculating unit be provided, because this makes it easy to change the settings.

However, when vertical flaw detection is performed, since the beam of the transducer positioned in the middle of the arrangement corresponds to the perpendicular bisector Q2, setting the velocity of sound and the covered range (counter section) or the focus position is all that is needed, and there is no need to input the angle of refraction of the transducer positioned in the middle of the arrangement.

The setting of oblique flaw detection, for example, transmission of ultrasonic waves to the above-described adjacent section b1-b2 requires selection of the angle of refraction of the beam of the transducer positioned in the middle of the arrangement.

The setting of the oblique flaw detection in the adjacent section c1-c2 located on the left side of the counter section a1-a2 with the perpendicular bisector Q2 placed therebetween with respect to the adjacent section b1-b2 located on the right side of the counter section a1-a2 with the perpendicular bisector Q2 placed therebetween differs from that described above only in that the sections have a symmetric relation (the positive and negative of each individual angle of incidence θ are opposite to those of the other), and is made in the same manner as the adjacent section b1-b2 located on the right side.

At the time of transmission of the ultrasonic waves, the control section 90 provides the spike pulser circuit with a timing signal according to the delay pattern by referring to the selected delay pattern from the transmission delay pattern holding section and the selection holding section of the transmission processing setting section 91.

To make the probe emit the cylindrical waves and obtain the focuses F0, F1, and F2 in the positions shown in FIGS. 5 and 10, the delay pattern of the transmission processing setting section 91 excites the adjacent transducers with different time lags from one end of a group of arranged transducers to the other end of the group so that the transducers emit the ultrasonic waves at the different angles of incidence θ set as described above for the material m being tested.

Moreover, it is preferable that the setting of a delay pattern on the receiving side of the reception processing setting section 92, which will be described later, be performed at the same time as a result of the input by the operator.

The overall control section 100 can collectively perform selection of a delay pattern of transmission and reception in the control sections 90 of the flaw detecting units k1 to k6 as a result of the overall control section 100 being operated by the operator. Moreover, the operator can make settings of the flaw detection of a corner portion in reception processing by operating the overall control section 100.

The reception processing setting section 92 of the control section 90 forms the above-described reception angle correcting unit.

The reception processing setting section 92 includes a reception delay pattern holding section holding a pattern of the amount of correction of oblique flaw detection on the receiving side and a selection holding section.

The above-described operation of the overall control section 100 performed in advance by the operator makes it possible, in the reception processing setting section 92, to select a delay pattern on the receiving side according to the angle of incidence θ from the reception delay pattern holding section and hold the selection result in the selection holding section.

In the reception processing setting section 92, by selecting (the set range and pitch of) the indicator point and the angle of refraction, the angle of incidence and the path length of the central beam of each focal row are uniquely determined. By determining the number of transducers forming a focal row in advance, since the beam path length is the same as that of the central beam, the angle of incidence is also uniquely determined for each of the beams forming the same focal row when the angle of refraction is set, and the transducers which should belong to the same focal row are determined.

The reception processing setting section 92 is made to hold a delay pattern of correction to which the incidence angle correction value thus obtained and the correction value for obtaining the focus of DDF are added. The configuration of the reception processing setting section 92 will be described later.

The receiver section 30 is made up of as many receiver circuits as n elements of the ultrasonic transducer array 10, and, in this section, an ultrasonic wave received echo is subjected to signal amplification and is sent to the signal processing section 40.

The signal processing section 40 is made up of as many signal processing circuits 41-1 to 41-$n$ as n elements of the ultrasonic transducer array 10. Each signal processing circuit 41 is made up of an A/D converter 411, an ultrasonic waveform memory 412, a switch 413, and a dynamic focusing phase correction memory 414.

The A/D converter 411 performs analog-to-digital conversion on the ultrasonic wave signal sent from the receiver section 30, and the signal subjected to analog-to-digital conversion is written into the ultrasonic waveform memory 412. The sampling frequency of the analog-to-digital conversion is 8 or more times as high as a nominal frequency of an ultrasonic transducer. This sampling signal is supplied from the control section 90 via a first signal line (not shown). In this embodiment, the above-mentioned exciting unit of the ultrasonic flaw detection equipment is made up mainly of the pulser section 20. The above-mentioned waveform memory is made up of the receiver section 30, the A/D converter 411, and the ultrasonic waveform memory 412. Moreover, the above-mentioned phase combining unit is made up of the adder 53. In addition, the above-mentioned focusing unit is made up of the above-described Y direction counter 51, the above-described D depth direction counter 52, and each dynamic focusing phase correction memory 414.

The ultrasonic waveform data sent from the A/D converter 411 is written into the ultrasonic waveform memory 412 in write steps (S12, S22, and S32 of FIG. 16), and, in read steps (S13, S23, and S33 of FIG. 16), the ultrasonic waveform data stored in the ultrasonic waveform memory 412 is read therefrom and is connected to the adder 53. An address of the ultrasonic waveform memory 412 is supplied from the switch 413.

The switch 413 sends a value of the beam path length counter 50 to the address of the ultrasonic waveform memory 412 in write steps (S12, S22, and S32 of FIG. 16), and, in read steps (S13, S23, and S33 of FIG. 16), the switch 413 sends the contents of the dynamic focusing phase correction memory 414 to the address of the ultrasonic waveform memory 412.

The above-described beam path length counter 50 is a counter specifying the range in a depth direction of data to be captured in the waveform memory.

In the dynamic focusing phase correction memory 414, the amount of phase correction in each focus position, the amount of phase correction to which each angle of incidence $\theta$ described above is added, in a well-known dynamic focusing method is stored. By supplying data of the Y direction counter 51, the data indicating a pseudo electronic scanning position y, and data of the D depth direction counter 52, the data indicating a depth position d of focus, to an address of the dynamic focusing phase correction memory 414, the amount of phase correction in a focus position (y, d) is obtained, and the amount of phase correction thus obtained is provided to a read address of the ultrasonic waveform memory 412. From the ultrasonic waveform memory 412, ultrasonic waveform data to which the transducer contributes when dynamic focusing is performed in the focus position (y, d) is obtained. The above procedure is performed by the signal processing circuits 41-1 to 41-$n$ simultaneously, and the contents of the ultrasonic waveform memory 412 of each of the signal processing circuits 41-1 to 41-$n$, that is, the ultrasonic waveform data, are sent to the adder 53, wherein dynamic focusing phase combining is performed. Incidentally, the contents of each dynamic focusing phase correction memory 414 are stored in advance in the focus setting section of the control section 90 via a second signal line (not shown).

Moreover, the pseudo electronic scanning position y of the Y direction counter 51 corresponds to a position in which a transducer is arranged.

As mentioned above, the amount of correction held by the focus setting section is the amount to which the amount of correction of the angle, the amount set in the reception processing setting section 92, is added.

That is, for the above-described focus setting section, the control section 90 adds a pattern (a delay pattern) including the amounts of correction based on the normal beam, the amounts of correction for obtaining the angles of incidence according to the angles of refraction at the indicator points, the amounts set in the reception processing setting section 92 in advance, and a pattern (a delay pattern) including the amount of phase correction required for the focus, and makes the focus setting section hold the pattern of the amount of correction obtained by the addition.

As mentioned above, the reception delay pattern holding section of the reception processing setting section 92 holds a delay pattern of reception processing according to the angle of incidence set with consideration given to the angle of refraction of the material being tested. As a result of the overall control section 100 having being operated in advance by the operator, the reception delay pattern holding section accepts the input of the material of the material being tested, the temperature of the flaw detection water, and the above-described angle ϕ in oblique flaw detection, and, from the delay patterns held by the reception delay pattern holding section, a corresponding reception delay pattern is selected, and the selection result, that is, setting of the pattern, is held in the selection holding section of the reception processing setting section 92.

The amount of correction of the angle is provided to the above-described focus setting section by the control section 90, after setting that angle and before performing flaw detection, by referring to the selected delay pattern for angle correction from the reception delay pattern holding section and the selection holding section of the reception processing setting section 92.

One correction value is provided to a memory corresponding to a beam of one transducer. Therefore, each of the correction values provided to memories corresponding to a plurality of beams performing oblique flaw detection forms one delay pattern (for angle correction).

Each correction value forming the delay pattern is a difference from the reference which is a normal beam whose angle of refraction and angle of incidence are 0 degree, the difference for obtaining the angle of incidence $\theta$ at each incident point, the angle of incidence $\theta$ set with consideration given to the angle of refraction by Snell's law described earlier, and is provided as a delay amount corresponding to the reference. The setting of the angle of incidence with consideration given to the angle of refraction is as described above.

As described above, the control section 90 makes the focus setting section hold a delay pattern obtained by adding, to the above-described delay pattern for angle correction, the above-described correction pattern for obtaining focus in an intended position (an open circle in FIGS. 11 to 13, 14, and 15). The delay pattern for angle correction is added to a focusing delay pattern for each of focal rows forming DDF. The focusing delay pattern for each of focal rows is a delay pattern corresponding to a plurality of angles according to the depth (the depth of the central beam). In oblique flaw detection in this embodiment shown in FIGS. 14 and 15, since DDF is not formed, only the delay pattern for angle correction for obtaining the focus at the indicator point suffices. In this case, as the operation of the equipment, it is necessary simply to select a pattern in which the focus of DDF is one point on the adjacent section.

Moreover, as mentioned above, each focal row is a group of beams formed by virtual transducers (in reading from the memory) for obtaining one dynamic focusing. Here, a case where the focus is provided only on the adjacent section b1-b2 shown in FIGS. 14 and 15 is also regarded as DDF in which only one focus is set as described above, and the concept of focal row is also used in such a case.

The adder 53 performs phase combining on the ultrasonic waveform data sent from as many ultrasonic waveform memories 412 as n elements. An output of the adder 53 is sent to the detector circuit 54. In the detector circuit 54, detection processing such as full-wave rectification, positive half-wave rectification, or negative half-wave rectification is performed. An output of the detector circuit 54 is connected to the gate circuit 60 and the waveform peak storage circuit 70.

The gate circuit 60 includes an echo height memory 61, a comparator 62, a write control circuit 63, an echo depth memory 64, a gate generation circuit 65, a gate position memory 66, and an evaluating section (not shown).

The gate circuit 60 sets a range of the waveform data detected by the detector circuit 54, the range in which the presence or absence of a defect is determined in a beam path length, and determines the presence or absence of a defect in that range.

The gate circuit 60 actively operates only in read steps S13, S23, and S33 (FIG. 16), and, in control section update steps S15, S25, and S35 (FIG. 16), only access to the memory 61 and the memory 64 is performed.

The echo height memory 61 temporarily stores an in-gate peak echo height in each position of a pseudo electronic scanning position y by using, as an address, the Y direction counter 51 indicating a pseudo electronic scanning position y. The comparator 62 compares the echo height value of the detector circuit 54 with the in-gate peak echo height stored in the echo height memory 61, and, when the echo height value of the detector circuit 54 is higher than the in-gate peak echo height, the comparator 62 sends a write signal to the write control circuit 63. The write control circuit 63 receives the gate signal of the gate generation circuit 65, and, when the write signal of the comparator 62 is inputted while the gate is on, the write control circuit 63 sends a write pulse to the echo height memory 61 and the echo depth memory 64. Having received this pulse, the echo height memory 61 writes the echo height value, which is the output data of the detector circuit 54 into the echo height memory 61, and updates the in-gate peak echo height in the echo height memory 61. In the control section update step S15 (FIG. 16), while the Y direction counter 51 indicating the pseudo electronic scanning position y is being incremented from 0 by +1, the in-gate peak echo heights in the echo height memory 61 are sequentially read. After reading, the contents of the memory are cleared, and preparations for the next cycle (flaw detection in the next cross-section position) are made.

The echo depth memory 64 temporarily stores an in-gate peak depth position in each position of a pseudo electronic scanning position y by using, as an address, the Y direction counter 51 indicating a pseudo electronic scanning position y. The write signal from the above-mentioned write control circuit 63 also serves as the write pulse of the echo depth memory 64. When this write pulse is inputted, in the echo depth memory 64, the value of the D depth direction counter 52 indicating a depth position d of focus is written into the memory, and the in-gate peak depth position stored in the echo depth memory 64 is updated. In the control section update step S15 (FIG. 16), while the Y direction counter 51 indicating the pseudo electronic scanning position y is being incremented from 0 by +1, the in-gate peak depth positions in the echo depth memory 64 are sequentially read. After reading, the contents of the memory are cleared, and preparations for the next cycle are made.

The gate position memory 66 stores gate starting point position data and gate end point position data in the depth direction in each position of a pseudo electronic scanning position y by using, as an address, the Y direction counter 51 indicating a pseudo electronic scanning position y. When the Y direction counter 51 indicating a pseudo electronic scanning position y is updated, the contents of the gate position memory 66 are read, and the values of a gate starting point position and a gate end point position in the depth direction, the values determined by the position of a pseudo electronic scanning position y, are sent to the gate generation circuit 65.

The contents of the gate position memory 66 are provided from the control section 90 via a third signal line (not shown), and are stored in advance in a gate storing section of the control section 90. When a delay pattern formed of the correction value providing the above-described angle of incidence θ is set in the selection holding section of the reception processing setting section 92 by the overall control section 100, the control section 90 reflects the reception delay pattern in the gate starting point position data and the gate end point position data in the depth direction of the gate storing section by referring to the reception delay pattern holding section and the angle holding section of the reception processing setting section 92.

More preferably, the control section 90 includes a gate calculating unit (not shown) and sets a gate for each focal row.

Specifically, the gate calculating unit includes an S echo synchronizing unit and a gate extreme point calculating unit. The S echo synchronizing unit multiplies an S echo (a reflected wave on the surface of the material being tested) obtained by actual transmission of the ultrasonic waves at the time of vertical flaw detection by a percentage of the water distance (the distance between the transducer and the material being tested, the distance filled with the flaw detection water) in each incident position of the ultrasonic waves at the time of transmission in oblique flaw detection, and thereby calculates a pseudo S echo position in each incident position in oblique flaw detection. The gate extreme point calculating unit calculates a predetermined percent position of the beam path length of the central beam of each focal row as a starting point of a gate (a gate start point), and, likewise, calculates a predetermined percent position of the beam path length of the central beam as an end point of the gate (a gate end point). For example, the gate extreme point calculating unit calculates a 50% position of the beam path length (the round-trip time) of the central beam as a gate start point and a 150% position of the beam path length (the round-trip time) of the central beam as a gate end point. Since the beam path lengths differ from focal row to focal row, the calculation values obtained by the gate calculating unit are different.

The control section 90 makes the gate storing section hold the contents calculated in this way.

The gate generation circuit 65 receives the values of the gate starting point position and the gate end point position in the depth direction, the values sent from the above-mentioned gate position memory 66, and compares the two values with the value of the D depth direction counter 52 indicating a depth position d of focus. When the D depth direction counter 52 is located between the two gate positions, the gate signal is turned on; otherwise, the gate signal is turned off, and the gate signal is sent to the write control circuit 63.

The evaluating section holds data on the peak height regarded as a defective echo, and determines the presence or absence of a defect by comparing the in-gate peak echo height in the echo height memory 61 with the above-described held peak height between the gate positions. The evaluating section outputs a signal indicating the determination result to a sorting unit sorting the materials being tested on the production line into non-defective items and defective items.

The waveform peak storage circuit 70 is made up of a waveform peak storage memory 71, a comparator 72, a register 73, a comparator 74, and a write control circuit 75. To an address of the waveform peak storage memory 71, the D depth direction counter 52 indicating a depth position d is connected, and an ultrasonic wave echo waveform at each depth is stored.

The comparator 72 compares the echo height value of the detector circuit 54 with the contents of the waveform peak storage memory 71, and, when the echo height value of the detector circuit 54 is higher than the contents of the waveform peak storage memory 71, sends a write signal to the write control circuit 75.

The register 73 holds the contents of a Y direction electronic scanning address ys, and the waveform peak storage circuit 70 holds the maximum value at each depth on a scanning line of this address ys. The data of the register 73 is written by the control section 90.

The comparator 74 compares the contents (ys) of the register with the Y direction counter 51 indicating an electronic scanning position y, and, when the contents (ys) of the register 73 match the Y direction counter 51, sends an electronic scanning position matching signal to the write control circuit 75.

When a write signal is inputted from the comparator 72 while the electronic scanning position matching signal is being inputted from the comparator 74, the write control circuit 75 outputs a write pulse to the waveform peak storage memory 71. Having received this write pulse, the waveform peak storage memory 71 writes the output data of the detector circuit 54 into the memory, whereby the memory contents are updated.

In a display and communication step S40 (FIG. 16), while the D depth direction counter 52 indicating a depth position d is being incremented from 0 by +1, the ultrasonic waveforms stored in the waveform peak storage memory 71, i.e., the A scope waveforms, are sequentially read. After reading, the contents of the memory are cleared, and preparations for the next cycle are made. Then, the A scope waveforms thus read are displayed on the screen display section in the control section 90.

The waveform peak storage circuit 70 makes the screen display section 110 display an image that allows the operator to monitor the status of flaw detection. Therefore, all that is required is to determine the acceptability of a product (a material m being tested), that is, to sort out the products to be regarded as defective items due to the presence of a defect. When there is no need for monitoring by the operator, the embodiment can also be implemented without providing the waveform peak storage circuit 70 and the screen display section 110.

Next, the operation of the invention will be explained by using FIG. 16.

In FIG. 16, a flow (a process chart) of one flaw detecting unit k is shown. Each of the flaw detecting units k1 to k6 adopts the same flow as that shown in FIG. 16.

Hereinafter, FIG. 16 will be explained as a flow of the first flaw detecting unit k1.

A flaw detection process of this equipment, the process shown in FIG. 16, includes steps S11 to S15 for vertical flaw detection of the counter section a1-a2, steps S21 to S25 for one oblique flaw detection (positive oblique flaw detection), steps S31 to S35 for the other oblique flaw detection (negative oblique flaw detection), and a display and communication step S40.

That is, the flaw detection process includes, as a process for vertical flaw detection, a vertical flaw detection emission step S11, a vertical flaw detection write step S12, a vertical flaw detection read step S13, a vertical flaw detection gate evaluation processing step S14, and a control section update step S15. Moreover, the flaw detection process includes, as a process for oblique flaw detection (positive oblique flaw detection) of the above-described right adjacent section b1-b2, a positive oblique flaw detection emission step S21, a positive oblique flaw detection write step S22, a positive oblique flaw detection read step S23, a positive oblique flaw detection gate evaluation processing step S24, and a control section update step S25. Furthermore, the flaw detection process includes, as a process for oblique flaw detection (negative oblique flaw detection) of the above-described left adjacent section c1-c2, a negative oblique flaw detection emission step S31, a negative oblique flaw detection write step S32, a negative oblique flaw detection read step S33, a negative oblique flaw detection gate evaluation processing step S34, and a control section update step S35.

As described above, an explanation is given on the assumption that the first flaw detecting unit k1 performs flaw detection processing in an order of: vertical flaw detection of the counter section a1-a2 of the material m being tested, oblique flaw detection of one adjacent section b1-b2, and oblique flaw detection of the other adjacent section c1-c2. However, the above order can be changed.

As shown in FIG. 16, when processing of the steps S11 to S35 is completed, the procedure is shifted to flaw detection in another position in an axial direction (a direction E in FIG. 2) of the material m being tested, and the steps S11 to S35 are repeated.

The display and communication step S40 is performed when needed.

Each step will be explained in turn.

In the vertical flaw detection emission step S11, one pulse emission timing signal is generated by the control section 90 by referring to the transmission delay pattern holding section and the selection holding section of the transmission processing setting section 91, and is sent to the pulser section 20.

Having received this signal, the pulser section 20 sends a spike pulse concurrently to the n ultrasonic transducers of the ultrasonic transducer array 10. As a result, the ultrasonic transducers are excited according to the delay pattern set as described above, and the ultrasonic waves are emitted as cylindrical waves toward the counter section a1-a2. The ultrasonic waves propagate through the testing space, and, when the ultrasonic waves run into an acoustic reflecting surface such as a defect, a part of the ultrasonic waves is reflected and is received by the ultrasonic transducer array 10.

In the vertical flaw detection write step S12, the ultrasonic wave received echoes of the transducers, the ultrasonic wave received echoes received by the ultrasonic transducer array 10, are amplified by the receiver section 30 and sent to as many signal processing circuits 41-1 to 41-n as n transducers. In each signal processing circuit 41, the ultrasonic wave received echo is subjected to analog-to-digital conversion and stored in the ultrasonic waveform memory 412. A memory address at that time is provided by the beam path length counter 50, and the clock of the beam path length counter 50 is the same as the clock of the A/D converter 411. For example, in this embodiment, a nominal frequency of the ultrasonic transducer is set to 5 MHz or less, and the clock of analog-to-digital conversion is set to 50 MHz. However, the frequency is not limited thereto, and can be changed when needed.

In general, the beam path length counter 50 is cleared to 0 at the time at which the ultrasonic waves are emitted, and counting is then performed by the clock of the A/D converter. When the starting point of the electronic scanning range is far away, the time at which the counter is cleared to 0 is appropriately controlled by the control section. This makes it possible to use the capacity of the ultrasonic waveform memory 412 effectively. This step is performed until the maximum beam path length propagation time in the electronic scanning range.

In the vertical flaw detection read step S13, while the ultrasonic wave received echo waveform stored in the ultrasonic waveform memory 412 is being read, pseudo electronic scanning is performed on a depth direction D and a probe array direction Y of the testing space by a dynamic focusing method. An image diagram of pseudo electronic scanning is shown in FIG. 17. In this drawing, an ultrasonic transducer array and a pseudo electronic scanning plane surface indicated by an interval from a depth d0 to a depth de (of the central beam) in the testing space in which the ultrasonic waves of the ultrasonic transducer array are emitted and an interval from y0 to ye in a probe array direction Y direction are shown.

In the vertical flaw detection read step S13, the Y direction counter 51 and the D depth direction counter 52 are cleared or set to the starting positions y0 and d0. Then, the Y direction counter 51 is incremented until the counter value becomes ye. When the counter exceeds ye, the Y direction counter is then cleared or set to the starting position y0, and the D depth direction counter 52 is incremented by +1. The above operation is repeatedly performed until the D depth direction counter 52 indicates de and the Y direction counter 51 reaches the end point at this position. The above operation is performed with the clocks of the counter 51 and the counter 52 set at 50 MHz, which is the same as the clock of analog-to-digital conversion. In the meantime, in the signal processing circuits 41-1 to 41-n, the values of the Y direction counter 51 and the D depth direction counter 52 are provided to the address of the dynamic focusing phase correction memory 414. From the dynamic focusing phase correction memory 414, the amount of phase correction of each of the ultrasonic transducers (from 1 to n) at the electronic scanning position (y, d), the amount of phase correction to be subjected to phase combining, that is, the beam path length position, is outputted. Furthermore, the beam path length position serves as the read address of the ultrasonic waveform memory 412. The contents of the focusing phase correction memory 414 are the contents of the focus setting section, the contents stored by referring to the reception processing setting section 92.

The beam path length position is illustrated by two arrows L1 and L2 at a pseudo electronic scanning position P1 on the pseudo electronic scanning image of FIG. 17. Here, L1 represents a propagation path via which the ultrasonic waves reach the pseudo electronic scanning position P1 first; in general, it is a distance between the pseudo electronic scanning position P1 and a transducer closest to the pseudo electronic scanning position P1. Moreover, L2 represents a propagation path of the ultrasonic waves received by each transducer (illustrated as a transducer position n in FIG. 17) when the ultrasonic waves are reflected at the pseudo electronic scanning position P1. The sum of the two propagation paths (L1+L2) becomes the beam path length position when phase combining is performed in the transducer n at the pseudo electronic scanning position P1. Therefore, from the ultrasonic waveform memory 412, the ultrasonic waveform data in each ultrasonic transducer, the ultrasonic waveform data to be subjected to phase combining at the pseudo electronic scanning position (y, d), is outputted. This ultrasonic waveform data is outputted from each of as many signal processing circuits 41-1 to 41-n as the ultrasonic transducers, is sent to the adder 53, wherein phase combining is performed. By the above procedure, the waveform obtained by the phase combining at the pseudo electronic scanning position (y, d) indicated by the Y direction counter 51 and the D depth direction counter 52 is outputted from the adder 53. The above relationship is shown in FIGS. 17 and 18. Point P1 and point P2 in FIG. 17 represent two points on a plane surface subjected to electronic scanning, and addresses (y1, d1) and (y2, d2) of the two points represent the D depth direction counter 52 and the Y direction counter 51 at that time. FIG. 18 shows an address and a memory of each ultrasonic waveform memory 412, and shows a phase compound curve of each ultrasonic waveform memory 412 at two points P1 and P2 on the pseudo electronic scanning plane surface; in phase combining, the contents of the memories 412 are read concurrently along this curve, and are subjected to phase combining by the adder 53. Here, such a method is referred to as a dynamic focusing method by the pseudo electronic scanning plane surface. While dynamic focusing by the pseudo electronic scanning plane surface is performed, the adder 53 outputs the phase combining result data at each pseudo electronic scanning position, and the data is sent to the gate circuit 60 and the waveform peak storage circuit 70 via the detector circuit 54.

In the gate circuit 60, the in-gate waveform peak echo height and the depth direction position thereof are detected. As shown in FIG. 17, the gate range can be set for each Y scanning position, and the waveform peak echo height and the beam path length thereof at each Y scanning position can be detected. The gate position memory 66 has the gate range data at each Y scanning position, the gate range data written thereinto in advance. In dynamic focusing by the pseudo electronic scanning plane surface in the read step S13, the value of the Y direction counter 51 indicating a y position on the pseudo electronic scanning plane surface is provided to the address of the gate position memory 66. The memory contents of the gate position memory 66 correspond to the gate range data (a starting point gs and an end point ge) at the y position, and the data is connected to the gate generation circuit 65. The gate generation circuit 65 compares the gate range data with the D depth direction counter 52 indicating a d position on the pseudo electronic scanning plane surface, and, when the d position is within the gate range, sends a gate on signal to the write control circuit 63. As described above, the contents of the gate position memory 66 are the contents of the gate position storing section of the control section, and the contents of correction in the reception processing setting section 92 are reflected therein.

While the gate is on, the comparator 62 compares the previous in-gate peak echo height stored in the echo height memory 61 with the echo height at the current pseudo electronic scanning position, the echo height from the detector circuit 54. When the echo height at the current pseudo electronic scanning position is higher than the previous in-gate peak echo height, the comparator 62 writes the echo height at the current pseudo electronic scanning position into the echo height memory 61, and writes data of the D depth direction counter 52 indicating the d position of the current pseudo electronic scanning position into the echo depth memory 64.

Since the Y direction counter 51 indicating the y position on the pseudo electronic scanning plane surface is provided to the addresses of the echo height memory 61 and the echo depth memory 64, it is possible to store the in-gate waveform peak echo height and the depth direction position thereof at each y position.

Incidentally, FIG. 17 shows an image of a temporal relation in pseudo electronic scanning, and the gate shown in FIG. 17 is not actually set on the memory.

In the waveform peak storage circuit 70, waveform peak storage processing is performed on the ultrasonic waveform on a virtual flaw detection line whose Y position on the pseudo electronic scanning plane surface shown in FIG. 17 is ys. This ultrasonic waveform is displayed on the screen display section of the personal computer, and, in general, the display cycle thereof is long and is about 20 msec (in terms of frequency, in the neighborhood of 50 Hz). Compared to this, in the above-described equipment of the invention, the cycle in which the entire range of the pseudo electronic scanning plane surface is scanned is shorter than the above display cycle, and therefore it is impossible to display all the ultrasonic waveforms on the virtual flaw detection line. It is for this reason that the waveform peak storage circuit 70 stores the peak height of the ultrasonic waveform at each depth position in each ultrasonic waveform on the virtual flaw detection line in a display cycle, and stores the maximum waveform at all the depth positions. Into the register 73, data (ys) indicating the Y position on the virtual flaw detection line is written by the control section 90. This data is sent to the comparator 74. The comparator 74 compares the Y direction counter 51 indicating the electronic scanning position y with this register 73 (ys), and, when there is a match between them, outputs a matching signal to the write control circuit 75, and the following operation is effectively performed. That is, the D depth direction counter 52 indicating a depth position d is connected to the address of the waveform peak storage memory 71, the previous ultrasonic wave peak waveform at the same depth position d is provided to the comparator 72 from the waveform peak storage memory 71, and the latest ultrasonic waveform echo height at the same depth position d is provided thereto from the detector circuit 54. When the ultrasonic waveform echo height from the detector circuit 54 is higher than the other, a write signal is sent to the write control circuit 75, and the write control circuit 75 sends a write pulse to the waveform peak storage memory 71, whereby the ultrasonic wave peak waveform at the depth position d is updated to an echo height higher than the last one. The above operation is performed at each depth, and is performed in the same manner in each read step S13 of the flaw detection cycles occurring one after another.

In step S14 of vertical flaw detection gate evaluation processing, the evaluating section compares the in-gate peak echo height in the echo height memory 61 with the above-described held peak height between the gate positions, and determines the presence or absence of a defect. The evaluating section outputs a signal indicating the determination result to a sorting unit sorting the materials being tested on the production line into non-defective items and defective items.

In the control section update step S15, the control section 90 reads the contents of the echo height memory 61 and the echo depth memory 64 of the gate circuit 60 while operating the Y direction counter 51 to which the addresses of the memory 61 and the memory 64 are provided, and clears the contents of the memories after reading the contents thereof.

After the above-described control section update step S15, the procedure proceeds to the positive oblique flaw detection emission step S21.

In the positive oblique flaw detection emission step S21, the control section 90 generates one pulse emission timing signal by referring to the transmission delay pattern holding section and the selection holding section of the transmission processing setting section 91, and the pulse emission timing signal is sent to the puller section 20. In the positive oblique flaw detection, a pattern according to each angle of incidence set as described above is set to make the ultrasonic waves diverge after converging on the focus Fl and then reach the adjacent section b1-b2.

In the vertical flaw detection, it is necessary to set a delay pattern, which is symmetrical with respect to the perpendicular bisector Q2. In the positive oblique flaw detection, in place of such a symmetrical delay pattern, a delay pattern by which the focus Fl is obtained in a position with the perpendicular bisector Q2 on the right side thereof is set.

By setting such a delay pattern, the ultrasonic waves can make the cylindrical waves, which converge on the focus Fl and then diverge reach the adjacent section b1-b2. This step S21 is the same as the above-described emission step S11 in the vertical flaw detection except for the above-mentioned respects.

Moreover, processing in the positive oblique flaw detection write step S22 is the same as the processing in the above-described vertical flaw detection write step S12.

Also in the positive oblique flaw detection read step S23, the same processing as in the vertical flaw detection read step S13 is performed. Specifically, since this is oblique flaw detection, the contents of the focusing phase correction memory 414 are the contents to which a delay pattern is added, the delay pattern set according to each angle of incidence set with consideration given to the angle of refraction, the delay pattern for obtaining the focus for each focal row, that is, obtaining the focus on the indicator point in oblique flaw detection. As described earlier, in the oblique flaw detection of this embodiment, original DDF is not performed. Therefore, no correction to obtain a plurality of DDF focuses in the depth direction is necessary, and this delay pattern is formed of a correction value making the beams forming the same focal row have the same path length and providing each beam with the angle of incidence set with consideration given to the angle of refraction in each position.

Moreover, the contents of the gate position memory 66 are the contents in which the contents of the gate storing section of the reception processing setting section 92 are reflected, and hold data of the aforementioned gate start and gate end, the data calculated by the S echo synchronizing unit and the gate extreme point calculating unit of the gate calculating unit.

Based on the contents of the focusing phase correction memory 414 and the gate position memory 66 according to the said angle φ, in the positive oblique flaw detection read step S23, the same processing as in the vertical flaw detection read step S13 is performed.

Also in step S24 of positive oblique flaw detection gate evaluation processing, based on the above-described contents of the gate position memory 66, the contents in which correction of the angle is reflected, the same evaluation processing as in the above-described step S14 of vertical flaw detection gate evaluation processing is performed.

In the control section update step S25, as in the control section update step S15, the control section 90 reads the contents of the echo height memory 61 and the echo depth memory 64 of the gate circuit 60 while operating the Y direction counter 51 to which the addresses of the memory 61 and the memory 64 are provided, and clears the contents of the memories after reading the contents thereof.

In the negative oblique flaw detection emission step S31, the negative oblique flaw detection write step S32, the negative oblique flaw detection read step S33, the negative oblique flaw detection gate evaluation processing step S34, and the control section update step S35, which are included in the other oblique flaw detection (negative oblique flaw detection) process, the delay pattern set in the reception processing setting section 92 is formed of a correction value whose positive and negative are opposite to those of the delay pattern in each step of the oblique flaw detection (positive oblique flaw detection) of the above-described right adjacent section. Except for this point, processing in each step of the other oblique flaw detection (negative oblique flaw detection) described above is the same as the processing in each step of the one oblique flaw detection (positive oblique flaw detection).

In the display and communication step S40, a judgment as to whether screen display is updated or not is made. When update of the screen is not performed, the processing in the step S40 is ended; when update of the screen is performed, the control section 90 reads the contents of the waveform peak storage memory 71 of the waveform peak storage circuit 70 while operating the D depth direction counter 52 to which the address of the memory 71 is provided, and clears the contents of the memory after reading the contents thereof. Then, the control section 90 displays the values of each in-gate echo height and each echo depth read in the control section update steps S15, S25, and S35, and transmits the contents thereof to the outside. Moreover, the control section 90 displays the ultrasonic waveform read in the control section update steps S15, S25, and S35, the ultrasonic waveform whose peak has been stored, on the screen display section as an A scope waveform, and transmits the waveform data thereof to the outside.

Incidentally, this embodiment deals with only one gate circuit 60; however, the invention is not limited thereto. It is also possible to prepare a plurality of gate circuits and add gate processing in a plurality of gate ranges other than that described above.

As described above, in the above-described ultrasonic flaw detection equipment of the invention, a transmission pulse in the form of a spike pulse is transmitted to each transducer of the ultrasonic transducer array with timing according to vertical flaw detection or oblique flaw detection, and the received ultrasonic wave echo received by each transducer is subjected to analog-to-digital conversion and is stored in as many waveform memories as the transducers. In pseudo electronic scanning, waveform data is read concurrently from as many waveform memories as the transducers along a phase compound curve at the position, and is subjected to phase combining. That is, a waveform at one scanning position of pseudo electronic scanning, the waveform subjected to phase combining, is obtained in one memory read cycle. In this embodiment, since a clock of 50 MHz is used, calculation at one point is completed in 20 nsec. In the case of a pseudo electronic scanning plane surface with 200 points in a depth direction and 200 points in a Y axis direction, it takes 20*200*200 nsec=800 μsec to scan the entire range thereof. Moreover, while the pseudo electronic scanning is performed, gate processing in the gate circuit and A scope waveform storage processing in the waveform peak storage circuit are performed concurrently. As an ultrasonic repeating cycle, in addition to 800 μsec described above, the ultrasonic wave emission time, the ultrasonic wave reception time, and the time to read the gate data and the A scope waveform are required; when it is assumed that the time is about 200 μsec, the flaw detection cycle in the above-described pseudo electronic scanning range is completed in 1000 μsec (=1 msec). With the equipment of the conventional technique in which a flaw detection beam is electronically moved in the Y direction and measurement is performed in the depth direction by the dynamic focusing method, flaw detection in one beam direction is completed in one ultrasonic repeating cycle, and therefore 200 ultrasonic repeating cycles are required to perform flaw detection in the same pseudo electronic scanning range as described above. Even when the ultrasonic repeating frequency is set at 10 KHz, it takes 20 msec to perform flaw detection in the above-described pseudo electronic scanning range. In this embodiment, the above-described equipment of the invention can perform flaw detection 20 times as fast as the equipment of the conventional technique.

The above-described embodiment deals with a case where, as for the order in which processing in the Y direction and processing in the D direction in electronic scanning are performed, the Y direction counter 51 is first incremented, and the D depth direction counter 52 is then incremented after the Y direction counter 51 reaches the end point. However, the embodiment can also be so implemented that the D depth direction counter 52 is first incremented, and the Y direction counter 51 is then incremented after the D depth direction counter 52 reaches the end point.

As described above, this equipment detects the position of an internal defect of a corresponding material being tested by, as volume focusing flaw detection, stopping the setting of the actual focus of the ultrasonic waves at the time of transmission of the ultrasonic waves in a flaw detection region, bringing the positions in the material being tested, the material to be subjected to flaw detection, into correspondence with the addresses of waveform memories, and obtaining the address of an abnormal waveform memory by comparing phase combining of waveform data at the waveform memory positions with each other, the phase combining achieved by electrical processing at the time of actual reception. By doing so, this equipment makes it possible to perform high-speed flaw detection by obtaining a wide flaw detection range by cylindrical waves and reducing flaw detection cycles.

That is, the volume focusing method is a method in which ultrasonic waves are emitted widely toward a material being tested by one excitation of a probe on the transmitting side, pseudo electronic scanning is performed on the receiving side without actual scanning (electronic scanning), phase combining is performed on the A scope waveforms, and evaluation is performed.

In the invention, such volume focusing is realized for a material being tested, the material, which is circular as seen in a sectional view, and flaw detection, can be reliably performed without detriment to high-speed processing.

When a line array in which transducers are linearly arranged is used for a material being tested, such as a cylindrical material, which is circular as seen in a sectional view, the line array used for a material being tested, such as a square billet, which has a linear surface as seen in a sectional view, it is necessary to provide a correction value set with consideration given to the radius of curvature (the diameter of a circle) of the surface of the material being tested in order to generate the cylindrical waves described above and perform pseudo electronic scanning on the receiving side. By contrast, in the invention, since the transducers are arranged in an arc along the circumference of a circle exhibited by the material being tested, there is no need to make consideration to detect a defective echo, and it is possible to detect a defective echo by the same transmission and reception processing as in flaw detection performed on a square billet by using a line array. However, the correction described above is required to set the focus at the time of transmission in a position other than the core O. Moreover, when an arc exhibited by a group of transducers of each array probe 10 is not concentric with the core O of the material m being tested, a pattern of a correction value for correcting it has to be added to the above-described pattern of a correction value.

In this embodiment, flaw detection can be performed by transmissions performed three times and is not affected by a ghost, making it possible to increase the pulse density in the direction of the longer sides of a billet. Furthermore, by performing flaw detection in combination with DDF, it is possible to enhance detection capability over a wide region of the cross section. In flaw detection of a material being tested having a diameter of 60 mm, it is possible to achieve a pulse density of 5 mm or less at a transport speed of 120 m/min. By adopting the volume focusing flaw detection, it becomes possible to perform testing with extremely high detection capability and processing capability as compared with the conventional method.

It is clear from an A scope image of vertical flaw detection, the image shown in FIG. 21(A) and obtained by the equipment of this embodiment, that a defect v1 in FIG. 1 appears as w1 by vertical flaw detection, and it is clear from an A scope image of oblique flaw detection, the image shown in FIG. 21(B), that a defect v2 in FIG. 1 appears as w2 by oblique flaw detection.

In actual flaw detection of a material being tested, it is necessary to perform calibration prior to flaw detection. In calibration, calibration of the sensitivity of a probe and DAC calibration are performed. In the flaw detection method according to the invention, in sensitivity calibration, by using data on test pieces, which has been obtained by actually performing calibration, calibration data on a test piece having a size intermediate between the sizes of these test pieces is obtained without performing actual sensitivity calibration.

For example, actual sensitivity calibration operation has been performed by using a test piece (a cylindrical material) having a diameter of 40 mm and a test piece having a diameter of 60 mm, and data on the sensitivity to be set for the materials being tested, the materials having these diameters, has already been obtained. Specifically, when it has been found out by actual calibration that the sensitivity of the first focal row of the test piece having a diameter of 40 mm is 30 dB and the sensitivity of the first focal row of the test piece having a diameter of 60 mm is 36 dB, the sensitivity of the first focal row of a test piece having a diameter of 50 mm is set at $(30+36)\div 2=33$ dB by adopting the average value of the sensitivity data of 40 mm and 60 mm instead of actually performing calibration on the test piece having a diameter of 50 mm which is a diameter intermediate between the diameters of the above two test pieces. Moreover, as for a gate, similar complementary processing is performed. In short, when the outside diameter changes, complementary processing is needed for both sensitivity and a gate.

As described above, this flaw detection method can reduce the number of test pieces to be prepared by obtaining, by calculation as described above, data on a test piece on which no calibration operation is performed by using the sensitivity data on a test piece having a diameter which is a size larger than that of the test piece on which no calibration operation is performed and a test piece which is a size smaller than that of the test piece on which no calibration operation is performed.

In this equipment, when any one of the above-described flaw detecting units k1 to k6 detects a defective echo as a result of flaw detection performed by the six flaw detecting units k1 to k6, the material being tested is judged to be a defective item. However, the embodiment can also be so implemented that a judgment as to whether the material being tested is a non-defective item or a defective item is made by considering the results of flaw detection performed by the flaw detecting units k1 to k6 together.

Moreover, the above embodiment deals with a case where the oblique flaw detection apparatus doubles as the vertical flaw detection apparatus; however, the embodiment can also be so implemented that the oblique flaw detection apparatus and the vertical flaw detection apparatus are provided separately, and the array probes of these apparatuses are disposed separately on the surface of the material being tested.

Furthermore, the above embodiment deals with a case where the six flaw detecting units k1 to k6 are used; however, other than six flaw detecting units k, for example, two to five or seven or more flaw detecting units k may be used. Accordingly, the embodiment can be implemented by providing, other than six array probes 10, two to five or seven or more array probes 10. It is necessary simply to select the focus positions of the array probes according to the number of array probes. For example, when the number of array probes 10 is reduced from six which is the number in the above description, by making the lengths of the counter section and the adjacent section longer than the lengths thereof in a case where six probes are used by selecting the focus positions of the array probes 10, flaw detection can be thoroughly performed on every part of the material being tested even with a smaller number of probes. On the contrary, when the embodiment is implemented by providing more than six probes unlike in the above description, it is possible to set a narrower flaw detection range of each probe. However, from a cost standpoint, it is preferable to reduce the number of array probes 10 to a minimum. By implementing the invention, it is possible to reduce the number of such array probes to a minimum.

The invention claimed is:

1. An ultrasonic flaw detection equipment for performing a volume focusing flaw detection of a material being tested, the material having a substantially circular cross-sectional shape, the ultrasonic flaw detection equipment comprising:
    at least two array probes, each of the at least two array probes arranged along a surface of the material, each of the at least two array probes having a plurality of transducers, wherein the plurality of transducers of each array probe are arranged in an arc along a circle exhibited by the material being tested, and array probes are disposed so as to surround the material being tested;
    an exciting unit configured to excite each transducer of the array probes;
    a waveform memory configured to store an ultrasonic wave received echo received by each transducer as waveform data of each transducer;
    a phase combining unit configured to read contents of the waveform memory in which the waveform data of each transducer is stored and perform phase combining; and
    a focusing unit configured to provide, in reading from the waveform memory, an address of each waveform memory as an address corresponding to a beam path length of dynamic focusing for an arbitrary position in a pseudo electronic scanning range of a pseudo electronic scanning, wherein the ultrasonic flaw detection equipment is configured to transmit ultrasonic waves toward the material being tested from all the transducers of the array probes at a time, receive reflection echoes thereof by all the transducers, combine A scope waveforms of elements, the A scope waveforms being stored in the waveform memory, by the phase combining unit, and perform evaluation, wherein the ultrasonic flaw detection equipment is configured to perform a vertical flaw detection and an oblique flaw detection, for each array probe, the exciting unit is configured to excite the transducers to emit ultrasonic waves, the ultrasonic waves entering the material from an incident section, which is a section on a circumference of the circle exhibited by the material being tested, along which the array probe is placed, and reaching a counter section on the circumference of the circle exhibited by the material being tested, facing the incident section, so that the plurality of transducers are vibrated once for a first time and the vertical flaw detection is performed, and for each array probe, the exciting unit is configured to excite the transducers, while gradually shifting timing from one end of an arc exhibited by an array toward another end of the arc, to emit ultrasonic waves, the ultrasonic waves entering the material from the incident section and reaching one of adjacent sections adjacent to the counter section on the circumference of the circle exhibited by the material, so that the oblique flaw detection is performed and the plurality of transducers are vibrated once for a second time.

2. The ultrasonic flaw detection equipment according to claim 1, wherein a volume focusing flaw detection method is used at least in the vertical flaw detection method, and in the vertical flaw detection, the exciting unit is configured to excite the transducers of each array probe simultaneously, the transducers having at least a line-symmetric positional relation with respect to a perpendicular bisector of a line segment connecting ends of an arc exhibited by a group of transducers of the array probe in a cross section orthogonal to an axial direction of the material being tested.

3. The ultrasonic flaw detection equipment according to claim 2, wherein the exciting unit is configured to set an actual focus of the ultrasonic waves allowed to enter by the vertical flaw detection on the bisector and between the incident section and a center of the circle exhibited by the material being tested in the cross section, and the exciting unit is further configured to set an actual focus of the ultrasonic waves allowed to enter by the oblique flaw detection inside the material being tested and in a position off the perpendicular bisector, the position closer to the array probe than a line which intersects the perpendicular bisector at a right angle at the center of the circle exhibited by the material being tested, in the cross section.

4. The ultrasonic flaw detection equipment according to claim 2, wherein the pseudo electronic scanning is pseudo scanning performed on a receiving side in place of electronic scanning in which scanning is performed by sequentially exciting the arranged transducers of the array probe along a direction in which the transducers are arranged at a time of transmission of the ultrasonic waves, the pseudo scanning in which the arranged transducers are brought into correspondence with addresses of the waveform memories, data of received waves obtained by exciting all the arranged transducers of the array probe at one time at a time of transmission of ultrasonic waves is recorded on the waveform memories, and, in reading data from the waveform memory, data in the memory is read by sequentially shifting, in a direction corresponding to an electronic scanning direction of the transducer, the address of the memory corresponding to the transducer necessary to form a focus in each position inside the material being tested on the receiving side, and wherein the ultrasonic flaw detection equipment is configured in such a manner that:

in the vertical flaw detection, during pseudo electronic scanning, a direction of an ultrasonic beam of each group of transducers to be shifted is brought into correspondence with each position in the counter section by providing a correction value to the address in reading from the waveform memory, and in the oblique flaw detection, during pseudo electronic scanning, a direction of an ultrasonic beam of each group of transducers to be shifted is brought into correspondence with each position in the adjacent section by providing another correction value to the address in reading from the waveform memory.

5. The ultrasonic flaw detection equipment according to claim 2, comprising:

a gate calculating unit, wherein in oblique flaw detection, the gate calculating unit sets a flaw detection gate for each group of transducers to be shifted during pseudo electronic scanning, the flaw detection gate according to a distance between a transducer and an incident point of the ultrasonic waves from the transducer, the ultrasonic waves entering the material being tested at the incident point, with reference to surface waves obtained by transmission in vertical flaw detection.

6. The ultrasonic flaw detection equipment according to claim 1, wherein the exciting unit is configured to set an actual focus of the ultrasonic waves allowed to enter by the vertical flaw detection on the bisector and between the incident section and a center of the circle exhibited by the material being tested in the cross section, and the exciting unit is further configured to set an actual focus of the ultrasonic waves allowed to enter by the oblique flaw detection inside the material being tested and in a position off the perpendicular bisector, the position closer to the array probe than a line which intersects the perpendicular bisector at a right angle at the center of the circle exhibited by the material being tested, in the cross section.

7. The ultrasonic flaw detection equipment according to claim 6, wherein the pseudo electronic scanning is pseudo scanning performed on a receiving side in place of electronic scanning in which scanning is performed by sequentially exciting the arranged transducers of the array probe along a direction in which the transducers are arranged at a time of transmission of the ultrasonic waves, the pseudo scanning in which the arranged transducers are brought into correspondence with addresses of the waveform memories, data of received waves obtained by exciting all the arranged transducers of the array probe at one time at a time of transmission of ultrasonic waves is recorded on the waveform memories, and, in reading data from the waveform memory, data in the memory is read by sequentially shifting, in a direction corresponding to an electronic scanning direction of the transducer, the address of the memory corresponding to the transducer necessary to form a focus in each position inside the material being tested on the receiving side, and wherein the ultrasonic flaw detection equipment is configured in such a manner that:

in the vertical flaw detection, during pseudo electronic scanning, a direction of an ultrasonic beam of each group of transducers to be shifted is brought into correspondence with each position in the counter section by providing a correction value to the address in reading from the waveform memory, and in the oblique flaw detection, during pseudo electronic scanning, a direction of an ultrasonic beam of each group of transducers to be shifted is brought into correspondence with each position in the adjacent section by providing another correction value to the address in reading from the waveform memory.

8. The ultrasonic flaw detection equipment according to claim 6, further comprising:

a gate calculating unit, wherein in the oblique flaw detection, the gate calculating unit is configured to set a flaw detection gate for each group of transducers to be shifted during pseudo electronic scanning, the flaw detection gate being set according to a distance between a transducer and an incident point of the ultrasonic waves from the transducer, the ultrasonic waves entering the material being tested at the incident point, with reference to surface waves obtained by transmission in the vertical flaw detection.

9. The ultrasonic flaw detection equipment according to claim 1, wherein the pseudo electronic scanning is pseudo scanning performed on a receiving side in place of electronic scanning in which scanning is performed by sequentially exciting the arranged transducers of the array probe along a direction in which the transducers are arranged at a time of transmission of the ultrasonic waves, the pseudo scanning in which the arranged transducers are brought into correspondence with addresses of the waveform memories, data of received waves obtained by exciting all the arranged transducers of the array probe at one time at a time of transmission of ultrasonic waves is recorded on the waveform memories, and, in reading data from the waveform memory, data in the memory is read by sequentially shifting, in a direction corresponding to an electronic scanning direction of the transducer, the address of the memory corresponding to the transducer necessary to form a focus in each position inside the material being tested on the receiving side, and wherein the ultrasonic flaw detection equipment is configured in such a manner that:

in the vertical flaw detection, during pseudo electronic scanning, a direction of an ultrasonic beam of each group of transducers to be shifted is brought into correspondence with each position in the counter section by providing a correction value to the address in reading from the waveform memory, and in the oblique flaw detection, during pseudo electronic scanning, a direction of an ultrasonic beam of each group of transducers to be shifted is brought into correspondence with each position in the adjacent section by providing another correction value to the address in reading from the waveform memory.

10. The ultrasonic flaw detection equipment according to claim 9, wherein the correction value in the vertical flaw detection is configured to bring a beam of each of the transducers forming a same group into correspondence with one point on the counter section by providing thereto an angle of incidence set with consideration given to a corresponding one of angles of refraction which are different from each other at incident points of the transducers, so that the transducers of the group have a same beam path length, and forms dynamic focusing for the same group, and the correction value in the oblique flaw detection is configured to bring at least a beam of each of the transducers forming a same group into correspondence with one point on the adjacent section by providing thereto an angle of incidence set with consideration given to a corresponding one of angles of refraction which are different from each other at incident points of the transducers, so that the transducers of the same group have a same beam path length.

11. The ultrasonic flaw detection equipment according to claim 9, further comprising:

a gate calculating unit, wherein in the oblique flaw detection, the gate calculating unit is configured to set a flaw detection gate for each group of transducers to be shifted during pseudo electronic scanning, the flaw detection gate being set according to a distance between a transducer and an incident point of the ultrasonic waves from the transducer, the ultrasonic waves entering the material being tested at the incident point, with reference to surface waves obtained by transmission in the vertical flaw detection.

12. The ultrasonic flaw detection equipment according to claim 1, further comprising:

a gate calculating unit, wherein in the oblique flaw detection, the gate calculating unit is configured to set a flaw detection gate for each group of transducers to be shifted during pseudo electronic scanning, the flaw detection gate being set according to a distance between a transducer and an incident point of the ultrasonic waves from the transducer, the ultrasonic waves entering the material being tested at the incident point, with reference to surface waves obtained by transmission in the vertical flaw detection.

13. An ultrasonic flaw detection equipment for performing internal flaw detection of a material being tested, the material having a substantially circular cross-sectional shape, the ultrasonic flaw detection equipment comprising:

a vertical flaw detection apparatus and an oblique flaw detection apparatus, the vertical flaw detection apparatus being configured to perform at least a vertical flaw detection, the oblique flaw detection apparatus being configured to perform at least an oblique flaw detection, wherein the vertical flaw detection apparatus and the oblique flaw detection apparatus each include:
a plurality of array probes each having a plurality of transducers, and arranged along a surface of the material being tested, the plurality of transducers being arranged along a circumference of a circle exhibited by the material being tested as seen in a sectional view of the material being tested;
an exciting unit configured to excite each transducer of the array probes;
a waveform memory configured to store an ultrasonic wave received echo received by each transducer as waveform data of each transducer;
a phase combining unit configured to read contents of the waveform memory in which the waveform data of each transducer is stored and performing phase combining; and
a focusing unit configured to provide, in reading from the waveform memory, an address of each waveform memory as an address corresponding to a beam path length of dynamic focusing for an arbitrary position in a pseudo electronic scanning range, and
wherein the vertical flaw detection apparatus and the oblique flaw detection apparatus each are configured to transmit ultrasonic waves toward the material being tested from all the transducers of the array probe at a time, receive reflection echoes thereof by all the transducers, combine A scope waveforms of elements, the A scope waveforms being stored in the waveform memory, by the phase combining unit, and perform evaluation,
the exciting unit of at least the vertical flaw detection apparatus is configured to excite each array probe to emit the ultrasonic waves to enter the material being tested from each position on an incident section which is a section on the circumference of the circle exhibited by the material being tested, the section along which the array probe is placed, as a result of the plurality of transducers of each array probe being vibrated once for a first time, and to make the ultrasonic waves, which diverged after converging in the material being tested, reach a counter section facing the incident section on the circumference of the circle exhibited by the material being tested,
the exciting unit of at least the oblique flaw detection apparatus is configured to excite each array probe to emit the ultrasonic waves enter the material being tested obliquely as a result of the plurality of transducers being vibrated once for a second time by exciting the transducers while gradually shifting timing from one end of an arc exhibited by an array toward another end of the arc, and to make the ultrasonic waves, which diverged after converging in the material being tested, reach an adjacent section adjacent to the counter section on the circumference of the circle exhibited by the material being tested,
the vertical flaw detection apparatus and the oblique flaw detection apparatus each include a reception angle correcting unit,
the reception angle correcting unit of the vertical flaw detection apparatus is configured to bring a direction in which each group of transducers to be shifted during pseudo electronic scanning emits ultrasonic waves into correspondence with each position in the counter section by providing a correction value to the address in reading from the waveform memory, and
the reception angle correcting unit of the oblique flaw detection apparatus is configured to bring a direction in which each group of transducers to be shifted during pseudo electronic scanning emits ultrasonic waves into correspondence with each position in the adjacent section by providing another correction value to the address in reading from the waveform memory.

14. The ultrasonic flaw detection equipment according to claim 13, wherein
the oblique flaw detection apparatus doubles as the vertical flaw detection apparatus, and
the oblique flaw detection apparatus is configured to perform the vertical flaw detection and the oblique flaw detection by making the exciting unit excite the transducers at least two times.

15. The ultrasonic flaw detection equipment according to claim 13, wherein
the correction value provided by the reception angle correcting unit is configured to form a delay pattern bringing a beam of each of the transducers forming a same group into correspondence with one point on the counter section in the vertical flaw detection apparatus and with one point on the adjacent section in the oblique flaw detection apparatus by providing thereto an angle of incidence set with consideration given to a corresponding one of angles of refraction which are different from each other at incident points of the transducers, so that the transducers of the group have a same beam path length.

16. The ultrasonic flaw detection equipment according to claim 15, wherein
the focusing unit includes a Y direction counter indicating a pseudo electronic scanning position y, a D depth direction counter indicating a depth position of focus, and a dynamic focusing phase correction memory in which an amount of phase correction at each focus position in a dynamic focusing method is stored,
the ultrasonic flaw detection equipment is configured to obtain the amount of phase correction at a focus position according to data of the Y direction counter and the D depth direction counter to an address of the dynamic focusing phase correction memory, and
the reception angle correcting unit is configured to add a delay pattern with respect to the angle of incidence to the data of the counters, the data to be provided to the address of the dynamic focusing phase correction memory.

17. The ultrasonic flaw detection equipment according to claim 16, wherein
the reception angle correcting unit includes a reception delay pattern holding section and a receiving-side selection holding section,
the reception delay pattern holding section is configured to hold a delay pattern of the amount of correction according to the angle of incidence, and
the receiving-side selection holding section is configured to identify a corresponding delay pattern in the reception delay pattern holding section by a selection of the angle of incidence.

18. An ultrasonic flaw detection method based on a volume focusing flaw detection method for performing internal flaw detection of a material, the material having a substantially circular cross-sectional shape, the ultrasonic flaw detection method comprising the steps of:
providing at least two array probes each having a plurality of transducers and arranged along a surface of the material being tested;

arranging the plurality of transducers of each array probe along a circumference of a circle exhibited by the material being tested;

exciting each transducer of the array probes to emit an ultrasonic wave to the material by an exciting unit;

transmitting ultrasonic waves toward the material from all the transducers at a time;

receiving reflection echoes of the ultrasonic waves from the material by each transducer;

storing the ultrasonic wave received echo received by each transducer as waveform data of each transducer in a waveform memory;

reading contents of the waveform memory in which the waveform data of each transducer is stored by a phase combining unit; and performing phase combining, wherein the internal flaw detection of the material includes a vertical flaw detection and an oblique flaw detection, in performing the vertical flaw detection, the exciting unit excites the transducers of each array probe to emit ultrasonic waves to enter the material from an incident section, which is a section on a circumference of the circle exhibited by the material being tested, along which the array probe is placed, and reach a counter section on the circumference of the circle exhibited by the material being tested, facing the incident section, so that the plurality of transducers are vibrated once for a first time and the vertical flaw detection is performed, and in performing the oblique flaw detection, the exciting unit excites the transducers of each array probe, while gradually shifting timing from one end of an arc exhibited by an array toward another end of the arc, to emit ultrasonic waves to enter the material from the incident side and reach one of adjacent sections adjacent to the counter section on the circumference of the circle exhibited by the material being tested, so that at least a continuous part of the plurality of transducers of the array probe are vibrated once for a second time and the oblique flaw detection is performed.

19. The ultrasonic flaw detection method according to claim 18, wherein after performing the flaw detection at one cross section of the material, by making the array probe perform scanning physically along an axial direction of the material being tested, the flaw detection is performed in another position in the axial direction.

20. The ultrasonic flaw detection method according to claim 18, further comprising the step of performing calibration prior to flaw detection, wherein instead of preparing a test piece for each diameter of the material being tested to be subjected to flaw detection, the test piece being used in performing calibration, and part of test pieces is complemented by using data on calibration performed on a test piece having a diameter greater than a diameter of the part of test pieces and data on calibration performed on a test piece having a diameter smaller than the diameter of the part of test pieces.

* * * * *